(12) United States Patent
Dalby et al.

(10) Patent No.: US 10,981,896 B2
(45) Date of Patent: Apr. 20, 2021

(54) INDOLINONE DERIVATIVES AS INHIBITORS OF MATERNAL EMBRYONIC LEUCINE ZIPPER KINASE

(71) Applicant: BOARD OF REGENTS, THE UNIVERSITY OF TEXAS SYSTEM, Austin, TX (US)

(72) Inventors: Kevin N. Dalby, Leander, TX (US); Ramakrishna Edupuganti, Austin, TX (US); Juliana Taliaferro, Austin, TX (US); Ju Hyeon Lee, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/489,803

(22) PCT Filed: Mar. 2, 2018

(86) PCT No.: PCT/US2018/020668
§ 371 (c)(1),
(2) Date: Aug. 29, 2019

(87) PCT Pub. No.: WO2018/160967
PCT Pub. Date: Sep. 7, 2018

(65) Prior Publication Data
US 2020/0010455 A1   Jan. 9, 2020

Related U.S. Application Data

(60) Provisional application No. 62/465,992, filed on Mar. 2, 2017.

(51) Int. Cl.
| | |
|---|---|
| *C07D 209/34* | (2006.01) |
| *C07D 403/12* | (2006.01) |
| *C07D 401/14* | (2006.01) |
| *C07D 405/14* | (2006.01) |
| *C07D 413/14* | (2006.01) |
| *A61K 45/06* | (2006.01) |

(52) U.S. Cl.
CPC ......... *C07D 403/12* (2013.01); *C07D 209/34* (2013.01); *C07D 401/14* (2013.01); *C07D 405/14* (2013.01); *C07D 413/14* (2013.01); *A61K 45/06* (2013.01)

(58) Field of Classification Search
CPC .................................................. C07D 209/34
See application file for complete search history.

(56) References Cited

U.S. PATENT DOCUMENTS

| | | | |
|---|---|---|---|
| 6,387,919 B1 | 5/2002 | Davis et al. | |
| 7,262,206 B2 | 8/2007 | Heckel et al. | |
| 2005/0009898 A1 | 1/2005 | Roth et al. | |
| 2005/0234120 A1* | 10/2005 | Heckel ................. | C07D 209/34 514/414 |

FOREIGN PATENT DOCUMENTS

WO   2013109388   7/2013

OTHER PUBLICATIONS

Cancer Drug Design and Discovery, Neidle, Stephen, ed. (Elsevier/Academic Press), pp. 427-431 (2008). (Year: 2008).*
Edupuganti et al. Bioorganic & Medicinal Chemistry 25 (2017) 2609-2616 (Year: 2017).*
Al-Ejeh, F., et al. "Meta-analysis of the global gene expression profile of triple-negative breast cancer identifies genes for the prognostication and treatment of aggressive breast cancer." Oncogenesis 3.4 (2014): e100-e100.
American Cancer Society. Cancer Facts & Figures 2015. Atlanta: American Cancer Society; 2015. 2015.
Anumanthan, Govindaraj, et al. "Oncogenic serine-threonine kinase receptor-associated protein modulates the function of Ewing sarcoma protein through a novel mechanism." Cancer research 66.22 (2006): 10824-10832.

(Continued)

*Primary Examiner* — Emily A Bernhardt
(74) *Attorney, Agent, or Firm* — Meunier Carlin & Curfman LLC

(57) ABSTRACT

The present disclosure relates to indolinone compounds, compositions, and methods for the inhibition of maternal embryonic leucine zipper kinase (MELK). The present disclosure further relates to indolinone compounds, compositions, and methods for the treatment or prevention of a cancer (for example, triple negative breast cancer). Disclosed herein are compounds according to Formula I:

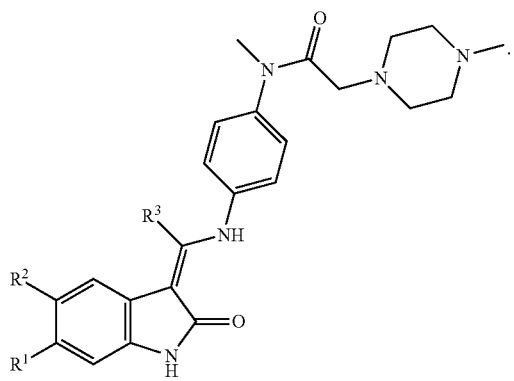

Formula I

2 Claims, 8 Drawing Sheets

(56) References Cited

OTHER PUBLICATIONS

Aronov, Alex M., et al. "Kinase-likeness and kinase-privileged fragments: toward virtual polypharmacology." Journal of medicinal chemistry 51.5 (2008): 1214-1222.
Badouel, Caroline, et al. "Maternal embryonic leucine zipper kinase is stabilized in mitosis by phosphorylation and is partially degraded upon mitotic exit." Experimental cell research 316.13 (2010): 2166-2173.
Badouel, Caroline, et al. "M-phase MELK activity is regulated by MPF and MAPK." Cell Cycle 5.8 (2006): 883-889.
Bartholomeusz, Chandra, et al. "PEA-15 inhibits tumorigenesis in an MDA-MB-468 triple-negative breast cancer xenograft model through increased cytoplasmic localization of activated extracellular signal-regulated kinase." Clinical Cancer Research 16.6 (2010): 1802-1811.
Beke, Lijs, et al. "MELK-T1, a small-molecule inhibitor of protein kinase MELK, decreases DNA-damage tolerance in proliferating cancer cells." Bioscience reports 35.6 (2015).
Bertolaet, Bonnie L., et al. "UBA domains mediate protein-protein interactions between two DNA damage-inducible proteins." Journal of molecular biology 313.5 (2001): 955-963.
Bessone, Stéphanie, et al. "EMK protein kinase-null mice: dwarfism and hypofertility associated with alterations in the somatotrope and prolactin pathways." Developmental biology 214.1 (1999): 87-101.
Beullens, Monique, et al. "Substrate specificity and activity regulation of protein kinase MELK." Journal of Biological Chemistry 280.48 (2005): 40003-40011.
Bianchini, Giampaolo, et al. "Prognostic and therapeutic implications of distinct kinase expression patterns in different subtypes of breast cancer." Cancer research 70.21 (2010): 8852-8862.
Blot, Joëlle, et al. "Cell cycle regulation of pEg3, a new Xenopus protein kinase of the KIN1/PAR-1/MARK family." Developmental biology 241.2 (2002): 327-338.
Brattsand, Göran, et al. "Cell-cycle-regulated phosphorylation of oncoprotein 18 on Ser16, Ser25 and Ser38." European journal of biochemistry 220.2 (1994): 359-368.
Bright, N. J., C. Thornton, and D. Carling. "The regulation and function of mammalian AMPK-related kinases." Acta physiologica 196.1 (2009): 15-26.
Brunen, Diede, et al. "TGF-β: an emerging player in drug resistance." Cell cycle 12.18 (2013): 2960-2968.
Buchberger, Alexander. "From UBA to UBX: new words in the ubiquitin vocabulary." Trends in cell biology 12.5 (2002): 216-221.
Canevari, Giulia, et al. "Structural insight into maternal embryonic leucine zipper kinase (MELK) conformation and inhibition toward structure-based drug design." Biochemistry 52.37 (2013): 6380-6387.
Cantagrel, Guillaume, et al. "Iron Trichloride-Promoted Cyclization of o-Alkynylaryl Isocyanates: Synthesis of 3-(Chloromethylene) oxindoles." Organic letters 11.19 (2009): 4262-4265.
Cao, et al., "Structural basis for the regulation of maternal embryonic leucine zipper kinase." PLoS One, 2013. 8(7): p. e70031.
Chartrain, Isabelle, Anne Couturier, and Jean-Pierre Tassan. "Cell-cycle-dependent cortical localization of pEg3 protein kinase in Xenopus and human cells." Biology of the Cell 98.4 (2006): 253-263.
Chartrain, Isabelle, et al. "Cell-cycle dependent localization of MELK and its new partner RACK1 in epithelial versus mesenchyme-like cells in Xenopus embryo." Biology open 2.10 (2013): 1037-1048.
Chien, Shih-Chieh, et al. "Caenorhabditis elegans PIG-1/MELK acts in a conserved PAR-4/LKB1 polarity pathway to promote asymmetric neuroblast divisions." Genetics 193.3 (2013): 897-909.
Cho, Yong-Soon, et al. "The crystal structure of MPK38 in complex with OTSSP167, an orally administrative MELK selective inhibitor." Biochemical and biophysical research communications 447.1 (2014): 7-11.
Cho, Y-S., et al. "The structures of the kinase domain and UBA domain of MPK38 suggest the activation mechanism for kinase activity." Acta Crystallographica Section D: Biological Crystallography 70.2 (2014): 514-521.
Choi, Seungho, and Ja-Lok Ku. "Resistance of colorectal cancer cells to radiation and 5-FU is associated with MELK expression." Biochemical and biophysical research communications 412.2 (2011): 207-213.
Chung, Suyoun, et al. "Development of an orally-administrative MELK-targeting inhibitor that suppresses the growth of various types of human cancer." Oncotarget 3.12 (2012): 1629.
Cordes, Shaun, C. Andrew Frank, and Gian Garriga. "The C. elegans MELK ortholog PIG-1 regulates cell size asymmetry and daughter cell fate in asymmetric neuroblast divisions." Development 133.14 (2006): 2747-2756.
Datta, Pran K., and Harold L. Moses. "STRAP and Smad7 synergize in the inhibition of transforming growth factor β signaling." Molecular and cellular biology 20.9 (2000): 3157-3167.
Davezac, Noelie, et al. "Human pEg3 kinase associates with and phosphorylates CDC25B phosphatase: a potential role for pEg3 in cell cycle regulation." Oncogene 21.50 (2002): 7630-7641.
Davies, Gareth C., et al. "Cbl-b interacts with ubiquitinated proteins; differential functions of the UBA domains of c-Cbl and Cbl-b." Oncogene 23.42 (2004): 7104-7115.
Du, Tao, et al. "Maternal embryonic leucine zipper kinase enhances gastric cancer progression via the FAK/Paxillin pathway." Molecular cancer 13.1 (2014): 100.
Elbert, Maya, Guendalina Rossi, and Patrick Brennwald. "The yeast par-1 homologs kin1 and kin2 show genetic and physical interactions with components of the exocytic machinery." Molecular biology of the cell 16.2 (2005): 532-549.
Elkins, Jonathan M., et al. "Comprehensive characterization of the published kinase inhibitor set." Nature biotechnology 34.1 (2016): 95.
Espinosa, L., and E. Navarro. "Human serine/threonine protein kinase EMK1: genomic structure and cDNA cloning of isoforms produced by alternative splicing." Cytogenetic and Genome Research 81.3-4 (1998): 278-282.
Finetti, Pascal, et al. "Sixteen—Kinase Gene Expression Identifies Luminal Breast Cancers with Poor Prognosis." Cancer research 68.3 (2008): 767-776.
Furtmann, Norbert, Ye Hu, and Jürgen Bajorath. "Comprehensive analysis of three-dimensional activity cliffs formed by kinase inhibitors with different binding modes and cliff mapping of structural analogues." Journal of medicinal chemistry 58.1 (2015): 252-264.
Giam, M., et al. "Bcl-2 family member Bcl-G is not a proapoptotic protein." Cell death & disease 3.10 (2012): e404-e404.
Gil, Minchan, et al. "Cloning and expression of a cDNA encoding a novel protein serine/threonine kinase predominantly expressed in hematopoietic cells." Gene 195.2 (1997): 295-301.
Gloeckner, Herma, Tarja Jonuleit, and Horst-Dieter Lemke. "Monitoring of cell viability and cell growth in a hollow-fiber bioreactor by use of the dye Alamar Blue™." Journal of immunological methods 252.1-2 (2001): 131-138.
Gradishar, William J., et al. "Breast cancer version 2.2015." Journal of the National Comprehensive Cancer Network 13.4 (2015): 448-475.
Gray, Daniel, et al. "Maternal embryonic leucine zipper kinase/murine protein serine-threonine kinase 38 is a promising therapeutic target for multiple cancers." Cancer research 65.21 (2005): 9751-9761.
Gu, Chunyu, et al. "Tumor-specific activation of the C-JUN/MELK pathway regulates glioma stem cell growth in a p53-dependent manner." Stem cells 31.5 (2013): 870-881.
Guo, Su, and Kenneth J. Kemphues. "A non-muscle myosin required for embryonic polarity in Caenorhabditis elegans." Nature 382.6590 (1996): 455-458.
Halder, Sunil K., et al. "Oncogenic function of a novel WD-domain protein, STRAP, in human carcinogenesis." Cancer research 66.12 (2006): 6156-6166.
Hartmann-Petersen, Rasmus, et al. "UBA domain containing proteins in fission yeast." The international journal of biochemistry & cell biology 35.5 (2003): 629-636.

(56) References Cited

OTHER PUBLICATIONS

Hebbard, Lionel W., et al. "Maternal embryonic leucine zipper kinase is upregulated and required in mammary tumor-initiating cells in vivo." Cancer research 70.21 (2010): 8863-8873.
Hemmati, Houman D., et al. "Cancerous stem cells can arise from pediatric brain tumors." Proceedings of the National Academy of Sciences 100.25 (2003): 15178-15183.
Heyer, Babette S., et al. "New member of the Snf1/AMPK kinase family, Melk, is expressed in the mouse egg and preimplantation embryo." Molecular Reproduction and Development: Incorporating Gamete Research 47.2 (1997): 148-156.
Heyer, Babette S., Helga Kochanowski, and Davor Solter. "Expression of Melk, a new protein kinase, during early mouse development." Developmental dynamics: an official publication of the American Association of Anatomists 215.4 (1999): 344-351.
Hurov, Jonathan B., Janis L. Watkins, and Helen Piwnica-Worms. "Atypical PKC phosphorylates PAR-1 kinases to regulate localization and activity." Current Biology 14.8 (2004): 736-741.
Hurov, Kristen E., Cecilia Cotta-Ramusino, and Stephen J. Elledge. "A genetic screen identifies the Triple T complex required for DNA damage signaling and ATM and ATR stability." Genes & development 24.17 (2010): 1939-1950.
Hutchinson, Lisa, and Rebecca Kirk. "High drug attrition rates—where are we going wrong?." (2011): 189.
Inoue, Hiroyuki, et al. "Effective growth-suppressive activity of maternal embryonic leucine-zipper kinase (MELK) inhibitor against small cell lung cancer." Oncotarget 7.12 (2016): 13621.
Ji, Wenbin, et al. "OTSSP167 abrogates mitotic checkpoint through inhibiting multiple mitotic kinases." PLoS One 11.4 (2016): e0153518.
Johnson, Christopher N., et al. "Fragment-based discovery of type I inhibitors of maternal embryonic leucine zipper kinase." ACS medicinal chemistry letters 6.1 (2015): 25-30.
Johnson, Christopher N., et al. "Structure-Based design of type II inhibitors applied to maternal embryonic leucine zipper kinase." ACS medicinal chemistry letters 6.1 (2015): 31-36.
Joshi, Kaushal, et al. "MELK-dependent FOXM1 phosphorylation is essential for proliferation of glioma stem cells." Stem cells 31.6 (2013): 1051-1063.
Jung, Haiyoung, Hyun-A. Seong, and Hyunjung Ha. "Murine protein serine/threonine kinase 38 activates apoptosis signal-regulating kinase 1 via Thr838 phosphorylation." Journal of Biological Chemistry 283.50 (2008): 34541-34553.
Jung, Haiyoung, Hyun-A. Seong, and Hyunjung Ha. "NM23-H1 tumor suppressor and its interacting partner STRAP activate p53 function." Journal of Biological Chemistry 282.48 (2007): 35293-35307.
Kao, Jessica, et al. "Molecular profiling of breast cancer cell lines defines relevant tumor models and provides a resource for cancer gene discovery." PloS one 4.7 (2009).
Kappadakunnel, Melanie, et al. "Stem cell associated gene expression in glioblastoma multiforme: relationship to survival and the subventricular zone." Journal of neuro-oncology 96.3 (2010): 359-367.
Kato, Taigo, et al. "Oncogenic roles of TOPK and MELK, and effective growth suppression by small molecular inhibitors in kidney cancer cells." Oncotarget 7.14 (2016): 17652.
Kig, Cenk, et al. "Maternal embryonic leucine zipper kinase (MELK) reduces replication stress in glioblastoma cells." Journal of Biological Chemistry 288.33 (2013): 24200-24212.
Komatsu, Masato, et al. "Molecular features of triple negative breast cancer cells by genome-wide gene expression profiling analysis." International journal of oncology 42.2 (2013): 478-506.
Kuner, Ruprecht, et al. "The maternal embryonic leucine zipper kinase (MELK) is upregulated in high-grade prostate cancer." Journal of molecular medicine 91.2 (2013): 237-248.
Le Page, Yann, et al. "A functional analysis of MELK in cell division reveals a transition in the mode of cytokinesis during Xenopus development." Journal of cell science 124.6 (2011): 958-968.
Lehmann, Brian D., et al. "Identification of human triple-negative breast cancer subtypes and preclinical models for selection of targeted therapies." The Journal of clinical investigation 121.7 (2011): 2750-2767.
Lin, Meng-Lay, et al. "Involvement of maternal embryonic leucine zipper kinase (MELK) in mammary carcinogenesis through interaction with Bcl-G, a pro-apoptotic member of the Bcl-2 family." Breast Cancer Research 9.1 (2007): R17.
Madura, Kiran. "The ubiquitin-associated (UBA) domain: on the path from prudence to prurience." Cell Cycle 1.4 (2002): 233-242.
Manning, Gerard, et al. "The protein kinase complement of the human genome." Science 298.5600 (2002): 1912-1934.
Manoharan, Ravi, Hyun-A. Seong, and Hyunjung Ha. "Thioredoxin inhibits MPK38-induced ASK1, TGF-β, and p53 function in a phosphorylation-dependent manner." Free Radical Biology and Medicine 63 (2013): 313-324.
Marie, Suely KN, et al. "Maternal embryonic leucine zipper kinase transcript abundance correlates with malignancy grade in human astrocytomas." International journal of cancer 122.4 (2008): 807-815.
Marie, Suely Kazue Nagahashi, et al. "Stathmin involvement in the maternal embryonic leucine zipper kinase pathway in glioblastoma." Proteome science 14.1 (2016): 6.
Mathea, Sebastian, et al. "Structure of the human protein kinase ZAK in complex with vemurafenib." ACS chemical biology 11.6 (2016): 1595-1602.
Miduturu, Chandrasekhar V., et al. "High-throughput kinase profiling: a more efficient approach toward the discovery of new kinase inhibitors." Chemistry & biology 18.7 (2011): 868-879.
Minata, M., et al., Multi-Kinase Inhibitor C1 Triggers Mitotic Catastrophe of Glioma Stem Cells Mainly through MELK Kinase Inhibition. PLoS One, 2014. 9(4): p. e92546.
Moravcevic, Katarina, et al. "Kinase associated-1 domains drive MARK/PAR1 kinases to membrane targets by binding acidic phospholipids." Cell 143.6 (2010): 966-977.
Mueller, Thomas D., Mariusz Kamionka, and Juli Feigon. "Specificity of the interaction between ubiquitin-associated domains and ubiquitin." Journal of Biological Chemistry 279.12 (2004): 11926-11936.
Nagase, T., et al., Prediction of the coding sequences of unidentified human genes. VI. The coding sequences of 80 new genes (KIAA0201-KIAA0280) deduced by analysis of cDNA clones from cell line KG-1 and brain. DNA Res, 1996. 3(5): p. 321-329.
Nakano, Ichiro, et al. "Maternal embryonic leucine zipper kinase is a key regulator of the proliferation of malignant brain tumors, including brain tumor stem cells." Journal of neuroscience research 86.1 (2008): 48-60.
Nakano, Ichiro, et al. "Siomycin A targets brain tumor stem cells partially through a MELK-mediated pathway." Neuro-oncology 13.6 (2011): 622-634.
Nakano, Ichiro, et al. "Maternal embryonic leucine zipper kinase (MELK) regulates multipotent neural progenitor proliferation." The Journal of cell biology 170.3 (2005): 413-427.
Neumann, Dietbert, et al. "Mammalian AMP-activated protein kinase: functional, heterotrimeric complexes by co-expression of subunits in *Escherichia coli*." Protein expression and purification 30.2 (2003): 230-237.
Niesler, Carola U., Katherine H. Myburgh, and Frances Moore. "The changing AMPK expression profile in differentiating mouse skeletal muscle myoblast cells helps confer increasing resistance to apoptosis." Experimental physiology 92.1 (2007): 207-217.
Park, Yun-Yong, et al. "FOXM1 mediates Dox resistance in breast cancer by enhancing DNA repair." Carcinogenesis 33.10 (2012): 1843-1853.
Pavletich, Nikola P. "Mechanisms of cyclin-dependent kinase regulation: structures of Cdks, their cyclin activators, and Cip and INK4 inhibitors." Journal of molecular biology 287.5 (1999): 821-828.
Pickard, Mark R., Mirna Mourtada-Maarabouni, and Gwyn T. Williams. "Candidate tumour suppressor Fau regulates apoptosis in human cells: An essential role for Bcl-G." Biochimica et Biophysica Acta (BBA)—Molecular Basis of Disease 1812.9 (2011): 1146-1153.

(56) References Cited

OTHER PUBLICATIONS

Pickard, Mark R., et al. "Dysregulated expression of Fau and MELK is associated with poor prognosis in breast cancer." Breast cancer research 11.4 (2009): R60.
Prakash, C., and S. Raja. "Indolinones as promising scaffold as kinase inhibitors: a review." Mini reviews in medicinal chemistry 12.2 (2012): 98-119.
Rajkumar, Thangarajan, et al. "Identification and validation of genes involved in cervical tumourigenesis." BMC cancer 11.1 (2011): 80.
Rhodes, Daniel R., et al. "Large-scale meta-analysis of cancer microarray data identifies common transcriptional profiles of neoplastic transformation and progression." Proceedings of the National Academy of Sciences 101.25 (2004): 9309-9314.
Risinger, John, et al. "Gene expression analysis of early stage endometrial cancers reveals unique transcripts associated with grade and histology but not depth of invasion." Frontiers in oncology 3 (2013): 139.
Roth, Gerald J., et al. "Design, synthesis, and evaluation of indolinones as triple angiokinase inhibitors and the discovery of a highly specific 6-methoxycarbonyl-substituted indolinone (BIBF 1120)." Journal of medicinal chemistry 52.14 (2009): 4466-4480.
Rubin, Camelia Iancu, and George F. Atweh. "The role of stathmin in the regulation of the cell cycle." Journal of cellular biochemistry 93.2 (2004): 242-250.
Ryu, Byungwoo, et al. "Comprehensive expression profiling of tumor cell lines identifies molecular signatures of melanoma progression." PloS one 2.7 (2007), 2(7):e594.
Saito, Rika, Hiromitsu Nakauchi, and Sumiko Watanabe. "Serine/threonine kinase, Melk, regulates proliferation and glial differentiation of retinal progenitor cells." Cancer science 103.1 (2012): 42-49.
Sanchez, Yolanda, et al. "Conservation of the Chk1 checkpoint pathway in mammals: linkage of DNA damage to Cdk regulation through Cdc25." Science 277.5331 (1997): 1497-1501.
Sarhadi, Virinder Kaur, et al. "Copy number alterations and neoplasia-specific mutations in MELK, PDCD1LG2, TLN1, and PAX5 at 9p in different neoplasias." Genes, Chromosomes and Cancer 53.7 (2014): 579-588.
Scott, John W., et al. "Autophosphorylation of CaMKK2 generates autonomous activity that is disrupted by a T85S mutation linked to anxiety and bipolar disorder." Scientific reports 5 (2015): 14436.
Seong, Hyun-A., and Hyunjung Ha. "Murine protein serine-threonine kinase 38 activates p53 function through Ser15 phosphorylation." Journal of Biological Chemistry 287.25 (2012): 20797-20810.
Seong, Hyun-A., et al. "Positive regulation of apoptosis signal-regulating kinase 1 signaling by ZPR9 protein, a zinc finger protein." Journal of Biological Chemistry 286.36 (2011): 31123-31135.
Seong, Hyun-A., Haiyoung Jung, and Hyunjung Ha. "Murine protein serine/threonine kinase 38 stimulates TGF-β signaling in a kinase-dependent manner via direct phosphorylation of Smad proteins." Journal of Biological Chemistry 285.40 (2010): 30959-30970.
Seong, Hyun-A., Ravi Manoharan, and Hyunjung Ha. "A crucial role for the phosphorylation of STRAP at Ser188 by MPK38 in STRAP-dependent cell death through ASK1, TGF-β , p53, and PI3K/PDK1 signaling pathways." Cell cycle 13.21 (2014): 3357-3374.
Sievers, Fabian, et al. "Fast, scalable generation of high-quality protein multiple sequence alignments using Clustal Omega." Molecular systems biology 7.1 (2011).p. 539.
Speers, Corey, et al. "Identification of novel kinase targets for the treatment of estrogen receptor-negative breast cancer." Clinical Cancer Research 15.20 (2009): 6327-6340.
Straight, Aaron F., Christine M. Field, and Timothy J. Mitchison. "Anillin binds nonmuscle myosin II and regulates the contractile ring." Molecular biology of the cell 16.1 (2005): 193-201.
Tischner, D. and A. Villunger, Bcl-G acquitted of murder! Cell Death Dis, 2012. 3: p. e405.
Tochio, Naoya, et al. "Solution structure of the kinase-associated domain 1 of mouse microtubule-associated protein/microtubule affinity-regulating kinase 3." Protein science 15.11 (2006): 2534-2543.
Toure, B. Barry, et al. "Toward the validation of maternal embryonic leucine zipper kinase: discovery, optimization of highly potent and selective inhibitors, and preliminary biology insight." Journal of Medicinal Chemistry 59.10 (2016): 4711-4723.
Uitdehaag, Joost CM, et al. "A guide to picking the most selective kinase inhibitor tool compounds for pharmacological validation of drug targets." British journal of pharmacology 166.3 (2012): 858-876.
Verlinden, Lieve, et al. "Characterization of the condensin component Cnap1 and protein kinase Melk as novel E2F target genes down-regulated by 1, 25-dihydroxyvitamin D3." Journal of Biological Chemistry 280.45 (2005): 37319-37330.
Vulsteke V, et al. The Journal of biological chemistry. 2004;279(10):8642-8647.
Waas, William F., and Kevin N. Dalby. "Purification of a model substrate for transcription factor phosphorylation by ERK2." Protein expression and purification 23.1 (2001): 191-197.
Waas, William F., and Kevin N. Dalby. "Transient protein-protein interactions and a random-ordered kinetic mechanism for the phosphorylation of a transcription factor by extracellular-regulated protein kinase 2." Journal of Biological Chemistry 277.15 (2002): 12532-12540.
Wang, Yubao, et al. "MELK is an oncogenic kinase essential for mitotic progression in basal-like breast cancer cells." Elife 3 (2014): e01763.
Waterhouse, Andrew M., et al. "Jalview Version 2—a multiple sequence alignment editor and analysis workbench." Bioinformatics 25.9 (2009): 1189-1191.
Wierstra, Inken. "The transcription factor FOXM1 (Forkhead box M1): proliferation-specific expression, transcription factor function, target genes, mouse models, and normal biological roles." Advances in cancer research. vol. 118. Academic Press, 2013. 97-398.
Wonsey, Diane R., and Maximillian T. Follettie. "Loss of the forkhead transcription factor FoxM1 causes centrosome amplification and mitotic catastrophe." Cancer research 65.12 (2005): 5181-5189.
Woods, A., et al., LKB1 is the upstream kinase in the AMP-activated protein kinase cascade. Curr Biol, 2003. 13(22): p. 2004-2008.
Xue, Jianfei, et al. "Sustained activation of SMAD3/SMAD4 by FOXM1 promotes TGF-β-dependent cancer metastasis." The Journal of clinical investigation 124.2 (2014): 564-579.
Xue, Ling, et al. "FoxM1, a forkhead transcription factor is a master cell cycle regulator for mouse mature T cells but not double positive thymocytes." PloS one 5.2 (2010). e9229.
Zhao, Baoguang, et al. "Structural basis for Chk1 inhibition by UCN-01." Journal of Biological Chemistry 277.48 (2002): 46609-46615.
International Preliminary Report on Patentability issued for Application No. PCT/US2018/020668, dated Sep. 12, 2019.
International Search Report and Written Opinion in PCT/US2018/020668, dated Apr. 25, 2018. 9 pages.
Cenik, BK et al. "BIBF 1120 (Nintedanib), a triple angiokinase inhibitor, induces hypoxia but not EMT and blocks progression of preclinical models of lung and pancreatic cancer". Jun. 6, 2013, Molecular Cancer Therapeutics; vol. 12, Issue 6, pp. 992-1001; abstract; p. 993, first column, last paragraph, p. 993, second column, first and second paragraphs, p. 995, figure 1.

\* cited by examiner

INDOLINONE DERIVATIVES AS INHIBITORS OF MATERNAL EMBRYONIC LEUCINE ZIPPER KINASE

CROSS REFERENCE TO RELATED APPLICATIONS

This application is a national stage application filed under 35 U.S.C. § 371 of PCT/US2018/020668 filed Mar. 2, 2018, which claims the benefit of U.S. Provisional Patent Application Ser. No. 62/465,992 filed Mar. 2, 2017, which are expressly incorporated herein by reference in its entirety.

FIELD

The present disclosure relates to indolinone compounds, compositions, and methods for the inhibition of maternal embryonic leucine zipper kinase (MELK). The present disclosure further relates to indolinone compounds, compositions, and methods for the treatment or prevention of a cancer (for example, triple negative breast cancer).

BACKGROUND

Over the last two decades, protein kinases have represented a major field for drug discovery and development. However, one of these protein kinases, maternal embryonic leucine zipper kinase (MELK), has yet to be targeted by an FDA approved therapeutic.

Maternal embryonic leucine zipper kinase (MELK) is evolutionarily conserved in eukaryotes from nematodes to humans. In contrast to most members of the AMPK-RK family, which mediate cell survival under stressful metabolic conditions, MELK has been implicated in multiple cellular processes, including cell cycle checkpoint regulation, proliferation, apoptosis, and RNA processing. MELK is expressed in the early stages of murine embryonic development, but MELK knockout mice develop normally with no obvious pathologic phenotype, suggesting that MELK's developmentally-related functions may be redundant. Yet despite its apparent dispensable nature in differentiated adult cells, evidence has implicated MELK's importance in proliferating progenitor populations, including multipotent neural progenitors, myoblasts, and mammary progenitors. Interestingly, MELK inhibition does not affect survival in normal neural stem cells, but siRNA-mediated MELK knockdown induces apoptosis selectively in glioma stem cells. Such data reinforces the redundancy of MELK function in noncancerous cells, but also implicates the existence of an exploitable target in certain cancer stem cell populations.

In addition to its putative role in cancer stem cells, upregulated MELK mRNA and protein levels have been observed in a wide array of cancer cell types and clinical tumor samples. Of particular note is the fact that MELK expression correlates with poor prognosis in the most aggressive subsets of disease, including glioblastoma multiforme (GBM) and triple negative breast cancer (TNBC). Factors contributing to poor outlook for TNBC patients in part stems from the cancer's ability not only to proliferate quickly, but also its propensity to spread and recur in distant organs. From a molecular biology perspective, mounting evidence continues to implicate MELK in direct and transcriptional regulation of cell division in the context of malignancy. Furthermore, MELK has also been preliminarily linked to metastasis through its involvement with TGF-ß driven epithelial-to-mesenchymal transition (EMT). The cancer-specific expression pattern, combined with the clinical and biological data have therefore justifiably fostered strong interest in MELK as a clinical target.

The compounds, compositions, and methods disclosed herein address these and other needs.

SUMMARY

Disclosed herein are indolinone compounds, compositions, and methods for the potent and selective inhibition of maternal embryonic leucine zipper (MELK) kinase. In some embodiments, the present disclosure further relates to indolinone compounds, compositions, and methods for the treatment or prevention of a cancer (for example, triple negative breast cancer).

In one aspect, disclosed herein is a compound of Formula I:

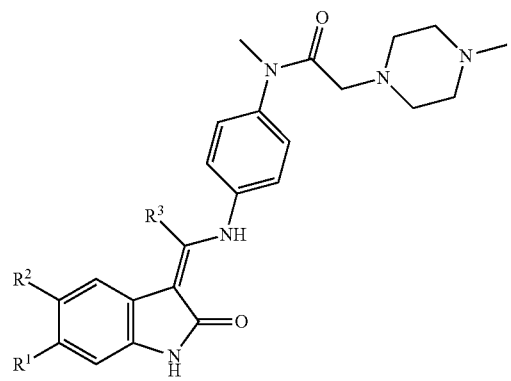

Formula I wherein:
$R^1$ is hydrogen;
$R^2$ is selected from carboxylic acid, ester, amide, acyl, alkoxy, sulfonamide, alkylamino, aminoacyl, or amino; and
$R^3$ is selected from aryl or heteroaryl;
or a pharmaceutically acceptable salt thereof.

In one aspect, disclosed herein is a compound of Formula II:

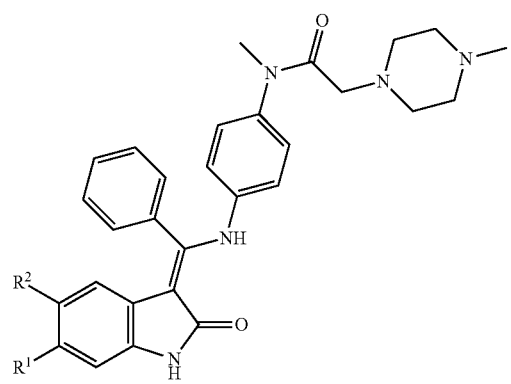

Formula II wherein:
$R^1$ is hydrogen; and
$R^2$ is selected from carboxylic acid, ester, amide, acyl, alkoxy, sulfonamide, alkylamino, aminoacyl, or amino;

or a pharmaceutically acceptable salt thereof.

In one aspect, disclosed herein is a compound of Formula III:

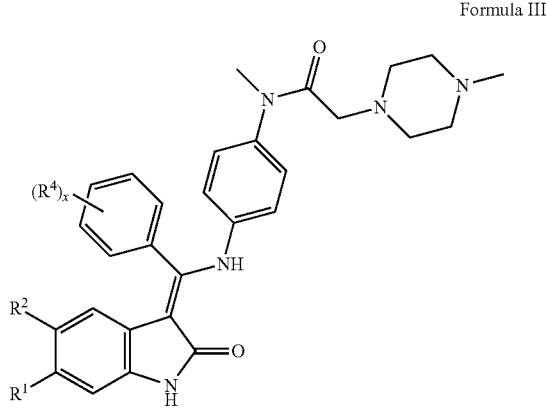

Formula III wherein:

R¹ is hydrogen;

R² is selected from carboxylic acid, ester, amide, acyl, alkoxy, sulfonamide, alkylamino, aminoacyl, amino, nitro, aryl, or heteroaryl;

each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or two R⁴ come together to form a carbocyclic ring or a heterocyclic ring;

R⁵ and R⁶ are independently selected from hydrogen, alkyl, alkylamino, heterocycloalkyl, acyl, or ester; and x is selected from 1 or 2;

or a pharmaceutically acceptable salt thereof.

In one aspect, disclosed herein is a compound of Formula IV:

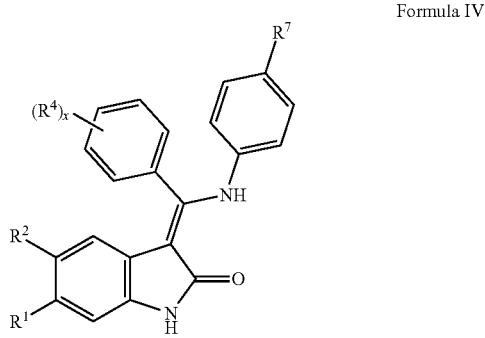

Formula IV wherein:

R¹ is hydrogen;

R² is selected from carboxylic acid, ester, amide, acyl, alkoxy, sulfonamide, alkylamino, aminoacyl, amino, nitro, aryl, or heteroaryl;

each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or two R⁴ come together to form a carbocyclic ring or a heterocyclic ring;

R⁵ and R⁶ are independently selected from hydrogen, alkyl, alkylamino, heterocycloalkyl, acyl, or ester;

R⁷ is selected from NR⁸R⁹, alkyl, alkylamino, heterocycloalkyl, or heterocycloalkylalkyl;

R⁸ and R⁹ are independently selected from hydrogen, alkyl, alkylamino, heterocycloalkyl, heterocycloalkylalkyl, or acyl; and x is selected from 1 or 2;

or a pharmaceutically acceptable salt thereof.

In one embodiment, the compound is

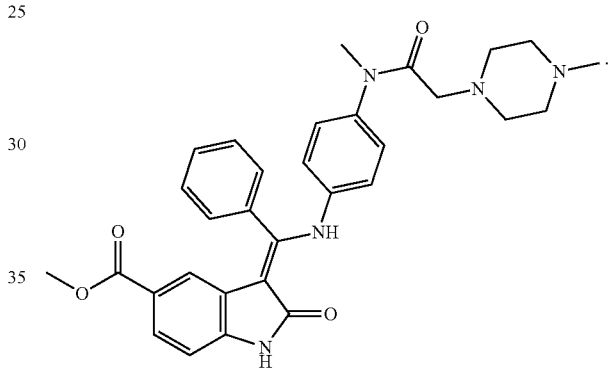

In another embodiment, the compound is

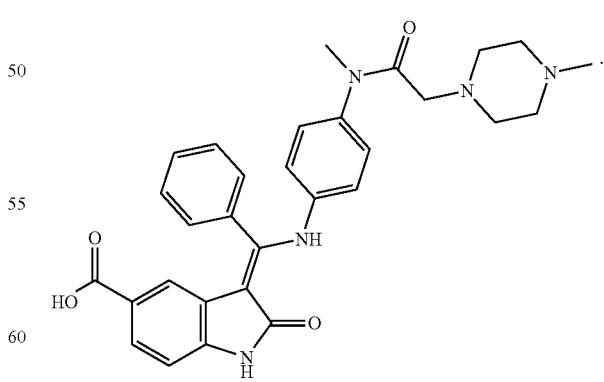

In one aspect, provided herein is a method for the treatment of a cancer, comprising: administering an effective amount of a compound of Formula I to a host in need thereof:

Formula I

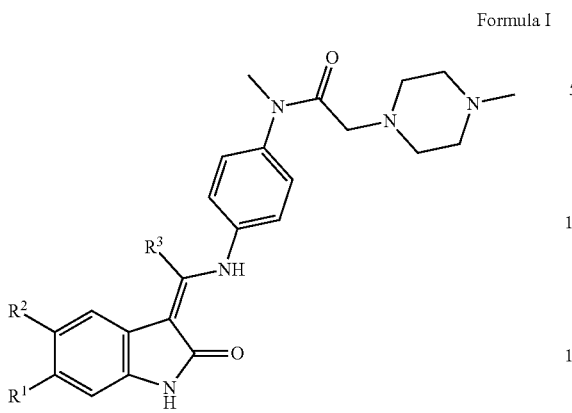

wherein:
R¹ is hydrogen;
R² is selected from carboxylic acid, ester, amide, acyl, alkoxy, sulfonamide, alkylamino, aminoacyl, or amino; and
R³ is selected from aryl or heteroaryl;
or a pharmaceutically acceptable salt thereof.

In another aspect, provided herein is a method for the treatment of a cancer, comprising: administering an effective amount of a compound of Formula II to a host in need thereof:

Formula II

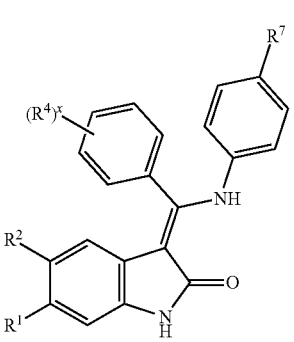

wherein:
R¹ is hydrogen; and
R² is selected from carboxylic acid, ester, amide, acyl, alkoxy, sulfonamide, alkylamino, aminoacyl, or amino;
or a pharmaceutically acceptable salt thereof.

In one aspect, provided herein is a method for the treatment of a cancer, comprising: administering an effective amount of a compound of Formula III to a host in need thereof:

Formula III

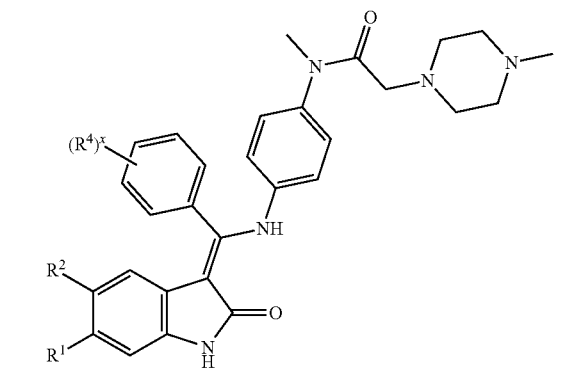

wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;
R⁵ and R⁶ are independently selected from hydrogen, alkyl, alkylamino, heterocycloalkyl, acyl, or ester; and
x is selected from 1 or 2;
or a pharmaceutically acceptable salt thereof.

In one aspect, provided herein is a method for the treatment of a cancer, comprising: administering an effective amount of a compound of Formula IV to a host in need thereof:

Formula IV wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;

$R^5$ and $R^6$ are independently selected from hydrogen, alkyl, alkylamino, heterocycloalkyl, acyl, or ester;

$R^7$ is selected from $NR^8R^9$, alkyl, alkylamino, heterocycloalkyl, or heterocycloalkylalkyl;

$R^8$ and $R^9$ are independently selected from hydrogen, alkyl, alkylamino, heterocycloalkyl, heterocycloalkylalkyl, or acyl; and x is selected from 1 or 2;

or a pharmaceutically acceptable salt thereof.

In one embodiment, the cancer is selected from triple negative breast cancer or glioblastoma multiforme. In one embodiment, the cancer is triple negative breast cancer. In one embodiment, the cancer is glioblastoma multiforme.

In one embodiment, a compound of Formula I, II, III, or IV is administered in combination with an additional chemotherapeutic agent.

BRIEF DESCRIPTION OF THE DRAWINGS

The accompanying figures, which are incorporated in and constitute a part of this specification, illustrate several aspects described below.

DETAILED DESCRIPTION

Figure 1:
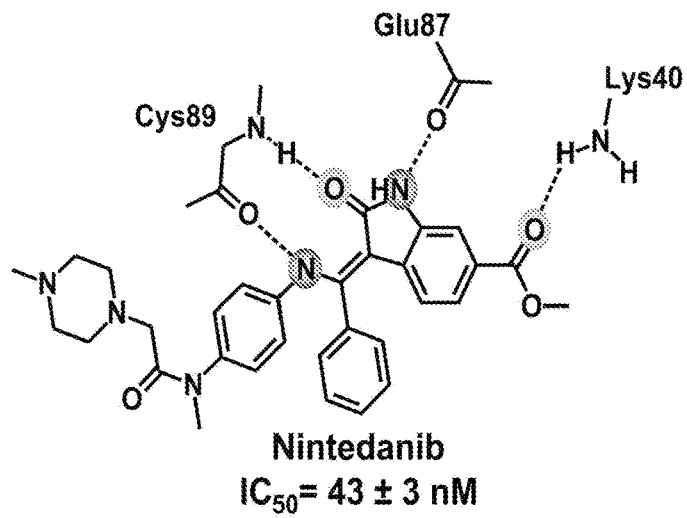
FIG. 1 shows the top 3 screening hits for inhibition of maternal embryonic leucine zipper kinase (MELK), with key predicted hydrogen-bonding interactions with MELK binding site and their $IC_{50}$'s: A) Nintedanib; B) S1529 (Hesperadin); and C) CC-401.
Figure 1:
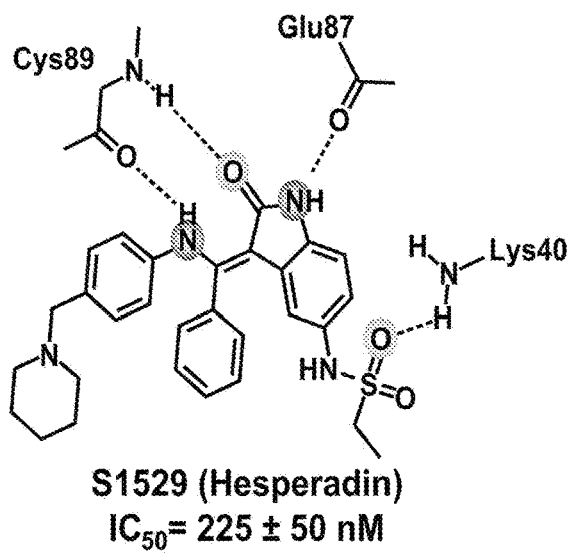
Figure 1:
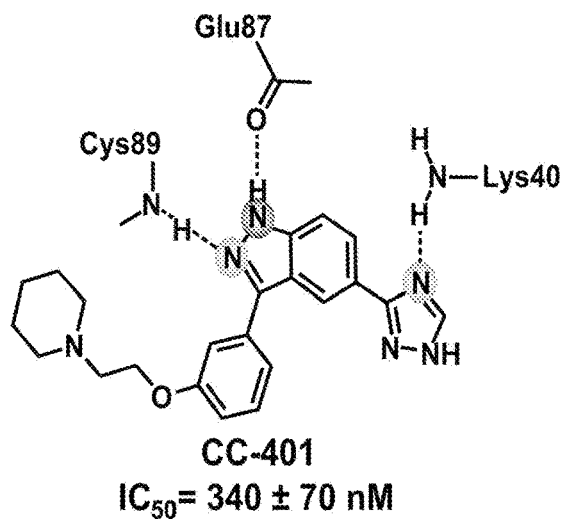

Disclosed herein are indolinone compounds, compositions, and methods for the potent and selective inhibition of maternal embryonic leucine zipper (MELK) kinase. In some embodiments, the present disclosure further relates to indolinone compounds, compositions, and methods for the treatment or prevention of a cancer (for example, triple negative breast cancer).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

Chemical Terminology

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group. In some embodiments, the alkyl comprises 1 to 10 carbon atoms, such as methyl, ethyl, n-propyl, isopropyl, n-butyl, isobutyl, t-butyl, pentyl, hexyl, heptyl, octyl, nonyl, decyl, and the like. The alkyl group can also be substituted or unsubstituted. The alkyl group can be substituted with one or more groups including, but not limited to, alkyl, halogenated alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like. This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, acyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, acyl, aryl, heteroaryl, cycloalkyl, cycloalkenyl, heterocycloalkyl, or heterocycloalkenyl group described above. The term "aminoacyl" specifically refers to an amino group that is substituted with one or more acyl groups, as described below.

The term "carboxylic acid" as used herein is represented by the formula —C(O)OH. A "carboxylate" or "carboxyl" group as used herein is represented by the formula —C(O)O⁻.

The term "ester" as used herein is represented by the formula —$OC(O)Z^1$ or —$C(O)OZ^1$, where $Z^1$ can be an alkyl, halogenated alkyl, alkenyl, alkynyl, acyl, aryl, heteroaryl, cycloalkyl, cycloalkenyl, heterocycloalkyl, or heterocycloalkenyl group described above. The term "aikylester" indicates an alkyl group as defined herein covalently bound to the group it substitutes by an ester linkage. The ester linkage may be in either orientation, e.g., a group of the formula —O(C=O)alkyl or a group of the formula (C=)Oalkyl.

The term "ether" as used herein is represented by the formula $Z^1OZ^2$, where $Z^1$ and $Z^2$ can be, independently, an alkyl, halogenated alkyl, alkenyl, alkynyl, acyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, acyl, aryl, heteroaryl, cycloalkyl, cycloalkenyl, heterocycloalkyl, or heterocycloalkenyl group described above.

The term "acyl" refers to a group of the formula —C(O)$Z^1$, wherein $Z^1$ can be an alkyl, halogenated alkyl, alkenyl, alkynyl, acyl, aryl, heteroaryl, cycloalkyl, cycloalkenyl, heterocycloalkyl, or heterocycloalkenyl group described above. For example, the term "$C_{2-7}$ acyl" as used herein, either alone or in combination with another substituent, means a $C_{1-6}$ alkyl group linked through a carbonyl group such as —C(O)—$C_{1-6}$ alkyl.

The term "amide" or "carboxamide" refers to a group of the formula —C(O)N$Z^1Z^2$ where $Z^1$ and $Z^2$ can be, independently, an alkyl, halogenated alkyl, alkenyl, alkynyl, acyl, aryl, heteroaryl, cycloalkyl, cycloalkenyl, heterocycloalkyl, or heterocycloalkenyl group described above; or together with the nitrogen to which they are bonded, $Z^1$ and $Z^2$ can form a heterocyclic ring.

The term "halide" or "halogen" or "halo" as used herein refers to the fluorine, chlorine, bromine, and iodine.

The term "hydroxyl" or "hydroxy" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, acyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, acyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, and methods, examples of which are illustrated in the accompanying Examples and Figures.

Compounds

In one aspect, disclosed herein is a compound of Formula I:

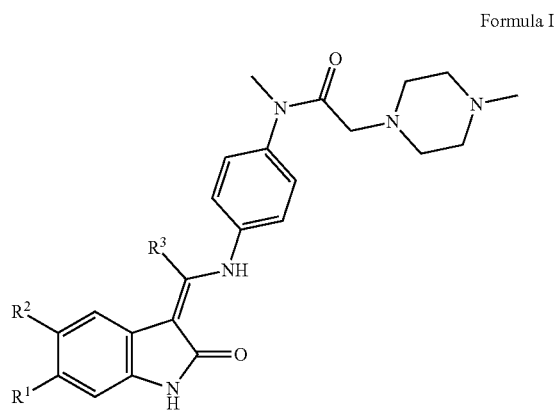

Formula I wherein:

$R^1$ is hydrogen;

$R^2$ is selected from carboxylic acid, ester, amide, acyl, alkoxy, sulfonamide, alkylamino, aminoacyl, or amino; and $R^3$ is selected from aryl or heteroaryl;

or a pharmaceutically acceptable salt thereof.

In another aspect, disclosed herein is a compound of Formula II:

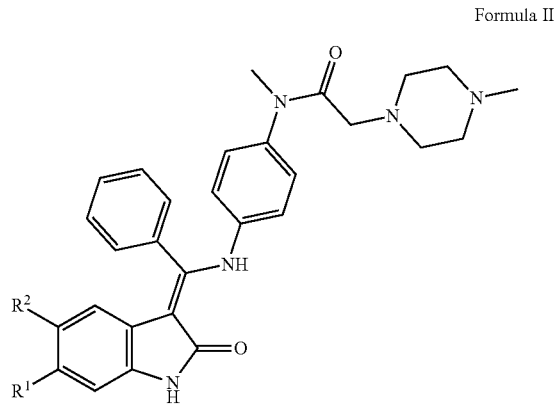

Formula II wherein:

$R^1$ is hydrogen; and $R^2$ is selected from carboxylic acid, ester, amide, acyl, alkoxy, sulfonamide, alkylamino, aminoacyl, or amino;

or a pharmaceutically acceptable salt thereof.

In one aspect, disclosed herein is a compound of Formula III:

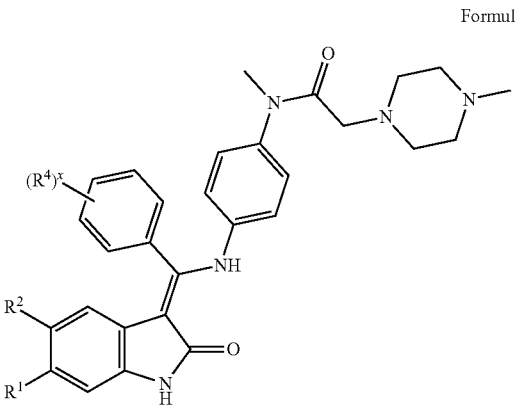

Formula III wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;
R⁵ and R⁶ are independently selected from hydrogen, alkyl, alkylamino, heterocycloalkyl, acyl, or ester; and
x is selected from 1 or 2;
or a pharmaceutically acceptable salt thereof.

In one aspect, disclosed herein is a compound of Formula IV:

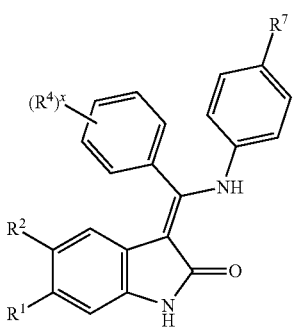

Formula IV wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;
R⁵ and R⁶ are independently selected from hydrogen, alkyl, alkylamino, heterocycloalkyl, acyl, or ester;
R⁷ is selected from NR⁸R⁹, alkyl, alkylamino, heterocycloalkyl, or heterocycloalkylalkyl;
R⁸ and R⁹ are independently selected from hydrogen, alkyl, alkylamino, heterocycloalkyl, heterocycloalkylalkyl, or acyl; and
x is selected from 1 or 2;
or a pharmaceutically acceptable salt thereof.

In one embodiment, R² is unsubstituted. In one embodiment, R² is substituted. In one embodiment, R² is selected from carboxylic acid, ester, amide, acyl, alkoxy, sulfonamide, alkylamino, aminoacyl, or amino. In one embodiment, R² is selected from carboxylic acid, ester, amide, acyl, alkoxy, sulfonamide, alkylamino, aminoacyl, amino, nitro, aryl, or heteroaryl. In one embodiment, R² is ester. In one embodiment, R² is alkylester. In one embodiment, R² is methyl ester. In one embodiment, R² is carboxylic acid. In one embodiment, R² is ester. In one embodiment, R² is amide. In one embodiment, R² is acyl. In one embodiment, R² is sulfonamide. In one embodiment, R² is alkylamino. In one embodiment, R² is aminoacyl. In one embodiment, R² is amino. In one embodiment, R² is nitro. In one embodiment, R² is aryl. In one embodiment, R² is heteroaryl.

In one embodiment, R² is alkoxy. In one embodiment, R² is substituted alkoxy. In one embodiment, R² is alkoxy, wherein the alkoxy is substituted with alkyl, aryl, alkylaryl, cycloalkyl, heterocycloalkyl, cycloalkylalkyl, or heterocycloalkylalkyl.

In one embodiment, R³ is unsubstituted. In one embodiment, R³ is substituted. In one embodiment, R³ is selected from aryl or heteroaryl. In one embodiment, R³ is selected from phenyl, benzyl, pyridine, or furan. In one embodiment, R³ is unsubstituted aryl. In one embodiment, R³ is phenyl. In one embodiment, R³ is substituted aryl. In one embodiment, R³ is substituted aryl, wherein the substituted aryl is an aryl group substituted with alkyl, amino, alkylamino, amide, aminoacyl, hydroxy, alkoxy, aryloxy, carboxylic acid, or ester, or a combination thereof. In one embodiment, R³ is pyridine. In one embodiment, R³ is a pyridine derivative. In one embodiment, R³ is a substituted pyridine. In one embodiment, R³ is furan.

In one embodiment, R³ is unsubstituted heteroaryl. In one embodiment, R³ is substituted heteroaryl. In one embodiment, R³ is substituted heteroaryl, wherein the substituted heteroaryl is a heteroaryl group substituted with alkyl, amino, alkylamino, amide, aminoacyl, hydroxy, alkoxy, aryloxy, carboxylic acid, or ester, or a combination thereof.

In some embodiments, each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶. In some embodiments, two R⁴ come together to form a carbocyclic ring or a heterocyclic ring.

In some embodiments, two R⁴ come together to form an unsubstituted or substituted carbocyclic ring; or an unsubstituted or substituted heterocyclic ring.

In some embodiments, R⁴ is hydrogen. In some embodiments, R⁴ is alkyl. In some embodiments, R⁴ is carboxylic acid. In some embodiments, R⁴ is ester. In some embodiments, R⁴ is amide. In some embodiments, R⁴ is acyl. In some embodiments, $R^4$ is alkoxy. In some embodiments, $R^4$ is hydroxyl. In some embodiments, $R^4$ is hydroxyalkyl. In some embodiments, $R^4$ is sulfonamide In some embodiments, $R^4$ is alkylamino. In some embodiments, $R^4$ is aminoacyl. In some embodiments, $R^4$ is amino. In some embodiments, $R^4$ is nitro. In some embodiments, $R^4$ is heterocycloalkyl. In some embodiments, $R^4$ is heterocycloalkylalkyl. In some embodiments, $R^4$ is $NR^5R^6$.

In some embodiments, $R^5$ and $R^6$ are independently selected from hydrogen, alkyl, alkylamino, heterocycloalkyl, acyl, or ester. In some embodiments, $R^5$ is hydrogen. In some embodiments, $R^5$ is alkyl. In some embodiments, $R^5$ is alkylamino. In some embodiments, $R^5$ is heterocycloalkyl. In some embodiments, $R^5$ is acyl. In some embodiments, $R^5$ is ester. In some embodiments, $R^6$ is hydrogen. In some embodiments, $R^6$ is alkyl. In some embodiments, $R^6$ is alkylamino. In some embodiments, $R^6$ is heterocycloalkyl. In some embodiments, $R^6$ is acyl. In some embodiments, $R^6$ is ester.

In some embodiments, $R^7$ is selected from $NR^8R^9$, alkyl, alkylamino, or heterocycloalkyl. In some embodiments, $R^7$ is $NR^8R^9$. In some embodiments, $R^7$ is alkyl. In some embodiments, $R^7$ is alkylamino. In some embodiments, $R^7$ is heterocycloalkyl.

In some embodiments, $R^8$ and $R^9$ are independently selected from hydrogen, alkyl, alkylamino, heterocycloalkyl, heterocycloalkylalkyl, or acyl. In some embodiments, $R^8$ is hydrogen. In some embodiments, $R^8$ is alkyl. In some embodiments, $R^8$ is alkylamino. In some embodiments, $R^8$ is heterocycloalkyl. In some embodiments, $R^8$ is heterocycloalkylalkyl. In some embodiments, $R^8$ is acyl. In some embodiments, $R^8$ is substituted acyl. In some embodiments, $R^8$ is acyl, wherein the acyl is substituted with hydrogen, alkyl, alkylamino, heterocycloalkyl, or heterocycloalkylalkyl. In some embodiments, $R^9$ is hydrogen. In some embodiments, $R^9$ is alkyl. In some embodiments, $R^9$ is alkylamino. In some embodiments, $R^9$ is heterocycloalkyl. In some embodiments, $R^9$ is heterocycloalkylalkyl. In some embodiments, $R^9$ is acyl. In some embodiments, $R^9$ is substituted acyl. In some embodiments, $R^9$ is acyl, wherein the acyl is substituted with hydrogen, alkyl, alkylamino, heterocycloalkyl, or heterocycloalkylalkyl.

In some embodiments, x is selected from 1 or 2. In some embodiments, x is 2. In some embodiments, x is 1.

In one embodiment, the compound is

In another embodiment, the compound is

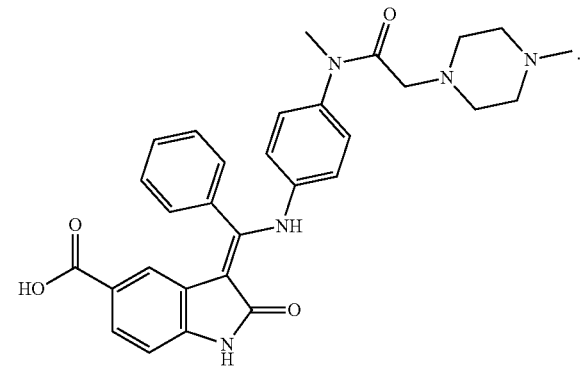 [SMILES: CN1CCN(CC(=O)N(C)c2ccc(N/C(=C3\C(=O)Nc4ccc(C(=O)O)cc43)c3ccccc3)cc2)CC1]

In some embodiments, the compound of Formula I, II, III, or IV is selected from the compounds listed in Table 1.

TABLE 1

Non-limiting examples of compounds of Formula I, II, III, or IV

| Compound | Structure |
|---|---|
| 17 | 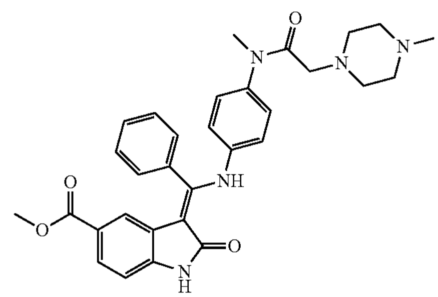 |
| 18 | 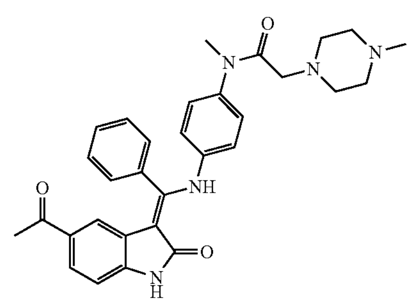 [SMILES: CC(=O)c1ccc2c(c1)/C(=C(/Nc1ccc(N(C)C(=O)CN3CCN(C)CC3)cc1)c1ccccc1)C(=O)N2] |
| 19 | 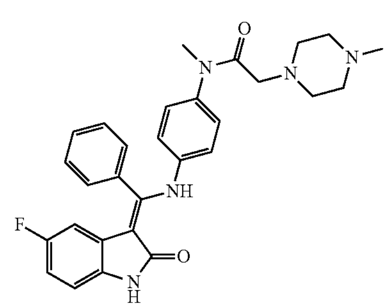 [SMILES: CN1CCN(CC(=O)N(C)c2ccc(N/C(=C3\C(=O)Nc4ccc(F)cc43)c3ccccc3)cc2)CC1] |

TABLE 1-continued
Non-limiting examples of compounds of Formula I, II, III, or IV
| Compound | Structure |
|---|---|
| 21 | 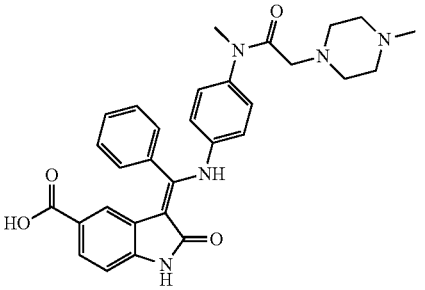 [SMILES: CN1CCN(CC(=O)N(C)c2ccc(N/C(=C3\C(=O)Nc4ccc(C(=O)O)cc43)c3ccccc3)cc2)CC1] |
| 24 | 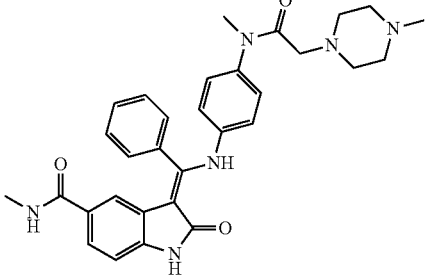 |
| 25 | 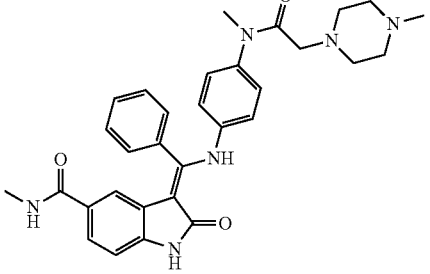 |
In some embodiments, the compound of Formula I, II, III, or IV is selected from the compounds listed in Table 2.
TABLE 2
Additional non-limiting examples of compounds of Formula I, II, III, or IV
| Table 2 Structure No. | Structure |
|---|---|
| 91 | 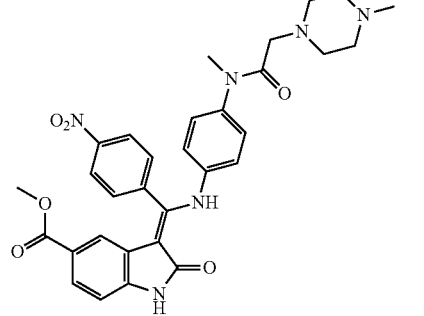 |
| 92 | 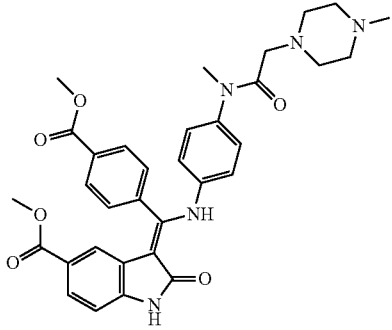 [SMILES: COC(=O)c1ccc(/C(Nc2ccc(N(C)C(=O)CN3CCN(C)CC3)cc2)=C2/C(=O)Nc3ccc(C(=O)OC)cc32)cc1] |
| 93 | 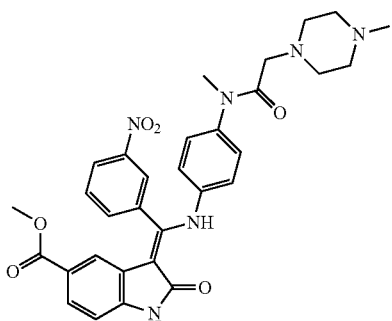 |
| 94 | 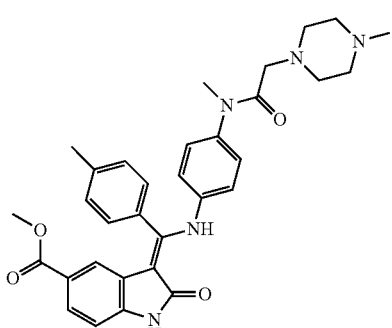 |
| 95 | 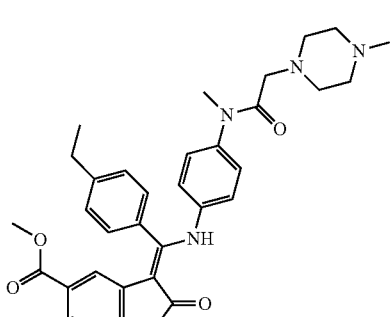 |

TABLE 2-continued
Additional non-limiting examples of compounds of Formula I, II, III, or IV
| Table 2 Structure No. | Structure |
|---|---|
| 96 | 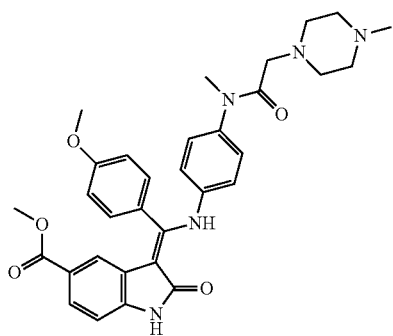 [SMILES: COC(=O)c1ccc2c(c1)/C(=C(/Nc1ccc(N(C)C(=O)CN3CCN(C)CC3)cc1)c1ccc(OC)cc1)C(=O)N2] |
| 97 | 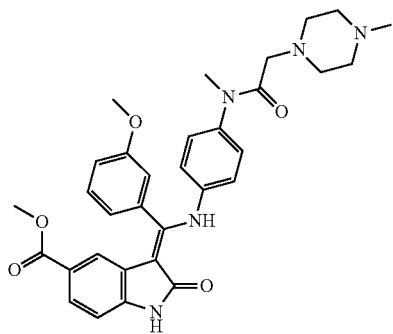 [SMILES: COC(=O)c1ccc2c(c1)/C(=C(/Nc1ccc(N(C)C(=O)CN3CCN(C)CC3)cc1)c1cccc(OC)c1)C(=O)N2] |
| 98 | 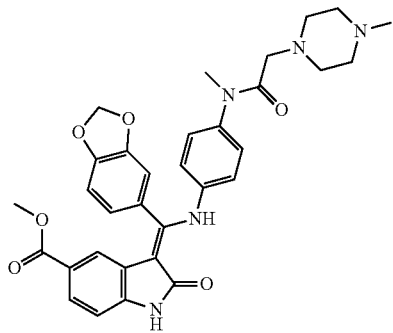 [SMILES: COC(=O)c1ccc2c(c1)/C(=C(/Nc1ccc(N(C)C(=O)CN3CCN(C)CC3)cc1)c1ccc3c(c1)OCO3)C(=O)N2] |
| 100 | 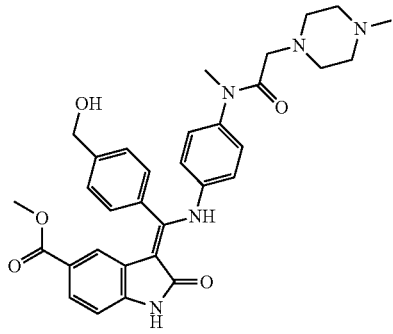 [SMILES: COC(=O)c1ccc2c(c1)/C(=C(/Nc1ccc(N(C)C(=O)CN3CCN(C)CC3)cc1)c1ccc(CO)cc1)C(=O)N2] |
| 102 | 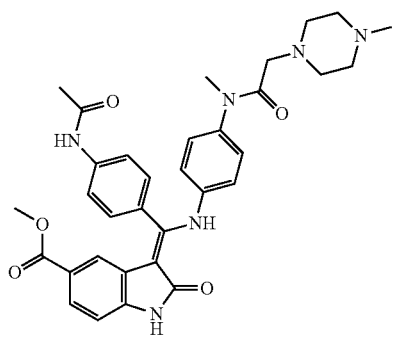 [SMILES: COC(=O)c1ccc2c(c1)/C(=C(/Nc1ccc(N(C)C(=O)CN3CCN(C)CC3)cc1)c1ccc(NC(C)=O)cc1)C(=O)N2] |
| 103 | 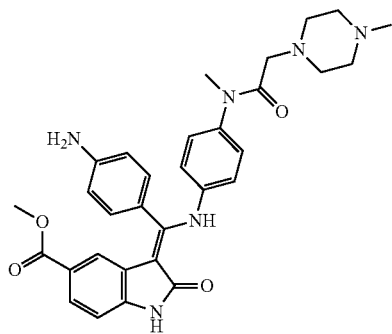 |
| 104 | 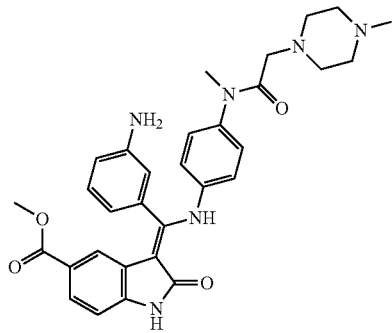 [SMILES: COC(=O)c1ccc2c(c1)/C(=C(/Nc1ccc(N(C)C(=O)CN3CCN(C)CC3)cc1)c1cccc(N)c1)C(=O)N2] |
| 105 | 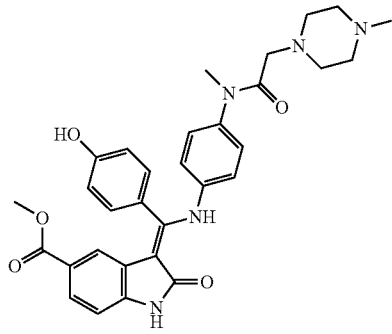 [SMILES: COC(=O)c1ccc2c(c1)/C(=C(/Nc1ccc(N(C)C(=O)CN3CCN(C)CC3)cc1)c1ccc(O)cc1)C(=O)N2] |

TABLE 2-continued
Additional non-limiting examples of compounds of Formula I, II, III, or IV
| Table 2 Structure No. | Structure |
|---|---|
| 106 | 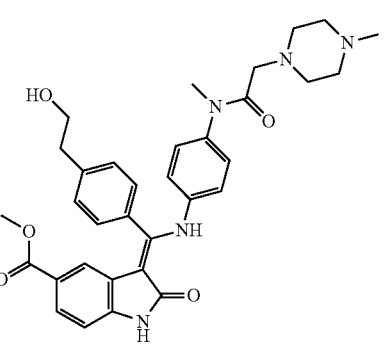 |
| 107 | 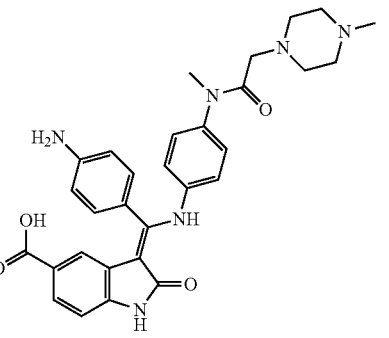 |
| 108 | 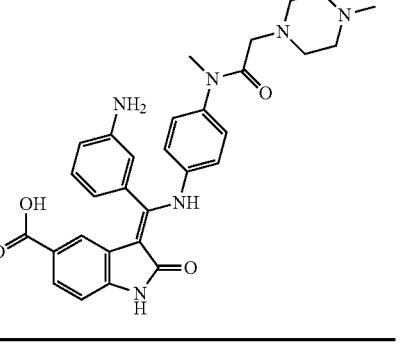 |
TABLE 3
Additional non-limiting examples of compounds of Formula I, II, III, or IV
| Table 3 Structure No. | Structure |
|---|---|
| 109 | 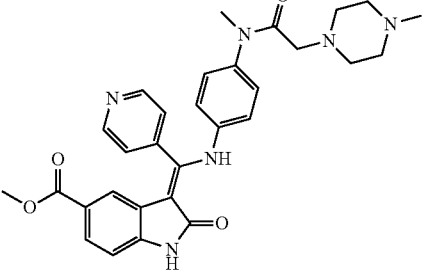 |
| 110 | 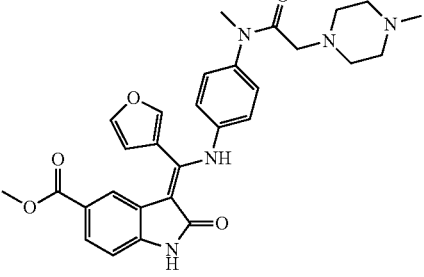 |
| 111 | 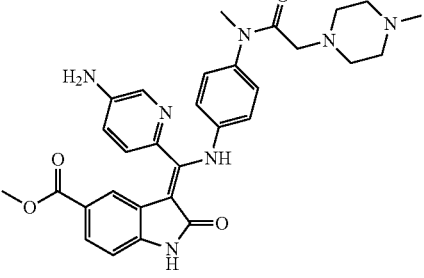 |
| 112 | 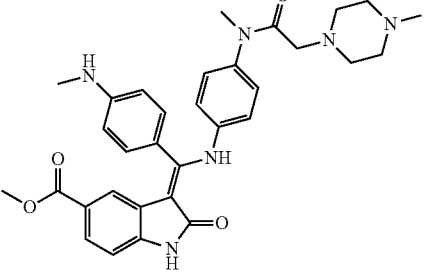 |
| 113 | 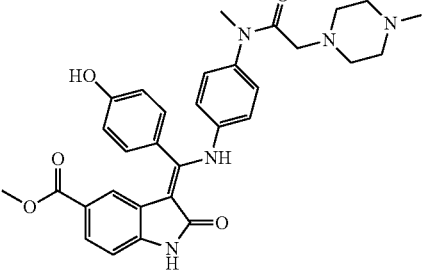 |
In some embodiments, the compound of Formula I, II, III, or IV is selected from the compounds listed in Table 3.

TABLE 3-continued
Additional non-limiting examples of compounds of Formula I, II, III, or IV
| Table 3 Structure No. | Structure |
|---|---|
| 114 | 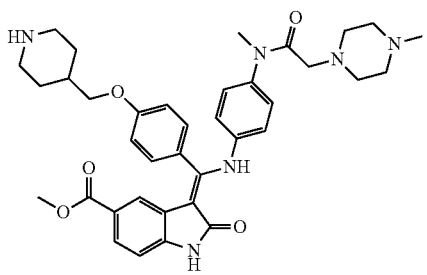 [SMILES: COC(=O)c1ccc2c(c1)/C(=C(/Nc1ccc(N(C)C(=O)CN3CCN(C)CC3)cc1)c1ccc(OCC3CCNCC3)cc1)C(=O)N2] |
| 115 | 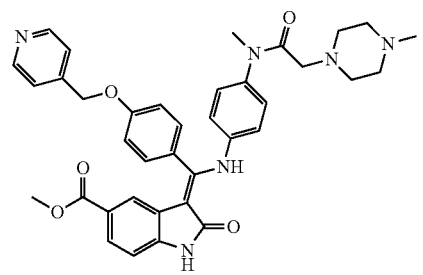 [SMILES: COC(=O)c1ccc2c(c1)/C(=C(/Nc1ccc(N(C)C(=O)CN3CCN(C)CC3)cc1)c1ccc(OCc3ccncc3)cc1)C(=O)N2] |
| 116 | 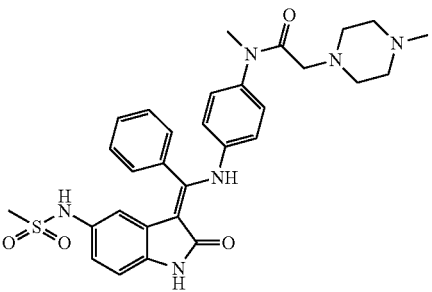 |
| 117 | 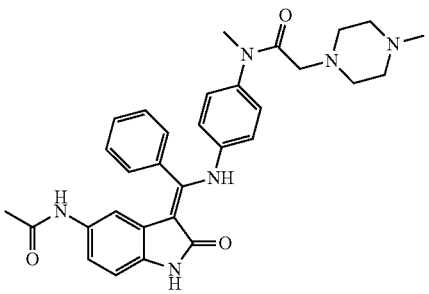 [SMILES: CC(=O)Nc1ccc2c(c1)/C(=C(/Nc1ccc(N(C)C(=O)CN3CCN(C)CC3)cc1)c1ccccc1)C(=O)N2] |
| 118 | 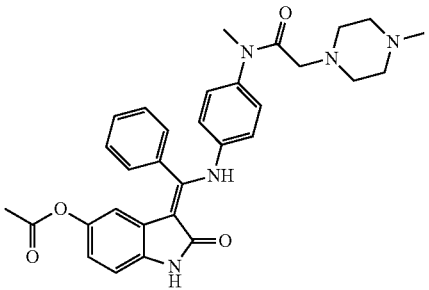 [SMILES: CC(=O)Oc1ccc2c(c1)/C(=C(/Nc1ccc(N(C)C(=O)CN3CCN(C)CC3)cc1)c1ccccc1)C(=O)N2] |
| 119 | 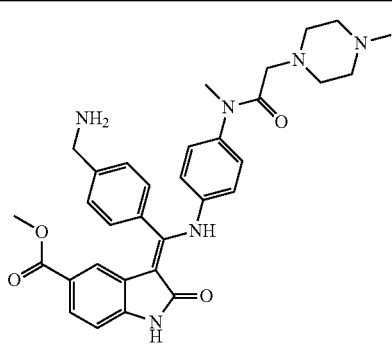 |
| 120 | 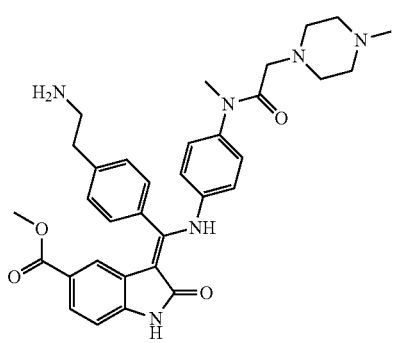 [SMILES: COC(=O)c1ccc2c(c1)/C(=C(/Nc1ccc(N(C)C(=O)CN3CCN(C)CC3)cc1)c1ccc(CCN)cc1)C(=O)N2] |
| 121 | 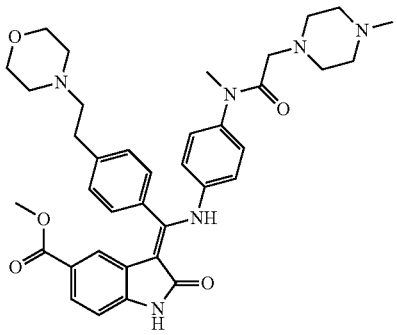 [SMILES: COC(=O)c1ccc2c(c1)/C(=C(/Nc1ccc(N(C)C(=O)CN3CCN(C)CC3)cc1)c1ccc(CCN3CCOCC3)cc1)C(=O)N2] |
| 122 | 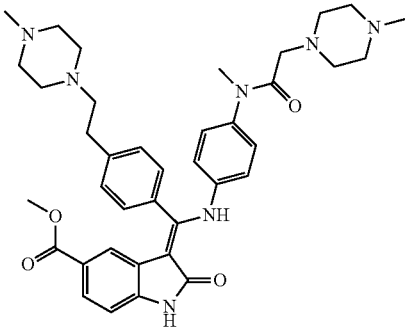 |

TABLE 3-continued
Additional non-limiting examples of compounds of Formula I, II, III, or IV
| Table 3 Structure No. | Structure |
|---|---|
| 123 | 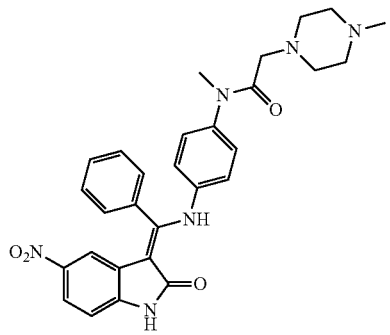 |
| 124 | 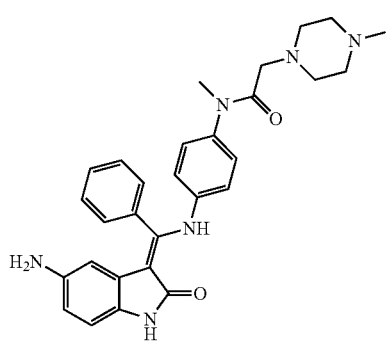 [SMILES: CN1CCN(CC(=O)N(C)c2ccc(N/C(=C3\C(=O)Nc4ccc([N+](=O)[O-])cc43)c3ccccc3)cc2)CC1] |
| 125 | 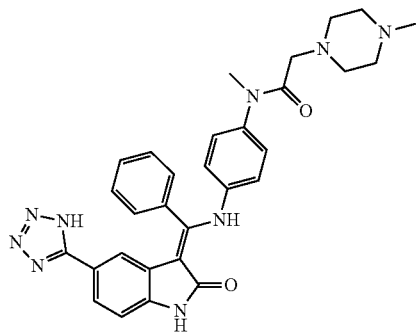 [SMILES: CN1CCN(CC(=O)N(C)c2ccc(N/C(=C3\C(=O)Nc4ccc(-c5nnn[nH]5)cc43)c3ccccc3)cc2)CC1] |
| 126 | 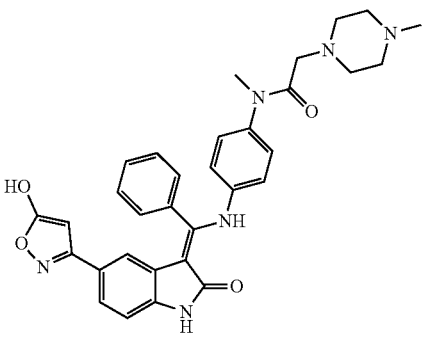 [SMILES: CN1CCN(CC(=O)N(C)c2ccc(N/C(=C3\C(=O)Nc4ccc(-c5cc(O)on5)cc43)c3ccccc3)cc2)CC1] |
| 127 | 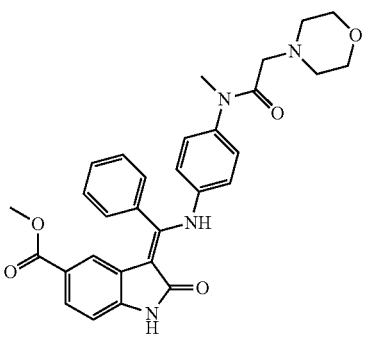 [SMILES: COC(=O)c1ccc2c(c1)/C(=C(/Nc1ccc(N(C)C(=O)CN3CCOCC3)cc1)c1ccccc1)C(=O)N2] |
| 128 | 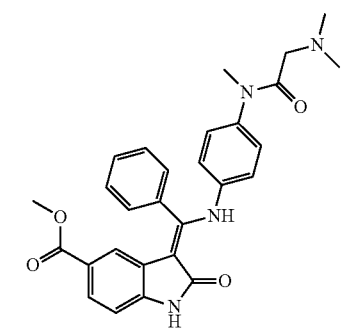 [SMILES: COC(=O)c1ccc2c(c1)/C(=C(/Nc1ccc(N(C)C(=O)CN(C)C)cc1)c1ccccc1)C(=O)N2] |
| 129 | 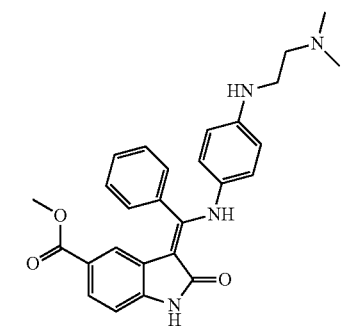 [SMILES: COC(=O)c1ccc2c(c1)/C(=C(/Nc1ccc(NCCN(C)C)cc1)c1ccccc1)C(=O)N2] |
| 130 | 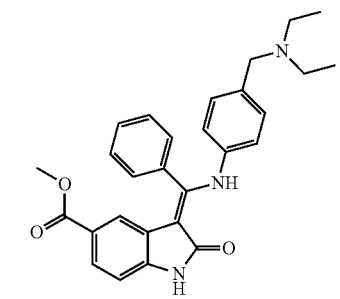 [SMILES: CCN(CC)Cc1ccc(N/C(=C2\C(=O)Nc3ccc(C(=O)OC)cc32)c2ccccc2)cc1] |

TABLE 3-continued

Additional non-limiting examples of
compounds of Formula I, II, III, or IV

Table 3

| Structure No. | Structure |
|---|---|
| 131 | 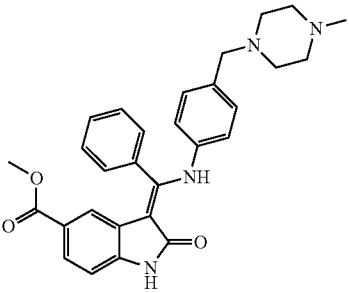 [SMILES: COC(=O)c1ccc2c(c1)/C(=C(/Nc1ccc(CN3CCN(C)CC3)cc1)c1ccccc1)C(=O)N2] |
| 132 | 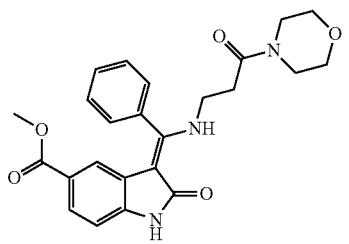 [SMILES: COC(=O)c1ccc2c(c1)/C(=C(/NCCC(=O)N1CCOCC1)c1ccccc1)C(=O)N2] |

In some embodiments, the compound is:

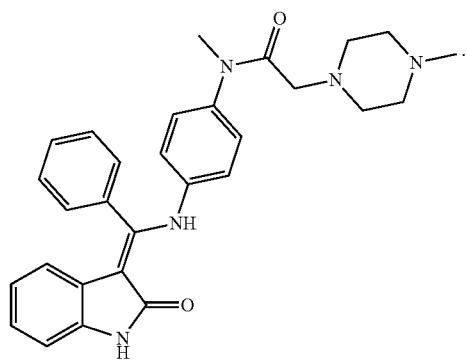 [SMILES: CN1CCN(CC(=O)N(C)c2ccc(N/C(=C3\C(=O)Nc4ccccc43)c3ccccc3)cc2)CC1]

Methods

In one aspect, provided herein is a method for the treatment of a cancer, comprising: administering an effective amount of a compound of Formula I to a host in need thereof:

Formula I

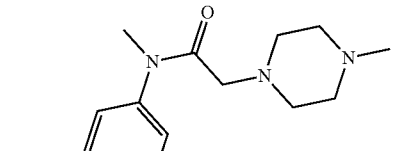

wherein:

$R^1$ is hydrogen;

$R^2$ is selected from carboxylic acid, ester, amide, acyl, alkoxy, sulfonamide, alkylamino, aminoacyl, or amino; and $R^3$ is selected from aryl or heteroaryl;

or a pharmaceutically acceptable salt thereof.

In another aspect, provided herein is a method for the treatment of a cancer, comprising: administering an effective amount of a compound of Formula II to a host in need thereof:

Formula II

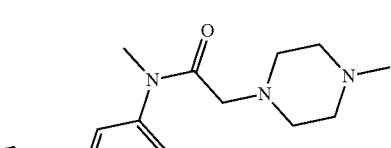

wherein:

$R^1$ is hydrogen; and $R^2$ is selected from carboxylic acid, ester, amide, acyl, alkoxy, sulfonamide, alkylamino, aminoacyl, or amino;

or a pharmaceutically acceptable salt thereof.

In one aspect, provided herein is a method for the treatment of a cancer, comprising: administering an effective amount of a compound of Formula III to a host in need thereof:

Formula III

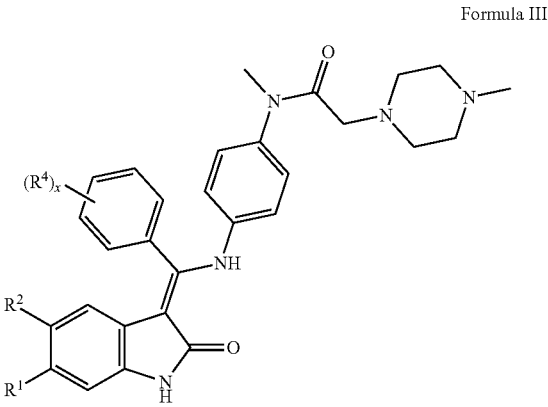

wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;
R⁵ and R⁶ are independently selected from hydrogen, alkyl, alkylamino, heterocycloalkyl, acyl, or ester; and
x is selected from 1 or 2;
or a pharmaceutically acceptable salt thereof.

In one aspect, provided herein is a method for the treatment of a cancer, comprising: administering an effective amount of a compound of Formula IV to a host in need thereof:

Formula IV

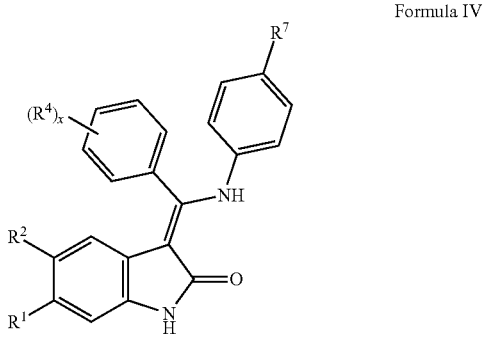

wherein:
R¹ is hydrogen;
R² is selected from carboxylic acid, ester, amide, acyl, alkoxy, sulfonamide, alkylamino, aminoacyl, amino, nitro, aryl, or heteroaryl;
each R⁴ is independently selected from hydrogen, alkyl, carboxylic acid, ester, amide, acyl, alkoxy, hydroxyl, hydroxyalkyl, sulfonamide, alkylamino, aminoacyl, amino, nitro, heterocycloalkyl, heterocycloalkylalkyl, or NR⁵R⁶; or
two R⁴ come together to form a carbocyclic ring or a heterocyclic ring;
R⁵ and R⁶ are independently selected from hydrogen, alkyl, alkylamino, heterocycloalkyl, acyl, or ester;
R⁷ is selected from NR⁸R⁹, alkyl, alkylamino, heterocycloalkyl, or heterocycloalkylalkyl;
R⁸ and R⁹ are independently selected from hydrogen, alkyl, alkylamino, heterocycloalkyl, heterocycloalkylalkyl, or acyl; and
x is selected from 1 or 2;
or a pharmaceutically acceptable salt thereof.

In one embodiment, the cancer is selected from triple negative breast cancer or glioblastoma multiforme. In one embodiment, the cancer is triple negative breast cancer. In one embodiment, the cancer is glioblastoma multiforme.

In some embodiments, the methods described herein are used for the treatment of the prevention of a cancer, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including triple negative breast cancer (TNBC), ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In one embodiment of the above methods, the compound administered is:

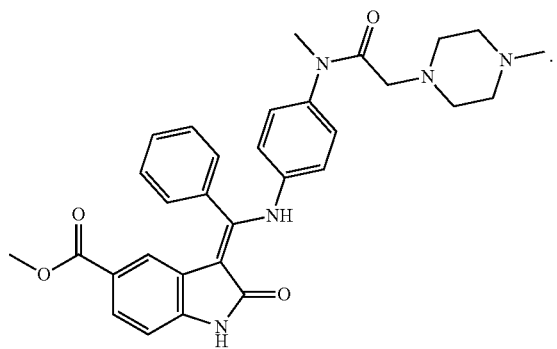

In another embodiment of the above methods, the compound administered is:

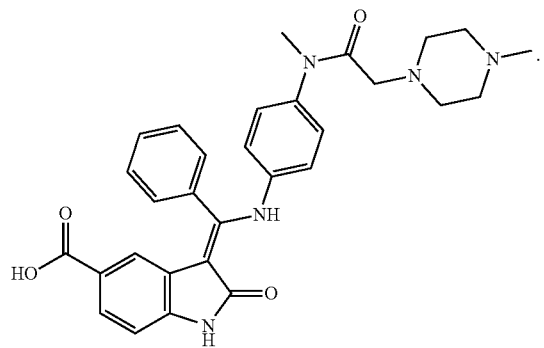 [SMILES: CN1CCN(CC(=O)N(C)c2ccc(N/C(=C3\C(=O)Nc4ccc(C(=O)O)cc43)c3ccccc3)cc2)CC1]

In another aspect, provided herein is a method for the treatment of a cancer, comprising: administering an effective amount of a compound to a host in need thereof, wherein the compound is:

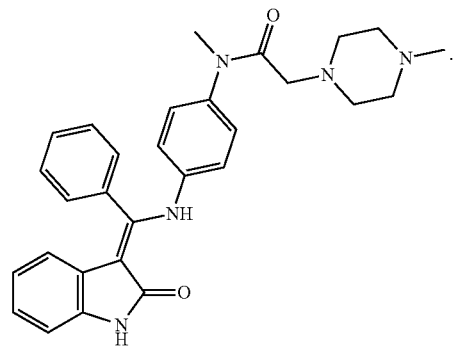 [SMILES: CN1CCN(CC(=O)N(C)c2ccc(N/C(=C3\C(=O)Nc4ccccc43)c3ccccc3)cc2)CC1]

Combinations Therapies—Additional Chemotherapeutic Agents

In one embodiment, a compound of Formula I, II, III, or IV is administered in combination with an additional chemotherapeutic agent. In one embodiment, disclosed herein is a composition comprising a compound of Formula I and an additional chemotherapeutic agent. In one embodiment, disclosed herein is a composition comprising a compound of Formula II and an additional chemotherapeutic agent. In one embodiment, disclosed herein is a composition comprising a compound of Formula III and an additional chemotherapeutic agent. In one embodiment, disclosed herein is a composition comprising a compound of Formula IV and an additional chemotherapeutic agent.

Additional chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional chemotherapeutic agents or therapeutic agents that can be administered in combination with the compounds disclosed herein can include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

Compositions

Compositions, as described herein, comprising an active compound and an excipient of some sort may be useful in a variety of applications. For example, pharmaceutical compositions comprising an active compound and an excipient may be useful for the treatment or prevention of a cancer, for example, triple negative breast cancer.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylc arboxymethylcellulo se (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Potent and Selective Indolinone Derivatives that Inhibit Maternal Embryonic Leucine Zipper Kinase (MELK) and Inhibit Triple Negative Breast Cancer (TNBC) Cell Growth Despite recent advances in molecularly directed therapy, triple negative breast cancer (TNBC) remains one of the most aggressive forms of breast cancer still without a suitable target for specific inhibitors. Maternal embryonic leucine zipper kinase (MELK) is highly expressed in TNBC where the level of overexpression correlates with poor prognosis and an aggressive disease course. This example describes the identification of a series of ATP-competitive indolinone derivatives with subnanomolar inhibition constants towards MELK. The most potent compound inhibits the proliferation of TNBC cells and exhibits a selectivity for cells expressing high levels of MELK.

In contrast to most members of the AMPK-RK family, which mediate cell survival under stressful metabolic conditions (Gil M, et al. Gene. 1997; 195(2):295-301; Beullens M, et al. The Journal of biological chemistry. 2005; 280 (48):40003-40011). MELK has been implicated in multiple cellular processes, including cell cycle checkpoint regulation (Blot J, et al. Dev Biol. 2002; 241(2):327-338; Davezac N, et al. Oncogene. 2002; 21(50):7630-7641), proliferation (Joshi K, et al. Stem cells (Dayton, Ohio). 2013; Saito R, et al. Cancer science. 2012; 103(1):42-49), apoptosis (Lin M L, et al. Breast cancer research: BCR. 2007; 9(1):R17; Pickard M R, et al. Biochimica et biophysic a acta. 2011; 1812(9): 1146-1153), and RNA processing (Vulsteke V, et al. The Journal of biological chemistry. 2004; 279(10):8642-8647). MELK is expressed in the early stages of murine embryonic development (Heyer B S, et al. Molecular reproduction and development. 1997; 47(2):148-156), but MELK knockout mice develop normally with no obvious pathologic phenotype, suggesting that MELK's developmentally-related functions may be redundant (Wang Y, et al. eLife. 2014: e01763). Yet despite its apparent dispensable nature in differentiated adult cells, evidence has implicated MELK's importance in proliferating progenitor populations, including multipotent neural progenitors (Nakano I, et al. The Journal of cell biology. 2005; 170(3):413-427), myoblasts (Niesler C U, et al. Experimental physiology. 2007; 92(1): 207-217), and mammary progenitors (Hebbard L W, et al. Cancer research. 2010; 70(21):8863-8873). Interestingly, MELK inhibition does not affect survival in normal neural stem cells, but siRNA-mediated MELK knockdown induces apoptosis selectively in glioma stem cells (Nakano I, et al. Neuro-oncology. 2011; 13(6):622-634; Nakano I, et al. *Journal of neuroscience research.* 2008; 86(1):48-60). Such data reinforces the redundancy of MELK function in noncancerous cells, but also implicates the existence of an exploitable target in certain cancer stem cell populations.

In addition to its putative role in cancer stem cells, upregulated MELK mRNA and protein levels have been observed in a wide array of cancer cell types and clinical tumor samples (Gray D, et al. Cancer research. 2005; 65(21):9751-9761; Ryu B, et al. PloS one. 2007; 2(7):e594; Marie S K, et al. International journal of cancer. Journal international du cancer. 2008; 122(4):807-815; Li Y, et al. Lung cancer (Amsterdam, Netherlands). 2013; Li Y, et al. Lung cancer (Amsterdam, Netherlands). 2013; Rajkumar T, et al. BMC cancer. 2011; 11:80; Risinger J I, et al. Frontiers in oncology. 2013; 3:139). Of particular note is the fact that MELK expression correlates with poor prognosis in the most aggressive subsets of disease, including glioblastoma multiforme (GBM) (Nakano I, et al. Journal of neuroscience research. 2008; 86(1):48-60; Marie S K, et al. International journal of cancer. Journal international du cancer. 2008; 122(4):807-815; Kappadakunnel M, et al. Journal of neuro-oncology. 2010; 96(3):359-367) and triple negative breast cancer (TNBC) (Wang Y, et al. eLife. 2014: e01763; Komatsu M, et al. International journal of oncology. 2013; 42(2):478-506; Al-Ejeh F, et al. Oncogenesis. 2014; 3:e100). Factors contributing to poor outlook for TNBC patients in part stems from the cancer's ability not only to proliferate quickly, but also its propensity to spread and recur in distant organs. From a molecular biology perspective, mounting evidence continues to implicate MELK in direct and transcriptional regulation of cell division in the context of malignancy (Joshi K, et al. Stem cells (Dayton, Ohio). 2013; Wang Y, et al. eLife. 2014: e01763; Marie S K, et al. Proteome Sci. 2016; 14:6). Furthermore, MELK has also been preliminarily linked to metastasis through its involvement with TGF-ß driven epithelial-to-mesenchymal transition (EMT) (Seong H A, et al. The Journal of biological chemistry. 2010; 285(40):30959-30970). The cancer-specific expression pattern, combined with the clinical and biological data have therefore justifiably fostered strong interest in MELK as a clinical target.

The present example discloses novel chemical probes to inhibit MELK and small molecule therapeutics that can target a cancer (for example, TNBC). To that end, the design and development of a new structural class of highly potent indolinone MELK inhibitors is described in this example, including compounds 16, 17, and 21, with subnanomolar inhibition constants ($K_i$). In addition to potency, the new class of inhibitors disclosed herein show selectivity for MELK relative to other functionally and evolutionarily related kinases. Finally, these inhibitors were applied to relevant TNBC cell lines. It was observed that the inhibitors impact TNBC cell viability and proliferation, with little effect on an immortalized breast epithelial cell line which does not express high levels of MELK.

Over the last two decades, protein kinases have represented a major field for drug development. As such, diverse methods of kinase inhibitor discovery have emerged and have been extensively employed in both the industrial and academic settings. Target-centric strategies focus on screening small molecule libraries against a single kinase of interest, whereas compound-centric approaches profile activities of a single compound against the entire kinome (Miduturu C V, et al. Chemistry & biology. 2011; 18(7): 868-879). Within the target-centric method, screening libraries may take on the form of fragment-based, directed, or diverse high-throughput compound collections.

In addition to addressing selectivity, cross-screening has become increasingly utilized as a means of drug discovery. Cross-screening unearths off-target effects in cases where inhibitory properties of the small molecules are characterized (e.g. single known kinase inhibitor or directed kinase inhibitor libraries) (Uitdehaag J C, et al. Br J Pharmacol. 2012; 166(3):858-876). Such off-target activity then serves as an initial starting point for development of untargeted or under targeted kinase inhibitors (Mathea S, et al. *ACS Chem Biol.* 2016; 11(6):1595-1602; Elkins J M, et al. Nat Biotechnol. 2016; 34(1):95-103). Alternatively, compound-centric approaches may also be used to improve selectivity of the primary compound, engineering out inhibition of particular undesired targets (Mathea S, et al. *ACS Chem Biol.* 2016). In each of the above strategies, structural guidance is typically essential at every stage to provide critical insight for scaffold modification.

To date, no inhibitors developed with MELK as a primary target are FDA approved. Thus, as an initial experiment, a curated library of approximately 800 known kinase inhibitors in duplicate plate format was examined for ability to inhibit MELK as an off-target. Compounds were ranked according to average percent inhibition at both 10 and 1 µM, revealing 18 compounds with ≥50% inhibition at 1 µM. The ten most potent compounds were further characterized by determining each compound's respective $IC_{50}$ (Table 4). The indolinone scaffold or a similar bicyclic core structure populated the top hits. Indeed, indolinone motifs represent a common pharmacophore in ATP-competitive inhibitors (Prakash C R, et al. Mini reviews in medicinal chemistry. 2012; 12(2):98-119; Aronov A M, et al. Journal of medicinal chemistry. 2008; 51(5): 1214-1222).

TABLE 4

| Cross-inhibition of MELK by known kinase inhibitors | | | |
|---|---|---|---|
| Compound | Structure | Core | $IC_{50}$ ± SE (nM) |
| Nintedanib | | Indolinone | 43 ± 3.4 |

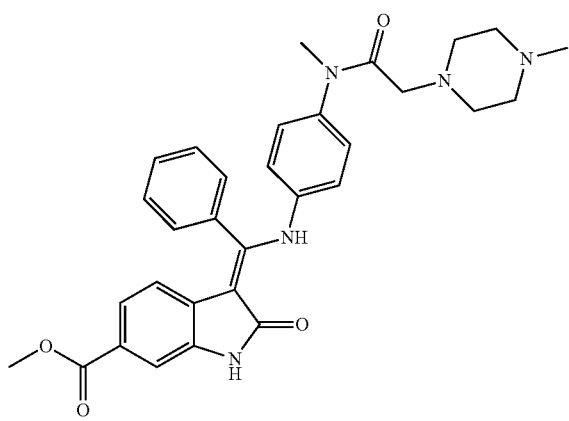

TABLE 4-continued

Cross-inhibition of MELK by known kinase inhibitors

| Compound | Structure | Core | IC$_{50}$ ± SE (nM) |
|---|---|---|---|
| Hesperadin | 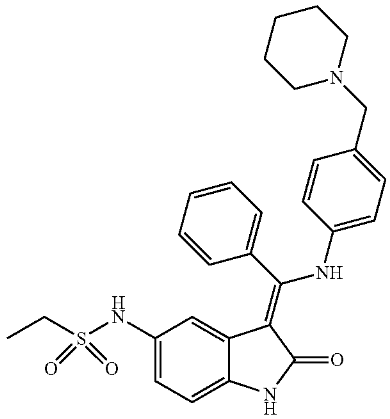 [SMILES: CCS(=O)(=O)Nc1ccc2c(c1)/C(=C(/Nc1ccc(CN3CCCCC3)cc1)c1ccccc1)C(=O)N2] | Indolinone | 225 ± 50 |
| 420099 | 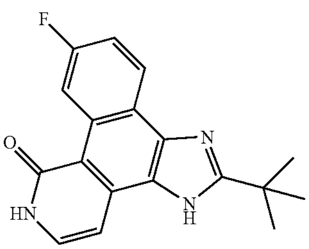 [SMILES: CC(C)(C)c1nc2c3ccc(F)cc3c3c(=O)[nH]ccc3c2[nH]1] | Benzimidazo-isoquinolinone | 330 ± 37 |
| CC401 | 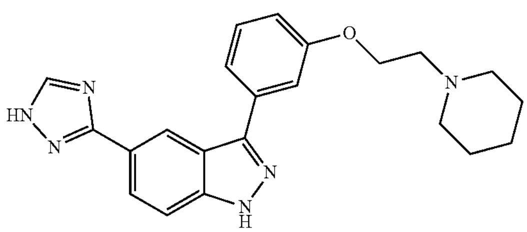 [SMILES: c1cc(OCCN2CCCCC2)cc(-c2n[nH]c3ccc(-c4nc[nH]n4)cc23)c1] | Indazole | 340 ± 70 |
| PIK75 | 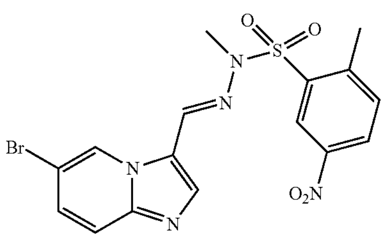 | Imidazopyridine | 400 ± 72 |
| HA-1004 | 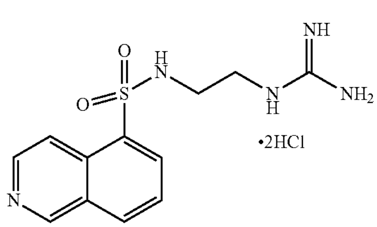 [SMILES: N=C(N)NCCNS(=O)(=O)c1cccc2cnccc12] | Isoquinoline | 440 ± 210 |

TABLE 4-continued

Cross-inhibition of MELK by known kinase inhibitors

| Compound | Structure | Core | IC$_{50}$ ± SE (nM) |
|---|---|---|---|
| AT9283 | 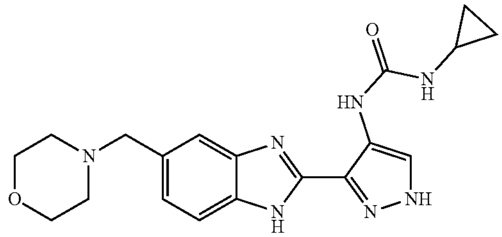 [SMILES: O=C(Nc1c[nH]nc1-c1nc2cc(CN3CCOCC3)ccc2[nH]1)NC1CC1] | Benzimidazole | 685 ± 125 |
| 527450 | 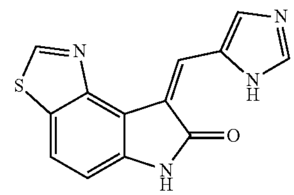 [SMILES: O=C1Nc2ccc3scnc3c2/C1=C/c1cnc[nH]1] | Indolinone | 720 ± 100 |
| 572660 | 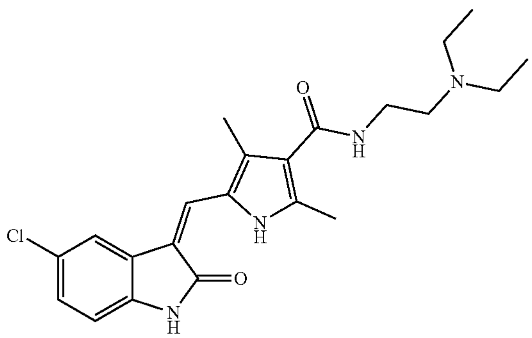 [SMILES: CCN(CC)CCNC(=O)c1c(C)[nH]c(/C=C2\C(=O)Nc3ccc(Cl)cc32)c1C] | Indolinone | 760 ± 190 |
| AZD776 | 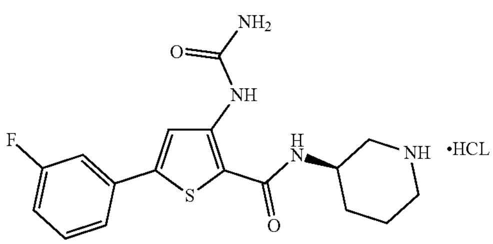 [SMILES: NC(=O)Nc1cc(-c2cccc(F)c2)sc1C(=O)N[C@@H]1CCCNC1] | Thiofuran | 900 ± 91 |

The most potent of the top inhibitor candidates was nintedanib (BIBF-1120, Vargatef®/Ofev®), which displayed an IC$_{50}$ of 43 nM. Nintedanib is already FDA-approved for the treatment of idiopathic pulmonary fibrosis and is currently undergoing clinical trials for treatment of non-small cell lung cancer, metastatic colorectal cancer, and ovarian cancer. However, it is a multi-kinase inhibitor whose primary described mechanism of action is inhibition of the growth factor receptors VEGFR, PDGFR, and FGFR. To improve upon nintedanib's potency and selectivity towards MELK, a medicinal chemistry program was designed around its structural features, using the indolinone core as a primary scaffold.

While nintedanib was clearly the most potent molecule, (IC$_{50}$=43 nM), additional observations from the screen also directed the medicinal chemistry design strategy. The top three most potent inhibitors all exhibit a common alternating donor/acceptor hydrogen-bonding pattern that has also been observed with previously published inhibitors (FIG. 1). Heteroatoms and substituents of the bicyclic core are spatially oriented to interact with both the hinge region and the conserved catalytic lysine, respectively. In addition to nintedanib, an indolinone scaffold forms the core of three other candidate compounds (Table 4, entries 2, 8, and 9), while others contained similar heterocyclic motifs. Notably, several of the indolinones contain substituents at the 5- or 6-position, which are predicted through modeling studies to interact via hydrogen bonding with Lys 40 of the binding pocket.

Figure 2:
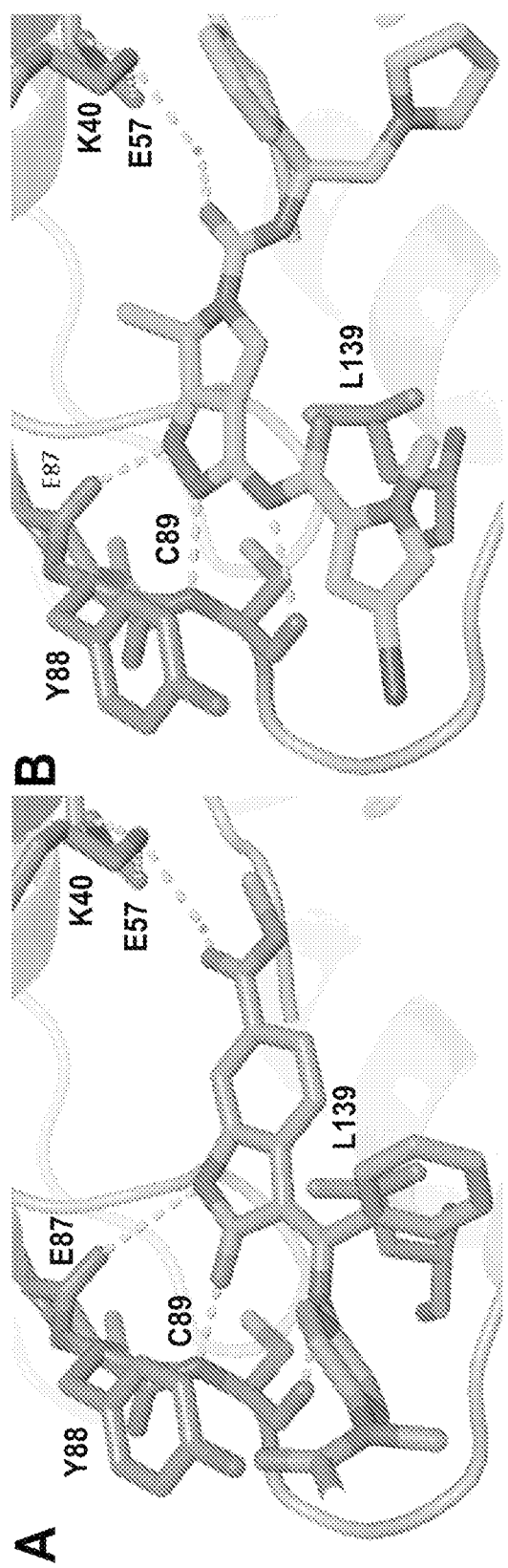
FIG. 2 shows the molecular interactions between nintedanib and Cpd2 with MELK. Molecular modeling studies were performed using Gold 5.1 (Cambridge Crystallographic Data Center). A) Docking of nintedanib ($IC_{50}$~43 nM) into the ATP-binding site of the MELK conformation PDB 4BKY. B) Crystal structure of a benzodipyrazole inhibitor (Cpd2) in complex with the MELK catalytic domain (PDB: 4BKZ).

Molecular modeling studies using Gold 5.1 (Cambridge Crystallographic Data Center) reinforce the similarities in binding pose and electrostatic contacts between nintedanib and other published inhibitors (FIG. 2). In the hinge region, the backbone of C89 interacts with the enamine nitrogen and the carbonyl of the indolinone ring of nintedanib (FIG. 2A), mirroring the hydrogen bonding pattern seen in the crystal structure of MELK with Cpd2 (FIG. 2B, PDB 4BKY) (Canevari G, et al. Biochemistry. 2013; 52(37):6380-6387). With both nintedanib and Cpd2, K40 is positioned to interact with bicyclic core substituents, either directly or via a water molecule. Interaction with K40 has been previously described as an "activity cliff" with other MELK inhibitors, in that loss of this interaction results in loss of compound activity towards MELK (Toure B B, et al. J Med Chem. 2016; 59(10):4711-4723; Furtmann N, et al. J Med Chem. 2015; 58(1):252-264). Taken together, the screening and modeling data suggest that MELK not only accommodates various substituents at the 5th and 6th positions of the indolinone ring, but also that it may be a critical element for maintaining inhibitor potency. Thus, a derivative library incorporating 5- and 6-substituted indolinone inhibitors was synthesized.

Synthesis of 5, or 6-Substituted Indolinone Derivatives 15-25

After identifying the MELK inhibitor compounds in Table 4, a number of 5, or 6-substituted indolinone derivatives were then synthesized in order to improve potency and selectivity (See Compounds 15-25). The general synthetic routes are outlined in Schemes 1 and 2. The key intermediates 6-10 were prepared by acylation of indolinones 1-5 and subsequent condensation with ortho-benzoic acid triethylester. Aromatic amine intermediate 14 was prepared by literature procedures as illustrated in Scheme 1 (Roth G J, et al. J Med Chem. 2009; 52(14):4466-4480). Acylation of N-methyl-4-nitroaniline 11 gave chloroactyl amide 12, which was then treated with N-methylpiperazine to displace chloride; followed by catalytic reduction of the nitro group which gave the key aromatic amine intermediate 14.

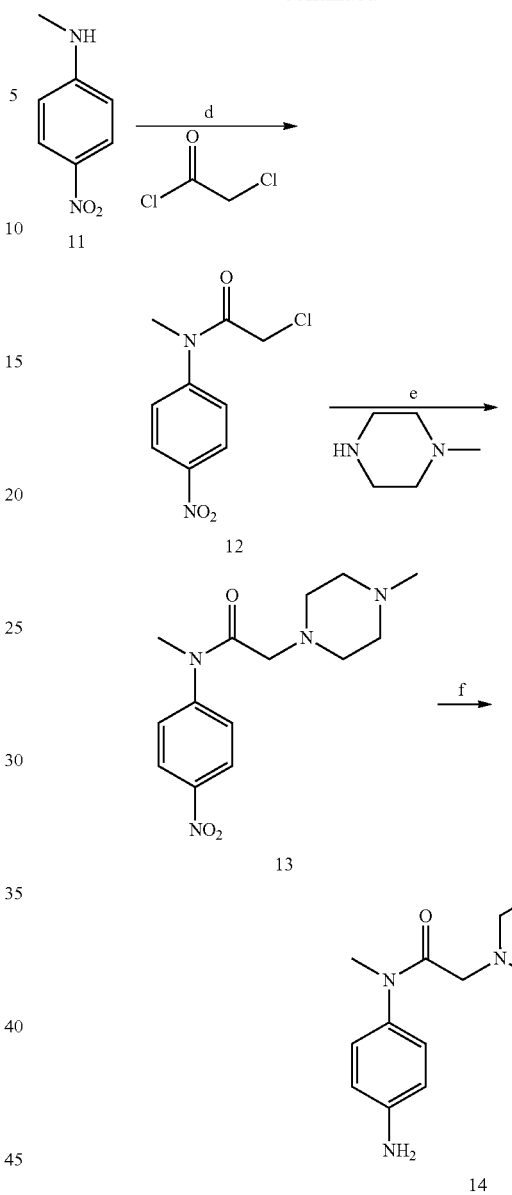

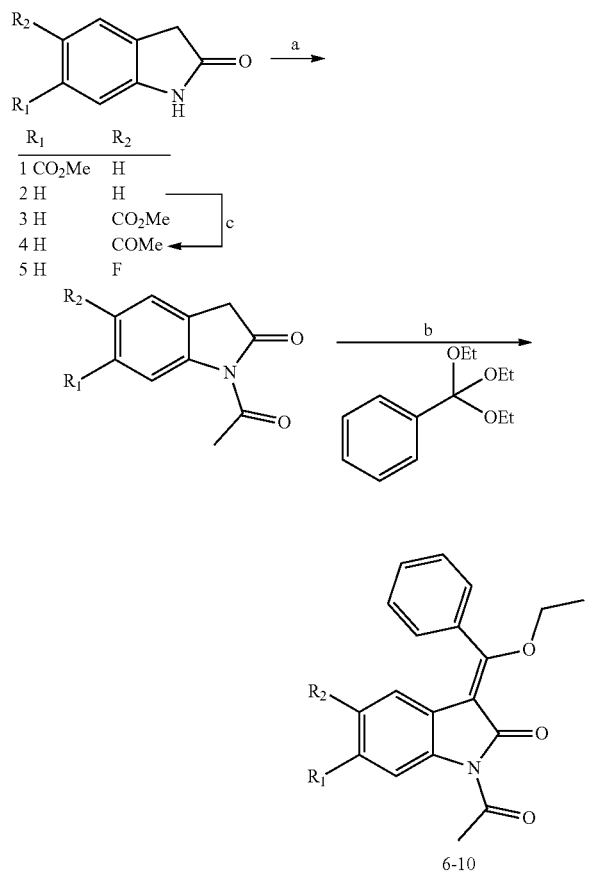

Scheme 1.

Synthesis of intermediates. Reagents and conditions: (a) Ac₂O, 130° C., 8 h; (b) PhC(OEt)₃, Ac₂O, 120° C., 6 h, 46-51% (for two steps a and b); (c) AcCl, AlCl₃, 1,2-dichloroethane, below 10° C., 1 h then RT, 12 h 72%; (d) chloroacetyl chloride, ethyl acetate, 70° C., 1 h, 90%; (e) N-methylpiperazine, toluene, 55° C., 2 h; (f) Pd/C, H₂, ⁱPr—OH, RT, 12 h, 76% (for two steps e and f).

Final indolinone analogs 15-19 were prepared by addition of 14 to substituted indolinones 6-10 and subsequent elimination of ethanol, followed by acetyl cleavage using piperidine in one pot (Scheme 2). Additional 5 or 6-substituted amide analogs 22-25 were synthesized from the corresponding 5 or 6-substituted methyl ester derivatives by hydrolysis using aqueous 1 N NaOH and subsequent standard amide coupling reactions using N-methyl amine and N,N-dimehtylamine after TBTU or HBTU activation (Scheme 2). The 5, or 6-substituted indolinone derivatives 15-25 in Table 5 were evaluated for their ability to inhibit MELK.

Scheme 2.

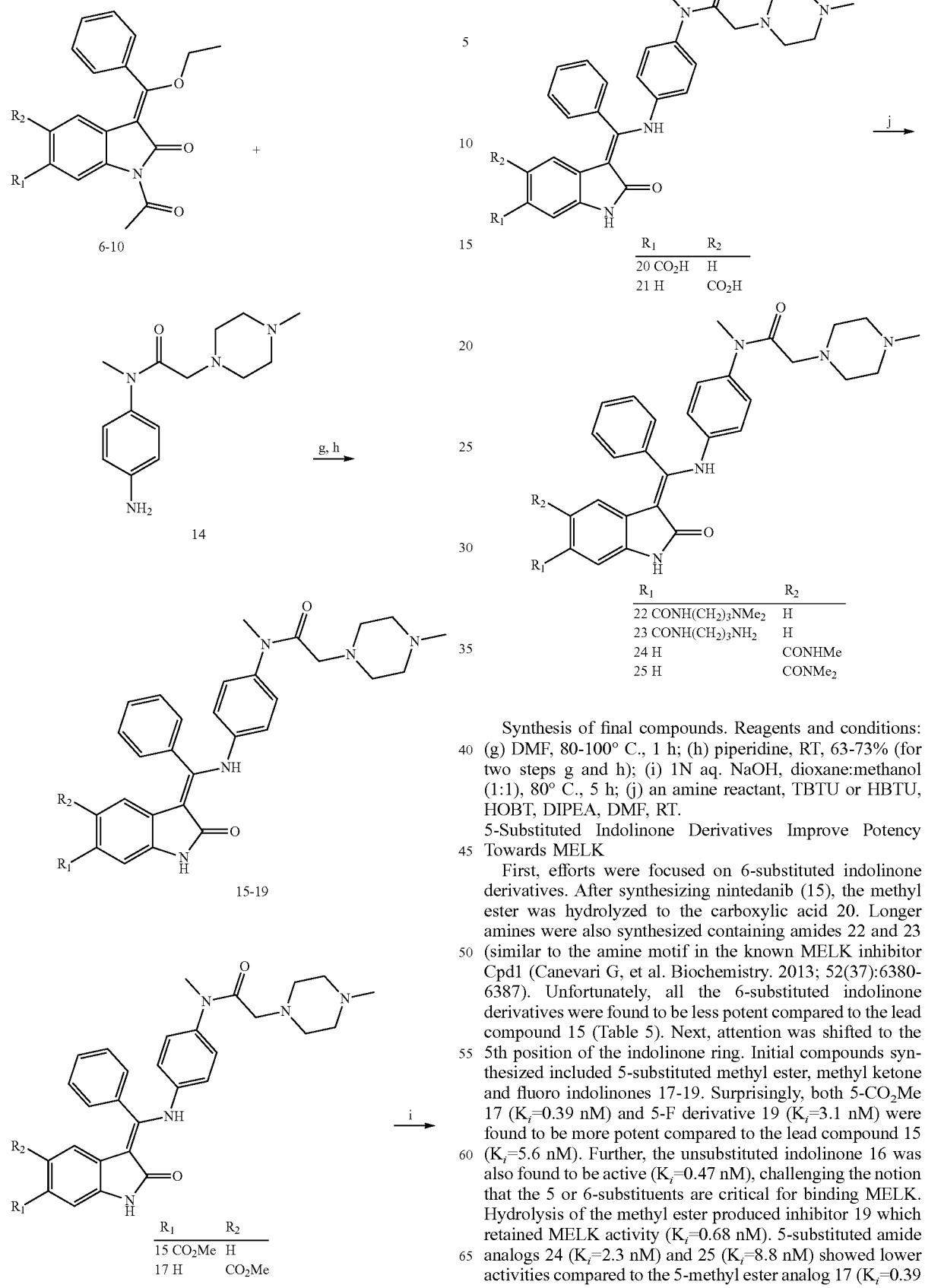

| | $R_1$ | $R_2$ |
|---|---|---|
| 20 | $CO_2H$ | H |
| 21 | H | $CO_2H$ |

| | $R_1$ | $R_2$ |
|---|---|---|
| 22 | $CONH(CH_2)_3NMe_2$ | H |
| 23 | $CONH(CH_2)_3NH_2$ | H |
| 24 | H | CONHMe |
| 25 | H | $CONMe_2$ |

| | $R_1$ | $R_2$ |
|---|---|---|
| 15 | $CO_2Me$ | H |
| 17 | H | $CO_2Me$ |

Synthesis of final compounds. Reagents and conditions: (g) DMF, 80-100° C., 1 h; (h) piperidine, RT, 63-73% (for two steps g and h); (i) 1N aq. NaOH, dioxane:methanol (1:1), 80° C., 5 h; (j) an amine reactant, TBTU or HBTU, HOBT, DIPEA, DMF, RT.

5-Substituted Indolinone Derivatives Improve Potency Towards MELK

First, efforts were focused on 6-substituted indolinone derivatives. After synthesizing nintedanib (15), the methyl ester was hydrolyzed to the carboxylic acid 20. Longer amines were also synthesized containing amides 22 and 23 (similar to the amine motif in the known MELK inhibitor Cpd1 (Canevari G, et al. Biochemistry. 2013; 52(37):6380-6387). Unfortunately, all the 6-substituted indolinone derivatives were found to be less potent compared to the lead compound 15 (Table 5). Next, attention was shifted to the 5th position of the indolinone ring. Initial compounds synthesized included 5-substituted methyl ester, methyl ketone and fluoro indolinones 17-19. Surprisingly, both 5-$CO_2Me$ 17 ($K_i$=0.39 nM) and 5-F derivative 19 ($K_i$=3.1 nM) were found to be more potent compared to the lead compound 15 ($K_i$=5.6 nM). Further, the unsubstituted indolinone 16 was also found to be active ($K_i$=0.47 nM), challenging the notion that the 5 or 6-substituents are critical for binding MELK. Hydrolysis of the methyl ester produced inhibitor 19 which retained MELK activity ($K_i$=0.68 nM). 5-substituted amide analogs 24 ($K_i$=2.3 nM) and 25 ($K_i$=8.8 nM) showed lower activities compared to the 5-methyl ester analog 17 ($K_i$=0.39 nM). Also, complete loss of MELK activity ($K_i$>5000 nM)

was observed when the key intermediates 6, 8 and 14 were tested. This suggests the importance of the two key fragments in combination.

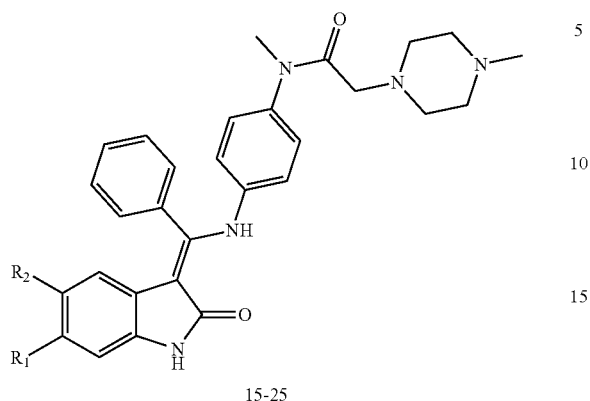

15-25

TABLE 5

Characterization of indolinone derivatives.

| Compound | $R_1$ | $R_2$ | $IC_{50}$ (nM) | $K_i{}^a$ ± SE (nM) |
|---|---|---|---|---|
| 15 | $CO_2Me$ | H | 43 ± 3.4 | 5.6 ± 0.4 |
| 16 | H | H | 3.6 ± 0.4 | 0.47 ± 0.06 |
| 17 | H | $CO_2Me$ | 3 ± 0.8 | 0.39 ± 0.09 |
| 18 | H | COMe | 354 ± 35 | 46 ± 4.6 |
| 19 | H | F | 24 ± 4.7 | 3.1 ± 0.6 |
| 20 | $CO_2H$ | H | 1145 ± 168 | 149 ± 22 |
| 21 | H | $CO_2H$ | 5.2 ± 0.5 | 0.68 ± 0.07 |
| 22 | $CONH(CH_2)_3NMe_2$ | H | 2700 ± 540 | 358 ± 71 |
| 23 | $CONH(CH_2)_3NH_2$ | H | >5000 | >650 |
| 24 | H | CONHMe | 18 ± 3.8 | 2.3 ± 0.5 |
| 25 | H | $CONMe_2$ | 67 ± 11 | 8.8 ± 1.4 |

$^a K_i$ calculated using Equation 4, where [ATP] = 40 μM, $K_M{}^{app}$ (ATP) = 6 μM

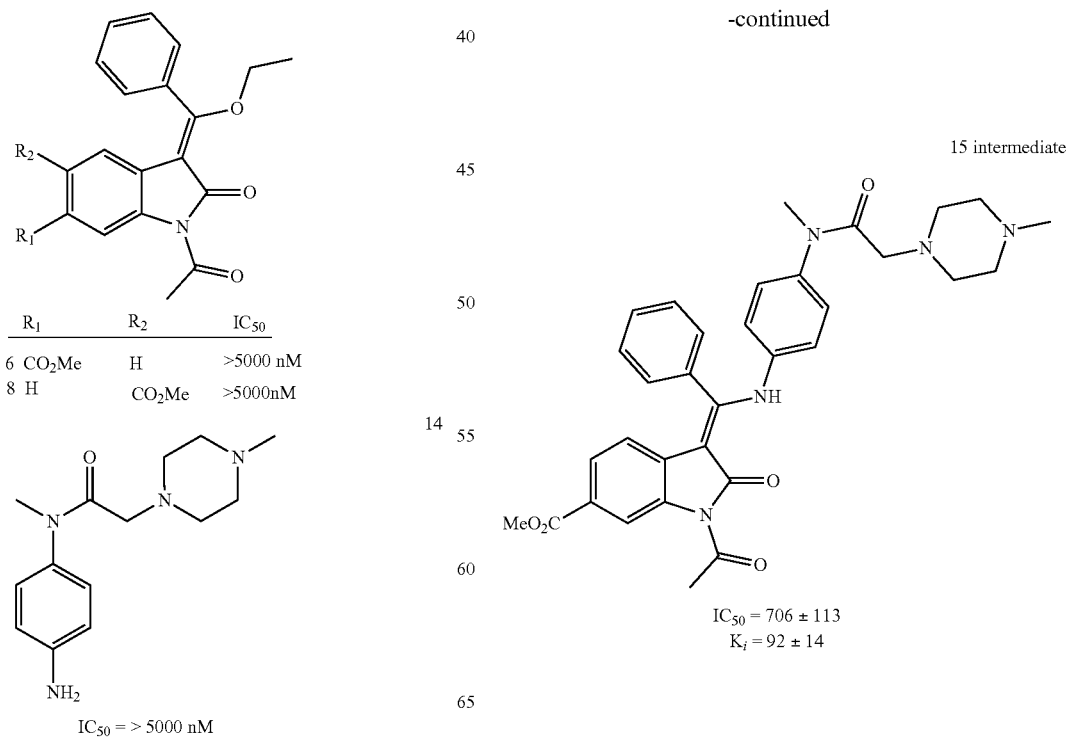

TABLE 6

Fragment and intermediate potency ($K_i$'s of synthetic intermediates)

| Compound | $K_i$ ± SD (nM) |
|---|---|
| 6 | >650 |
| 8 | >650 |
| 14 | >650 |
| 15 | 84 ± 13 |

Figure 3:
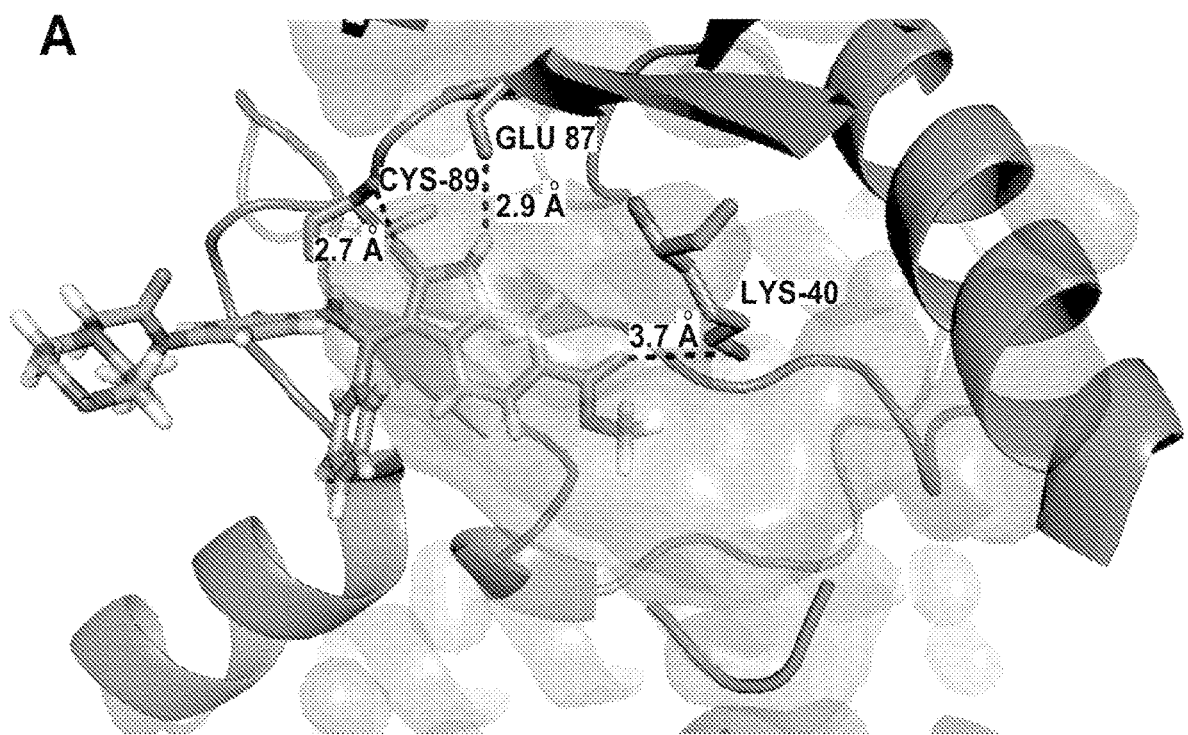
FIG. 3 shows the top-down view of the ATP binding pocket of MELK (PDB: 4BKY) and predicted binding poses of compounds 15 (6-$CO_2$Me, A) and 17 (5-$CO_2$Me, B). A) Compound 15 forms hydrogen bonds with C89, E87, and K40 of the ATP binding pocket. 6th position substitution sterically prevents 15 from achieving optimal complementarity with the curvature of the binding site. B) 5th position methyl ester substitution in 17 forms the same hydrogen bonds, but allows deeper penetration of the compound into the binding site, shortening hydrogen bond lengths between MELK and the compound by up to an angstrom in some cases. Measurements were generated using Pymol software. H-bonds are shown as dashed black lines. ATP binding pocket is shaded in light purple. Ribbon backbones of residues 13-19 and 23-27 are excluded for clarity.
Figure 3:
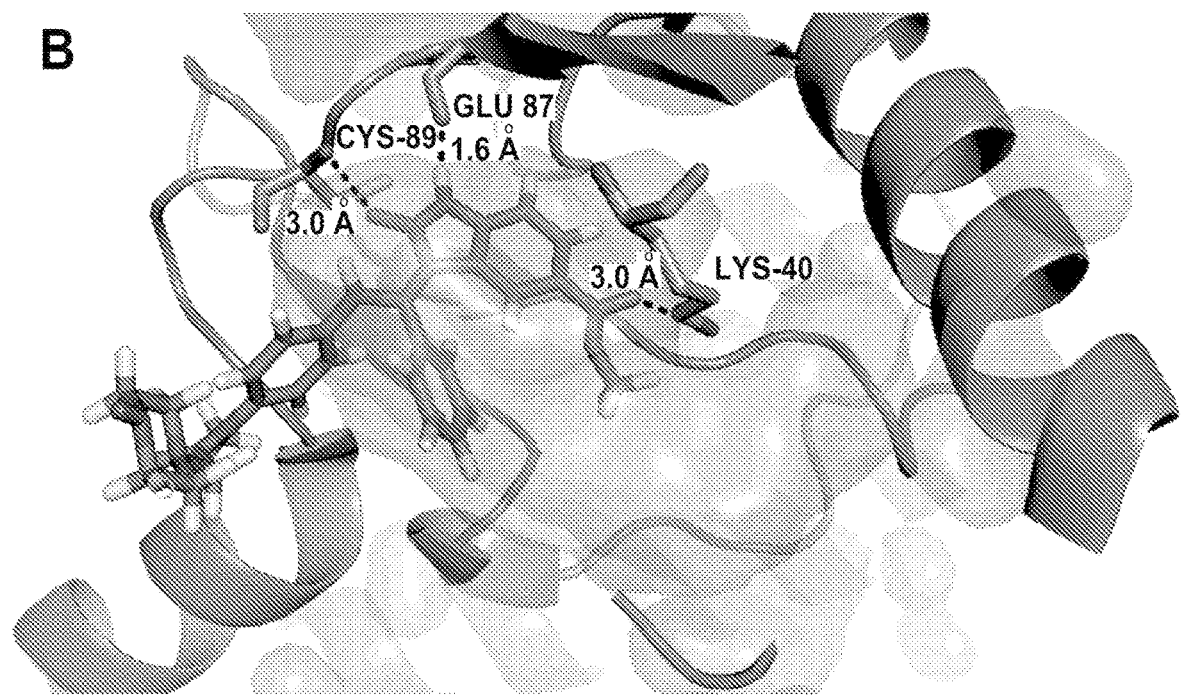

To further understand the substantial increase in potency by shifting the methyl ester from the 6 to the 5 position, both compound 15 (6-$CO_2$Me) and compound 17 (5-$CO_2$Me) were docked with MELK (PDB: 4BKY) and analyzed using Gold5.2 with the ChemPLP scoring function. The methyl ester substituents of both compounds are within direct or water-bridged hydrogen bonding distance of K40 (FIG. 3). A methyl ester in the 5th position, however is predicted to force 17 deeper into the narrow groove leading to K40. This would likely shorten the H-bond distance, and strengthen the interaction. Moreover, this modification enables 17 to adopt a conformation more complementary to the shape of the binding pocket, facilitating the interaction of the indolinone core with E87 through an additional hydrogen bond. Concordantly, retained potency of 16 (unsubstituted indolinone) suggests that suboptimal substituent position significantly affects inhibitor binding. Alternatively, the potency of 16 may also be explained by the ability of an unsubstituted indolinone to adopt a greater number of binding modes.

MELK Derivatives Show Differential Selectivity Towards Functionally Related Kinases In light of the same chemical reaction they all perform, kinases by definition have a characteristic binding site for ATP. While critical residues must be present for the phosphoryl transfer reaction (e.g., those to coordinate magnesium ions and the phosphoester chain), there is considerable diversity in residues that additionally influence the volume and shape of the ATP binding pocket, giving rise to the possibility of kinase inhibitor selectivity. Such parameters not only determine how tightly an enzyme can bind ATP, but also dictate what small molecules will effectively compete with ATP and take advantage of unique surface complementarities. Therefore, these new inhibitors were investigated in the context of inhibiting MELK's most closely related family members AMPK and NUAK1. It was also determined whether the most potent MELK inhibitor derivatives affected other kinases involved in putative MELK-related pathways (the cell cycle and CHK1), or those driving certain AMPK-RK signaling pathways (CAMKKII). In contrast, ERK2 served as an unrelated control.

The top three most potent MELK inhibitor derivatives, compounds 16, 17, and 21, were analyzed in dose-response inhibition assays and used apparent $K_M^{ATP}$ values determined under our experimental conditions to calculate $K_i$ (Table 8). Compound 16, which contains no substituent at either the 5- or 6-position of the indolinone, was the least selective inhibitor of the three (Table 7). Compound 16 inhibited both AMPK and NUAK1 quite well, resulting in only a 5-10 fold difference in $K_i$ compared to MELK. Addition of a methyl ester at the 5-position (compound 17) resulted in comparable potency towards MELK, but increased selectivity towards other kinases. Hydrolysis of the methyl ester to the carboxylate (compound 21) yielded the best selectivity profile of the three inhibitors tested, displaying >100-fold difference in relative $K_i$ compared to MELK for CHK1, CAMKK2, and ERK2. All three compounds remained fairly tight binding inhibitors of closely related kinases AMPK and NUAK1.

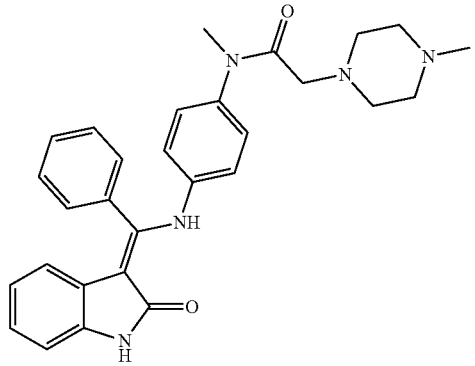

Compound 16

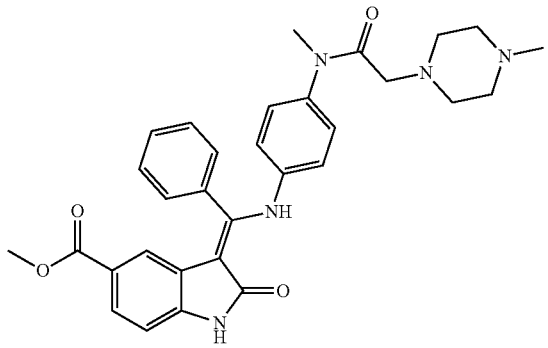

Compound 17

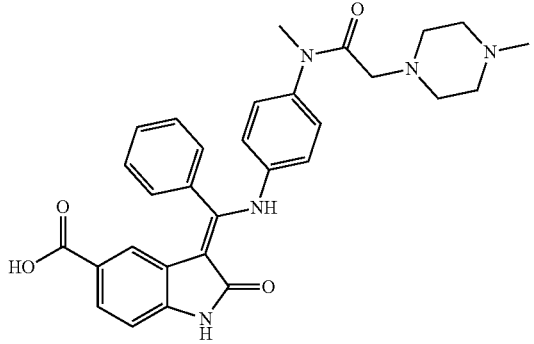

Compound 21

TABLE 7

Selectivity of MELK inhibitor derivatives against selected kinases.

| Kinase | Compound 16 | | Compound 17 | | Compound 21 | |
|---|---|---|---|---|---|---|
| | $K_i$ | $\varphi^a$ | $K_i$ | $\varphi^a$ | $K_i$ | $\varphi^a$ |
| MELK | 0.47 ± 0.06 | 1.00 | 0.39 ± 0.09 | 1.00 | 0.68 ± 0.07 | 1.00 |
| AMPK | 4.2 ± 0.3 | 8.9 ± 0.2 | 9.2 ± 1.7 | 24 ± 0.3 | 4.9 ± 0.6 | 7.2 ± 0.2 |
| NUAK1 | 1.7 ± 0.17 | 3.6 ± 0.2 | 11 ± 0.86 | 28 ± 0.2 | 8.6 ± 1.6 | 13 ± 0.2 |
| CHK1 | 10 ± 0.5 | 18 ± 0.2 | 7 ± 0.17 | 18 ± 0.2 | 81 ± 5.6 | 120 ± 0.1 |
| CAMKK2 | 15 ± 1.8 | 32 ± 0.2 | 31 ± 11 | 80 ± 0.4 | 85 ± 9.2 | 125 ± 0.2 |
| ERK2 | 1160 ± 320 | 2500 ± 0.3 | 3000 ± 1300 | 7700 ± 0.5 | 19000 ± 3800 | 28000 ± 0.2 |

$^a \varphi = K_i^{Enzyme}/K_i^{MELK}$

While not appreciably affecting potency towards MELK, additional negative charge at the 5-position enhances compound selectivity. Such a trend is particularly apparent in the case of CHK1. MELK has been implicated in regulation of the cell cycle though inhibitory phosphorylation of the phosphatase CDC25B, whose main function is to promote mitotic entry through dephosphorylation and activation of CDK1/cyclin B (Davezac N, et al. Oncogene. 2002; 21(50): 7630-7641). It has additionally been reported that MELK overexpression may increase DNA damage and replication stress tolerance in cancer cells, as MELK inhibition resulted in a prolonged ATM-CHK2 response (Beke L, et al. Biosci Rep. 2015). The reported roles of MELK in cancer cells therefore suggest potential intimate relation with those functions of CHK1. Thus, a MELK inhibitor that affords additional selectivity against CHK1, like compound 21, is a valuable tool for further delineation of MELK's role in the context of cell division and DNA damage and repair. Finally, it should be noted that while Compound 17 is the most potent in vitro, it is possible that its methyl ester is hydrolyzed in vivo due to the prevalence of esterases at the cellular and whole organism level. Thus, not only is compound 21 the most selective of the three, it is also a likely potent species present to inhibit MELK in a living system.

Inhibitor 17 Decreases Cell Proliferation of TNBC Cells

Figure 4:
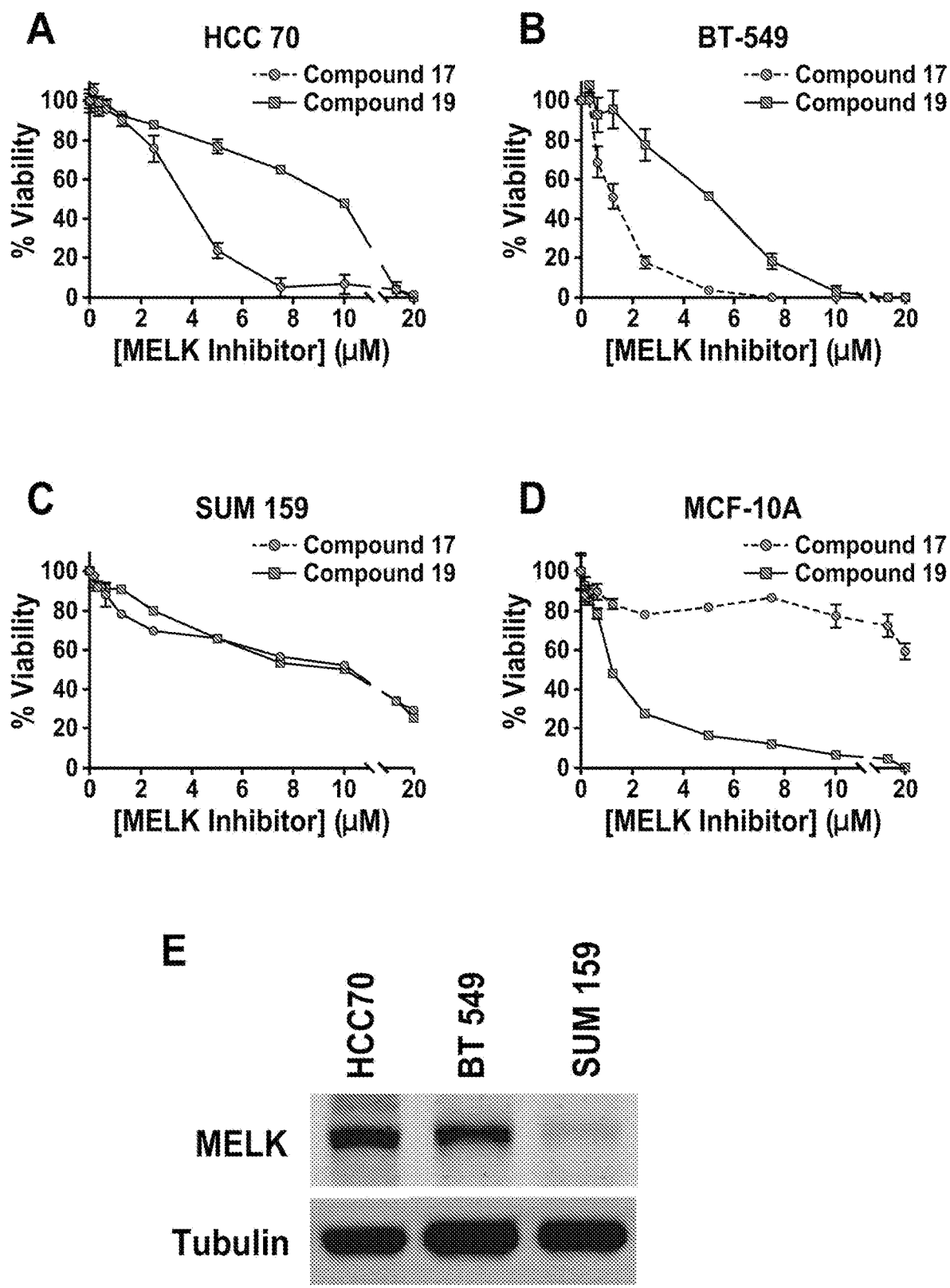
FIG. 4 shows inhibitor 17 suppresses cell proliferation of triple negative breast cancer (TNBC) cells in vitro. Inhibitor 17 was more effective than inhibitor 19 at suppressing cell proliferation, and cells expressing high levels of MELK were more sensitive to inhibitor 17 than cells expressing low levels of MELK. Cells were seeded in 96-well plates and the next day treated with inhibitors at the indicated concentrations. Seventy-two hours later, cell viability was determined using the CellTiter-Blue Cell Viability Assay for the following cell lines: A) HCC70; B) BT549; C) SUM159; and D) MCF-10A cell lines. E) MELK expression levels are shown for HCC70, BT549, and SUM159 cell lines. Tubulin is shown as the loading control.
Figure 5:
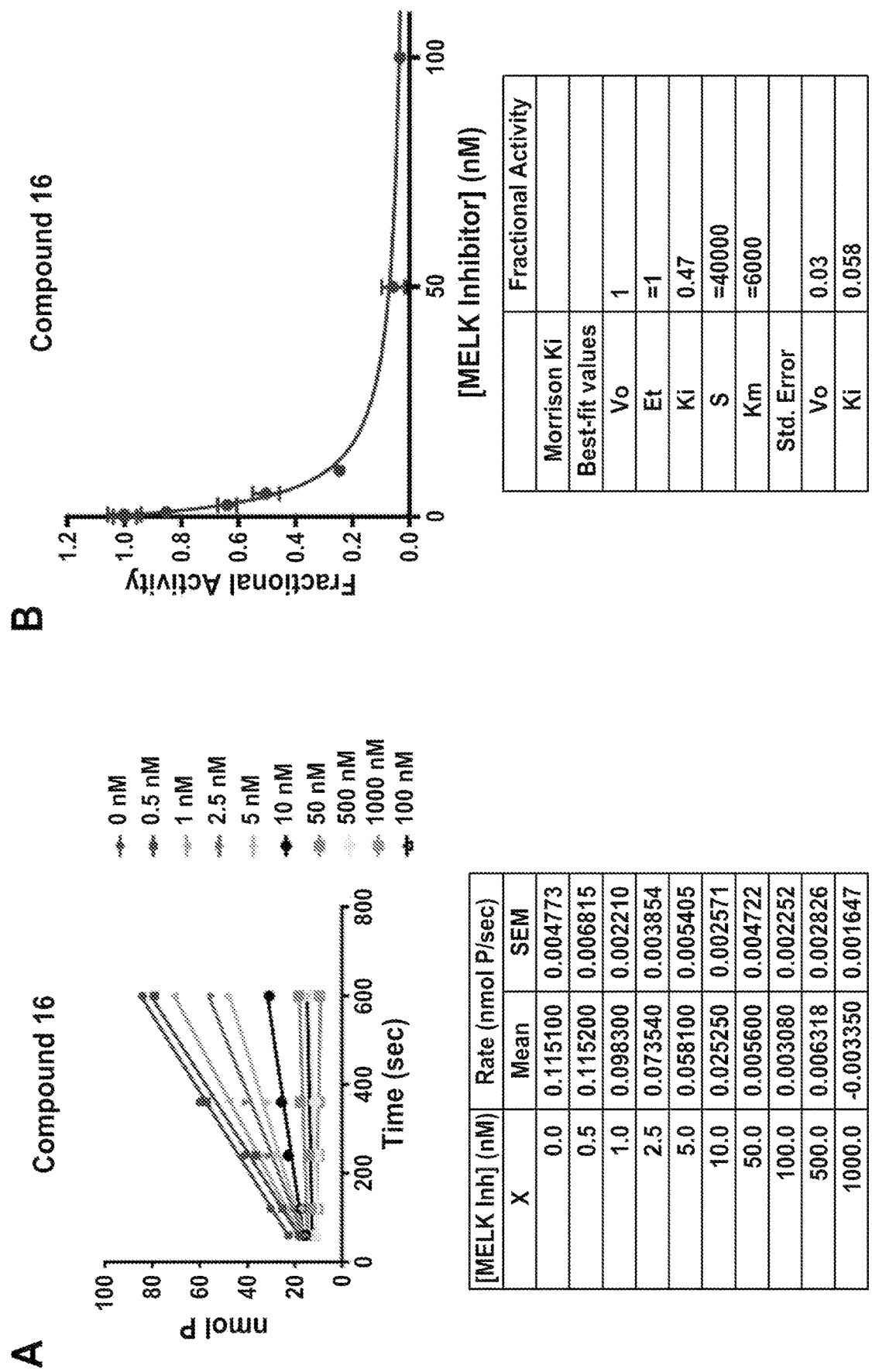
FIG. 5 shows time course and $IC_{50}$ plots for the three most potent inhibitors, compounds 16, 17, and 21. (a) Time course for inhibition at different concentrations for compound 16. (b) $IC_{50}$ plot showing fractional activity vs. inhibitor concentration for compound 16. (c) Time course for inhibition at different concentrations for compound 17. (d) $IC_{50}$ plot showing fractional activity vs. inhibitor concentration for compound 17. (e) Time course for inhibition at different concentrations for compound 21. (f) $IC_{50}$ plot showing fractional activity vs. inhibitor concentration for compound 21. Rates derived for compounds 16 and 21 represent the average for three independent experiments, whereas those for compound 17 are the average for 4 separate experiments. $K_i$ values were fit directly in Prism® using experimentally determined $K_M^{ATP}$ of 6±1.5 µM (two independent replicates) and an ATP concentration of 40 µM.
Figure 5:
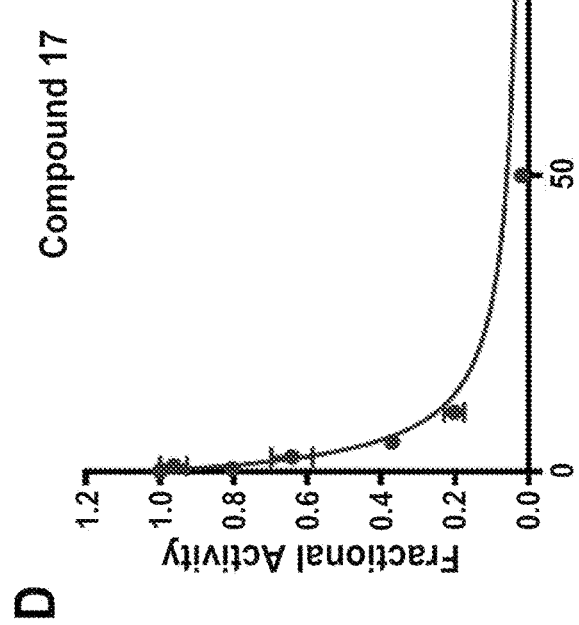
Figure 5:
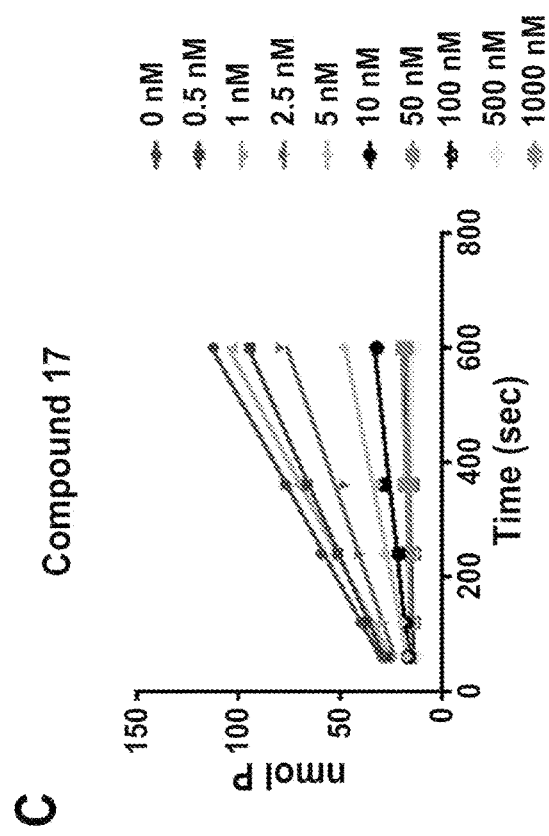
Figure 5:
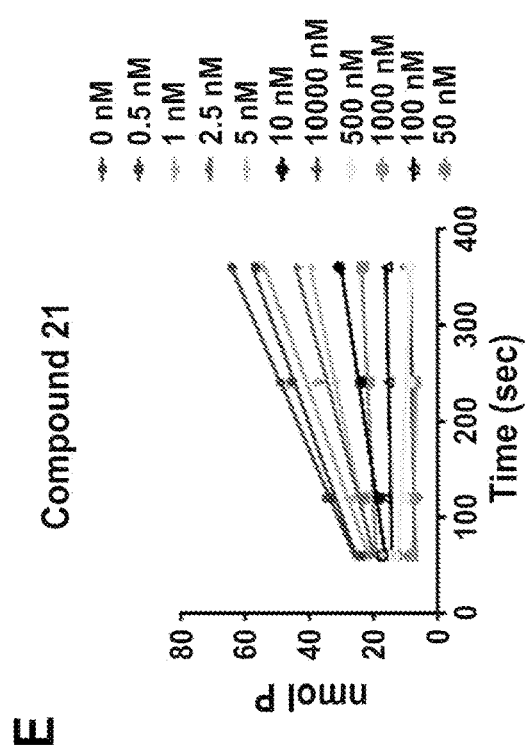
Figure 5:
Figure 6:
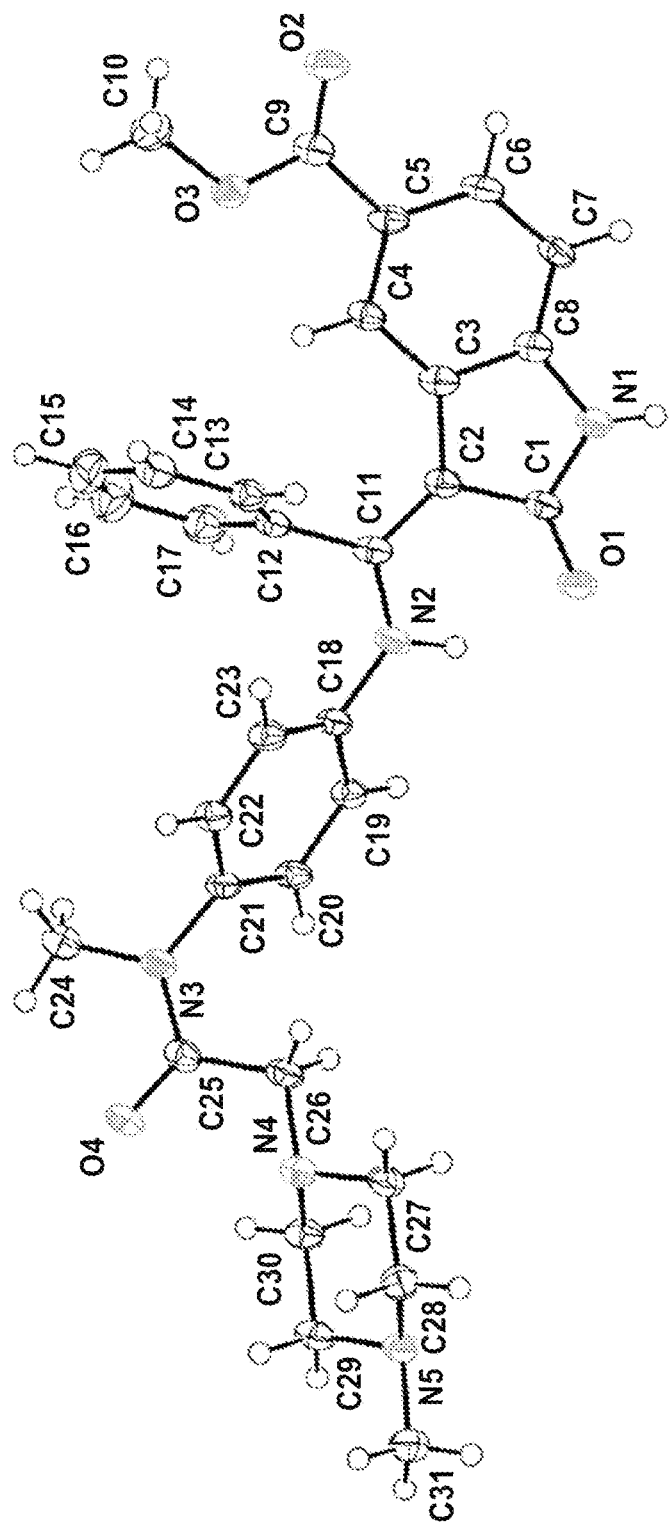
FIG. 6 shows the X-ray structure for the 5-CO2Me analog (compound 17).

As MELK was found to be essential in basal-like breast cancer cells (Wang Y, et al. eLife. 2014: e01763), the CellTiter-Blue assay was used to test the ability of two compounds (17 and 19, FIG. 4A) to inhibit the proliferation of various TNBC subtypes (Lehmann B D, et al. The Journal of clinical investigation. 2011; 121(7):2750-2767), HCC70 (BL2 subtype), BT-549 (mesenchymal) and SUM-159 (mesenchymal stem-like), as well as the immortalized mammary epithelial cell line MCF10A (classified as Basal B by molecular profiling) (Kao J, et al. PloS one. 2009; 4(7): e6146). Proliferation of the HCC70, BT-549, and SUM-159 cells were clearly impacted by treatment with 17, whereas the MCF10A cells remained largely unaffected at 10 µM. In contrast, 19, inhibited all cell lines. Such data is congruent with our previous results (Table 5), as 17 is around 10 fold more potent than the 5-fluoro derivative 19 in vitro, and 17 is a more effective inhibitor of proliferation in cells. The ability of 19 to inhibit proliferation in MCF10A cells may be explained by the fact that 5-fluoro derivative may be less selective, much like the unsubstituted indolinone 16. Furthermore, cell lines expressing high levels of MELK protein (HCC70 and BT549) were more sensitive to 17 than those cells with low levels of MELK expression (SUM159). Collectively, these data show that 17 selectively inhibits proliferation of TNBC cells expressing high levels of MELK.

Summary

In conclusion, 5-substituted indolinones were identified as a novel MELK inhibitor scaffold though targeted kinase library inhibitor screening. Derivatization of the most potent MELK inhibitor identified in the initial screen (nintedanib) led to three tightly binding MELK inhibitors with subnanomolar inhibition constants (compounds 16,17, and 21). The unsubstituted indolinone was the least selective against a small subset of evolutionarily and functionally related kinases. However, compound 21 afforded selectivity against 3 out of 5 kinases tested, particularly against the mitotic kinase CHK1. The most potent MELK inhibitor, compound 17, decreases viability and proliferation of multiple TNBC cell lines with high MELK expression. Conversely, compound 17 shows little effect on low MELK-expressing MCF-10A cells, an immortalized breast epithelial cell line.

Methods

Chemistry

General Information. Reagents and starting materials including indolinones 1-3, and 5, and N-Methyl-4-nitroaniline 11 were purchased from various commercial sources including Sigma-Aldrich or Matrix Scientific and used without further purification unless otherwise stated. 5-Acetylindolinone 4 and aromatic amine intermediate 14 were prepared by literature procedures (Roth G J, et al. J Med Chem. 2009; 52(14):4466-4480; Heckel A B, et al. Inventor; Boehringer Ingelheim International GmbH (Ingelheim, DE), assignee. Cycloalkyl-containing 5-acylindolinones, the preparation thereof and their use as medicaments. 2007). All reactions were carried out in oven- or flame-dried glassware under argon. Thin-layer chromatography (TLC) was performed using pre-coated TLC plates with silica gel 60 $F_{254}$ (EMD) or with aluminum oxide 60 $F_{254}$ neutral. Flash column chromatography was performed using 40-63 µm (230-400 mesh ASTM) silica gel (EMD). Melting points were recorded on a Thomas Hoover capillary melting point apparatus. NMR spectra were recorded on a Varian MR spectrometer. High-resolution mass and liquid chromatography mass spectral data were obtained at the University of Texas at Austin. Compounds were characterized by NMR and HRMS or LCMS.

5-Acetylindolin-2-one (4). By following acylation procedure reported in a patent (Heckel A B, et al. Inventor; Boehringer Ingelheim International GmbH (Ingelheim, DE), assignee. Cycloalkyl-containing 5-acylindolinones, the preparation thereof and their use as medicaments. 2007). 5-acetylindolin-2-one was prepared from indolin-2-one and $AlCl_3$. The crude was recrystalized from ethyl acetate to obtain 72% of the title compound. $^1$H NMR (400 MHz, DMSO-$d_6$): δ 10.76 (br s, 1H, NH), 7.85 (m, 1H, Ar—H), 7.80 (m, 1H, Ar—H), 6.90 (d, J=8.0 Hz, 1H, Ar—H), 3.55 (s, 2H), 2.50 (s, 3H, Ac).

General procedure for the synthesis of N-acetyl-3-(ethoxy (phenyl)methylene)-2-oxoindolines (Compounds 6-10). Methyl (Z)-1-acetyl-3-(ethoxy(phenyl)methylene)-2-oxoindoline-6-carboxylate (6) (Roth G J, et al. J Med Chem. 2009; 52(14):4466-4480). Indolinone 1 (1000 mg, 52.3 mmol) was suspended in acetic anhydride (10 mL) and refluxed at 130° C. for 8 h. The reaction mixture was allowed to cool to 50° C. and (triethoxymethyl)benzene (2930 mg, 131 mmol) was added. The resulting reaction mixture was stirred at 120° C. for 6 h. Then, volatiles were removed in vacuo and petroleum ether was added to the obtained residue. After triturating for 15 minutes, the separated solids were filtered and washed with petroleum ether and then dried under vacuum to afford 974 mg (51%) of title compound. $^1$H NMR (400 MHz, DMSO-$d_6$): δ 8.75 (s, 1H), 8.10 (d, J=8.0 Hz, 1H), 7.89 (d, J=8.0 Hz, 1H), 7.49-7.58 (m, 5H), 4.01 (q, J=7.2 Hz, 2H), 3.87 (s, 3H), 2.44 (s, 3H), 1.35 (t, J=8.0 Hz, 3H). HRMS m/z found 365.1260, calcd for $C_{21}H_{19}NO_5$ [M]$^+$ 365.1263.

(Z)-1-acetyl-3-(ethoxy(phenyl)methylene)indolin-2-one (7). The title compound was synthesized in 46% yield using similar procedure as described for the synthesis of compound 6 by swapping indolinone 2 for inodolinone 1. Major conformer $^1$H NMR (400 MHz, DMSO-$d_6$): δ 8.17-8.13 (m, 1H), 8.02-7.99 (m, 1H), 7.56-7.46 (m, 5H), 7.30-7.22 (m, 2H), 3.94 (q, J=7.2 Hz, 2H), 2.43 (s, 3H), 1.33 (t, J=7.4 Hz, 3H). LCMS m/z found 308.1, calcd for $C_{19}H_{18}NO_3$ [M+H]$^+$ 308.1.

Methyl (Z)-1-acetyl-3-(ethoxy(phenyl)methylene)-2-oxoindoline-5-carboxylate (8). The title compound was synthesized in 48% yield using similar procedure as described for the synthesis of compound 6 by swapping indolinone 3 for inodolinone 1. $^1$H NMR (400 MHz, DMSO-$d_6$): δ 8.61 (d, J=1.6 Hz, 1H), 8.23 (d, J=8.4 Hz, 1H), 7.92 (dd, J=8.4 Hz, J=1.6 Hz, 1H), 7.58-7.49 (m, 5H), 3.99 (q, J=7.0 Hz, 2H), 3.87 (s, 3H), 2.45 (s, 3H), 1.37 (t, J=7.0 Hz, 3H). HRMS m/z found 346.1058, calcd for $C_{19}H_{17}NNaO_4$ [M-Ac+Na]$^+$ 346.1055.

(Z)-1,1'-(3-(Ethoxy(phenyOmethylene)-2-oxoindoline-1,5-diyObis(ethan-1-one) (9). The title compound was synthesized in 47% yield using similar procedure as described for the synthesis of compound 6 by swapping indolinone 4 for inodolinone 1. $^1$H NMR (400 MHz, DMSO-$d_6$): δ 8.58 (d, J=2.0 Hz, 1H), 8.23 (d, J=8.4 Hz, 1H), 7.94 (dd, J=8.4 Hz, J=2.0 Hz, 1H), 7.58-7.49 (m, 5H), 3.99 (q, J=7.0 Hz, 2H), 2.61 (s, 3H), 2.45 (s, 3H), 1.39 (t, J=8.0 Hz, 3H). LCMS m/z found 350.1, calcd for $C_{21}H_{20}NO_4$ [M+H]$^+$ 350.1.

(Z)-1-acetyl-3-(Ethoxy(phenyl)methylene)-5-fluoroindolin-2-one (10). The title compound was synthesized in 48% yield using similar procedure as described for the synthesis of compound 6 by swapping indolinone 5 for inodolinone 1. Major conformer $^1$H NMR (400 MHz, DMSO-$d_6$): δ 8.16 (m, 1H), 7.71 (m, 1H), 7.57-7.47 (m, 5H), 7.12 (m, 1H), 3.98 (q, J=7.0 Hz, 2H), 2.41 (s, 3H), 1.33 (t, J=8.0 Hz, 3H). $^{19}$F NMR (376 MHz, DMSO-$d_6$): δ−117.6 (m). LCMS m/z found 326.1, calcd for $C_{19}H_{17}FNO_3$ [M+H]$^+$ 326.1.

N-(4-Aminophenyl)-N-methyl-2-(4-methylpiperazin-1-yl)acetamide (14) The title acetamide compound was prepared from N-methyl-4-nitroaniline 11 using similar procedure as described in literature (Roth G J, et al. J Med Chem. 2009; 52(14):4466-4480). $^1$H NMR (400 MHz, DMSO-$d_6$): δ 2.10 (s, 3H), 2.14-2.43 (m, 8H), 2.79 (s, 2H), 3.03 (s, 3H), 5.23 (s, 2H), 6.52-6.57 (m, 2H), 6.88-6.92 (m, 2H). HRMS m/z found 263.1866, calcd for $C_{14}H_{23}N_4O$ [M+H]$^+$ 263.1872.

General procedure for the synthesis of final compounds 15-19. Methyl (Z)-3-(((4-(N-methyl-2-(4-methylpiperazin-1-yl)acetamido)phenyl)amino)(phenyl)methylene)-2-oxoindoline-6-carboxylate (15). To a suspension of methyl (Z)-1-acetyl-3-(ethoxy(phenyl)methylene)-2-oxoindoline-6-carboxylate (6) (500 mg, 1.368 mmol) in DMF (3.5 mL) was added N-(4-aminophenyl)-N-methyl-2-(4-methylpiperazin-1-yl)acetamide (14) (395 mg, 1.505 mmol, 1.1 equiv.) at room temperature. After heating the reaction mixture at 80° C. for 1 h, it was allowed to cool to RT. Piperidine (297 μL, 3.010 mmol, 2.2 equiv.) was then added and stirred for 2 h. Volatiles were removed in vacuo and water was added to the obtained residue and stirred for 15 min. Precipitate was then filtered under suction and cake was washed with water, then with minimum amount of cold methanol, and then ether. The obtained product was purified by column chromatography (neutral $Al_2O_3$, 0-10% methanol in $CH_2Cl_2$) to afford 532 mg (72%) of target molecule 15. Major conformer $^1$H NMR (400 MHz, DMSO-$d_6$): δ 12.22 (s, 1H), 10.98 (s, 1H), 7.66-7.47 (m, 5H), 7.42 (s, 1H), 7.24-7.09 (m, 3H), 6.89 (d, J=8.0 Hz, 2H), 5.83 (d, J=8.0 Hz, 1H), 3.77 (s, 3H), 3.06 (s, 3H), 2.69 (s, 2H), 2.34-2.06 (brs, 8H), 2.10 (s, 3H). HRMS found 540.2606, calcd for $C_{31}H_{34}N_5O_4$ [M+H]$^+$ 540.2605.

(Z)—N-Methyl-2-(4-methylpiperazin-1-yl)-N-(4-(((2-oxoindolin-3-ylidene)(phenyl)methyl)amino)phenyl)acetamide (16) The title compound was synthesized in 64% yield using similar procedure as described for the synthesis of compound 15 by swapping (Z)-1-acetyl-3-(ethoxy(phenyl)methylene)indolin-2-one (7) for inodolinone derivative 6. A 58:42 mixture of conformers $^1$H NMR (400 MHz, DMSO-$d_6$): δ 12.19 and 12.02 (s, 1H), 10.74 and 10.59 (s, 1H), 7.61-5.75 (m, 13H), 3.17-2.64 (m, 5H), 2.36-2.07 (m, 11H). HRMS m/z found 482.2408, calcd for $C_{29}H_{32}N_5O_2$ [M+H]$^+$ 482.2400.

Methyl(Z)-3-(((4-(N-methyl-2-(4-methylpiperazin-1-yl)acetamido)phenyl)amino)(phenyl)methylene)-2-oxoindoline-5-carboxylate (17). The title compound was synthesized in 73% yield using similar procedure as described for the synthesis of compound 15 by swapping Methyl (Z)-1-acetyl-3-(ethoxy(phenyl)methylene)-2-oxoindoline-5-carboxylate (8) for inodolinone derivative 6. Major conformer $^1$H NMR (400 MHz, DMSO-$d_6$): δ 11.97 (s, 1H), 11.13 (s, 1H), 7.63-7.47 (m, 6H), 7.13 (d, J=8.4 Hz, 2H), 6.94 (d, J=8.4 Hz, 1H), 6.88 (d, J=8.4 Hz, 2H), 6.51 (s, 1H), 3.63 (s, 3H), 3.06 (s, 3H), 2.69 (s, 2H), 2.19 (brs, 8H), 2.10 (s, 3H). HRMS m/z found 540.2613, calcd for $C_{31}H_{34}N_5O_4$ [M+H]$^+$ 540.2605.

(Z)—N-(4-(((5-Acetyl-2-oxoindolin-3-ylidene)(phenyl) methyl)amino)phenyl)-N-methyl-2-(4-methylpiperazin-1-yl)acetamide (18). The title compound was synthesized in 63% yield using similar procedure as described for the synthesis of compound 15 by swapping (Z)-1,1'-(3-(Ethoxy (phenyl)methylene)-2-oxoindoline-1,5-diyl)bis(ethan-1-one) (9) for inodolinone derivative 6. Major conformer $^1$H NMR (400 MHz, DMSO-$d_6$): δ 11.94 (s, 1H), 11.14 (s, 1H), 7.63-7.50 (m, 6H), 7.13 (d, J=8.4 Hz, 2H), 6.94 (d, J=8.4 Hz, 1H), 6.90 (d, J=8.4 Hz, 2H), 6.39 (s, 1H), 3.06 (s, 3H), 2.71 (s, 2H), 2.32-2.16 (brs, 8H), 2.14 (s, 6H). HRMS found 523.2585, calcd for $C_{31}H_{33}N_5O_3$ [M]$^+$ 523.2583.

(Z)—N-(4-(((5-Fluoro-2-oxoindolin-3-ylidene)(phenyl) methyl)amino)phenyl)-N-methyl-2-(4-methylpiperazin-1-yl)acetamide (19). The title compound was synthesized in 69% yield using similar procedure as described for the synthesis of compound 15 by swapping (Z)-1-acetyl-3-(Ethoxy(phenyl)methylene)-5-fluoroindolin-2-one (10) for inodolinone derivative 6. $^1$H NMR (400 MHz, DMSO-$d_6$): δ 12.09 (s, 1H), 10.76 (s, 1H), 7.63-7.48 (m, 5H), 7.12 (d, J=8.4 Hz, 2H), 6.90-6.79 (m, 3H), 6.72 (m, 1H), 5.37 (dd, J=10.4 Hz, 2.4 Hz, 1H), 3.05 (s, 3H), 2.67 (s, 2H), 2.18 (brs, 8H), 2.10 (s, 3H). $^{19}$F NMR (376 MHz, DMSO-d$_6$): δ−123.3 (m). HRMS m/z found 500.2455, calcd for $C_{29}H_{31}FN_5O_2$ [M+H]$^+$ 500.2456.

General procedure for the synthesis of final compounds 22-25. (Z)—N-(3-(Dimethylamino)propyl)-3-(((4-(N-methyl-2-(4-methylpiperazin-1-yl)acetamido)phenyl)amino)(phenyl)methylene)-2-oxoindoline-6-carboxamide (22). 6-carboxylic acid methyl ester 15 (250 mg, 0.46 mmol) was added to 1:1 mixture of methanol and dioxane (8 mL). The resulting suspension was heated to 50° C. and then 1N aqueous NaOH solution (2.5 mL) was added. The solution was stirred for 5 h at 80° C. and then allowed to cool to room temperature. Volatiles were removed in vacuo and water was added to the obtained residue. After stirred for 10 minutes, the separated solids were filtered and washed with water and diethyl ether, and then dried under vacuum to afford crude (Z)-3-(((4-(N-Methyl-2-(4-methylpiperazin-1-yl)acetamido)phenyl)amino)(phenyl)methylene)-2-oxoindoline-6-carboxylic acid (20). Major conformer $^1$H NMR (400 MHz, DMSO-d$_6$): δ 12.20 (s, 1H), 10.96 (s, 1H), 7.63-7.48 (m, 5H), 7.42 (s, 1H), 7.17 (dd, J=8.0 Hz, 1.2 Hz, 1H), 7.13 (d, J=8.4 Hz, 2H), 6.88 (d, J=8.0 Hz, 2H), 5.81 (d, J=8.4 Hz, 1H), 3.06 (s, 3H), 2.67 (s, 2H), 2.20 (brs, 8H), 2.12 (s, 3H). HRMS m/z found 525.2371, calcd for $C_{30}H_{31}N_5O_4$ [M]$^+$ 525.2376.

To a suspension of crude 6-carboxylic acid 20 (1.0 equiv.), HBTU or TBTU (1.2 equiv.), HOBt (1.2 equiv.) in dimethylformamide was added DIPEA (16 equiv.) at room temperature. N,N-dimethylpropane-1,3-diamine (1.5 equiv.) was then added and continued stirred for 2 h. Volatiles were removed in vacuo and the obtained product was purified by column chromatography (neutral Al$_2$O$_3$, 0-10% methanol in CH$_2$Cl$_2$) or HPLC to afford the target molecule 2-oxoindoline-6-carboxamide 22. Major conformer $^1$H NMR (400 MHz, DMSO-d$_6$): δ 12.10 (s, 1H), 10.93 (s, 1H), 8.24 (t, J=5.2 Hz, 1H), 7.64-7.49 (m, 5H), 7.33 (d, J=1.6 Hz, 1H), 7.12 (d, J=8.4 Hz, 2H), 7.05 (dd, J=8.4 Hz, 1.6 Hz, 1H), 6.87 (d, J=8.4 Hz, 2H), 5.74 (d, J=8.0 Hz, 1H), 3.20 (q, J=8.0 Hz, 2H), 3.05 (s, 3H), 2.69 (s, 2H), 2.33-2.05 (m, 19H), 1.59 (m, 2H). HRMS m/z found 610.3494, calcd for $C_{35}H_{44}N_7O_3$ [M+H]$^+$ 610.3500.

(Z)—N-(3-Aminopropyl)-3-(((4-(N-methyl-2-(4-methylpiperazin-1-yl)acetamido)phenyl)amino)(phenyl)methylene)-2-oxoindoline-6-carboxamide (23). The title compound was synthesized using similar procedure as described for the synthesis of compound 22 by substituting tert-butyl (3-aminopropyl)carbamate for dimethylpropane-1,3-diamine followed by removal of Boc protecting with treatment of 20% TFA in dichloromethane at rt for 3 hr. Major conformer $^1$H NMR (400 MHz, DMSO-d$_6$): δ 12.15 (s, 1H), 10.98 (s, 1H), 8.37 (t, J=5.2 Hz, 1H), 7.72-7.50 (m, 7H), 7.35 (s, 1H), 7.16 (d, J=8.4 Hz, 2H), 7.08 (dd, J=8.0 Hz, 1.6 Hz, 1H), 6.89 (d, J=8.4 Hz, 2H), 5.74 (d, J=8.4 Hz, 1H), 3.48-2.69 (m, 20H), 1.74 (m, 2H). HRMS m/z found 582.3186, calcd for $C_{33}H_{40}N_7O_3$ [M+H]$^+$ 582.3187.

(Z)—N-Methyl-3-(((4-(N-methyl-2-(4-methylpiperazin-1-yl)acetamido)phenyl)amino)(phenyl)methylene)-2-oxoindoline-5-carboxamide (24). (Z)-3-(((4-(N-Methyl-2-(4-methylpiperazin-1-yl)acetamido)phenyl)amino)(phenyl)methylene)-2-oxoindoline-5-carboxylic acid (21) was synthesized using similar procedure as described for the synthesis of compound 20 by swapping indolinone 17 for inodolinone derivative 15. Major conformer $^1$H NMR (400 MHz, DMSO-d$_6$): δ 12.00 (s, 1H), 11.09 (s, 1H), 7.60-7.47 (m, 6H), 7.12 (d, J=8.4 Hz, 2H), 6.92 (d, J=8.0 Hz, 1H), 6.85 (d, J=8.8 Hz, 2H), 6.59 (s, 1H), 3.05 (s, 3H), 2.69 (s, 2H), 2.19 (brs, 8H), 2.11 (s, 3H). HRMS m/z found 526.2453, calcd for $C_{30}H_{32}N_5O_4$ [M+H]$^+$ 526.2449.

The title compound 24 was synthesized using similar procedure as described for the synthesis of compound 22 by substituting methylamine hydrochloride for dimethylpropane-1,3-diamine. Major conformer $^1$H NMR (400 MHz, DMSO-d$_6$): δ 12.03 (s, 1H), 10.97 (s, 1H), 7.93 (m, 1H), 7.62-7.46 (m, 5H), 7.39 (dd, J=8.4 Hz, 1.6 Hz, 1H), 7.11 (d, J=8.4 Hz, 2H), 6.85 (d, J=8.4 Hz, 1H), 6.83 (d, J=8.8 Hz, 2H), 6.53 (s, 1H), 3.05 (s, 3H), 2.69 (s, 2H), 2.63 (d, J=4.8 Hz, 3H), 2.19 (brs, 8H), 2.11 (s, 3H). HRMS m/z found 539.2782, calcd for $C_{31}H_{35}N_6O_3$ [M+H]$^+$ 539.2765.

(Z)—N,N-Dimethyl-3-(((4-(N-methyl-2-(4-methylpiperazin-1-yl)acetamido)phenyl)amino)(phenyl)methylene)-2-oxoindoline-5-carboxamide (25). The title compound was synthesized using similar procedure as described for the synthesis of compound 22 by substituting dimethylamine hydrochloride for dimethylpropane-1,3-diamine. Major conformer $^1$H NMR (400 MHz, DMSO-d$_6$): δ 12.03 (s, 1H), 10.94 (s, 1H), 7.62-7.48 (m, 5H), 7.11 (d, J=8.4 Hz, 2H), 7.03 (dd, J=8.0 Hz, 1.6 Hz, 1H), 6.88 (d, J=8.0 Hz, 1H), 6.84 (d, J=8.0 Hz, 2H), 5.86 (s, 1H), 3.05 (s, 3H), 2.76 (s, 6H), 2.69 (s, 2H), 2.18 (brs, 8H), 2.10 (s, 3H). HRMS m/z found 553.2930, calcd for $C_{32}H_{37}N_6O_3$ [M+H]$^+$ 553.2922.

MELK Assays and Selectivity Screening
Inhibitor Library Screening

MELK and its substrate, Bcl-G were both recombinantly expressed and purified for use in screening assays (See Methods). 752 compounds from an in-house curated inhibitor library were subjected to a p81-based kinase assay. 10 nM MELK 340 and 10 μM Bcl-G$_L$ in kinase assay buffer (50 mM HEPES pH 7.5, 100 mM KCl, 0.1 mM EDTA, 0.1 mM EGTA, 10 mM MgCl$_2$, 10 μg/mL BSA) with 10 mM DTT were added to either 10 μM or 1 μM inhibitor aliquoted into 96 well plates (final 1% DMSO). The mixture was incubated at room temperature for 30 minutes prior to initiation of the assay with 40 μM γ-$^{32}$P-ATP (100-1000 CPM/pmol). 40 μL aliquots were spotted onto a p81 96 well filter plate (Unifilter, Whatman), quenched, and washed with 75 mM O-phosphoric acid 8 times, followed by a final wash with acetone for drying. Wells were then filled with scintillation fluid, sealed, and quantified using a MicroBeta TriLux liquid scintillation counter (PerkinElmer). Each inhibitor plate was assayed in duplicate, with at least 4 wells without MELK to establish background and at least 4 wells without inhibitor as a negative control. All readings were corrected for background signal based on the average counts from the wells without enzyme. Percent inhibition, defined as [100−(CPM+inhibitor/average CPM of positive controls)*100], was determined first at 10 μM inhibitor. The top 50 inhibitors were then re-screened in duplicate at 1 μM.

Characterization of Hits and Compound 15 (MELK-In-1) Derivatives

The top 10 hits from the 1 μM screening and derivatives of MELK-In-1 were subjected to the same assay conditions with varied inhibitor concentrations (0.0005-50 μM) to generate a dose-response curve and IC$_{50}$. At set time points (0.25, 0.5, 1, 1.5, and 2 min for assays containing 10 nM MELK and 1, 2, 4, 6, and 10 min for assays containing 1 nM MELK), 30 μL aliquots were taken from each reaction and spotted onto 2×2 cm squares of p81 paper. Papers were washed 4 times in 75 mM O-phosphoric acid and once in acetone. Labeled protein was quantified by its associated CPM determined on a Packard 1500 scintillation counter at a sigma value of 2. CPM were translated into nmol $^{32}$P incorporated using Equation 1.

$$nmol\ P = \frac{(CPM/3)(1\times10^5)}{(1\times10^{-9})\times \text{Specific Activity}}$$ Equation 1

Rates in the presence of each concentration of inhibitor were determined by plotting nmol $^{32}$P incorporated vs. time. These rates were normalized to rates obtained without inhibitor, and data were plotted in terms of fractional activity. In most cases, data were fit to Equation 2. If the IC$_{50}$ approached the amount of enzyme used in the assay, data were re-fit to the equation for tight-binding inhibitors (the Morrison equation, Equation 2). To validate IC$_{50}$ values for MELK-In-7, 8, 9, and 11, assays were repeated in the presence of 1 nM enzyme instead of 10 nM. Data were transformed as discussed and fit to Equation 3.

$$\frac{v_i}{v_0} = 1 - \frac{[I]}{([I]+IC_{50})},$$ Equation 2 where $v_i$ is the observed rate with inhibitor, $v_0$ is the rate in the absence of inhibitor, [I] is inhibitor concentration in nM, and IC$_{50}$ is the concentration of inhibitor at which half maximal change in $v_0$ is observed.

$$\frac{v_i}{v_0} = 1 - \frac{(E_T + [I] + IC_{50}) - \sqrt{E_T + [I] + IC_{50} - 4E_T[I]}}{2E_T},$$ Equation 3 where $E_T$ was constrained to the total enzyme in the assay.

IC$_{50}$ values were used to estimate each inhibitor's K$_i$ using the Cheng-Prusoff relationship for competitive inhibitors (Equation 4). Apparent K$_M^{ATP}$ for MELK was experimentally determined for screening and derivative conditions by performing two independent dose-response curves with varied ATP (0-1.28 mM). The value obtained, K$_M^{ATP}$=6±1.5 μM, was used as a parameter in Equation 4 in the course of fitting the K$_i$.

$$K_i = IC_{50} / \left(1 + \frac{[ATP]}{K_M^{ATP}}\right)$$ Equation 4

Selectivity Screening

Candidates for inhibitor selectivity characterization were chosen based on an initial single-timepoint commercial kinome profiling screen performed with inhibitor 17 (MELK-In-7) (KinomeScan, DiscoveRx, San Diego, Calif.), primary sequence relation to MELK, and laboratory availability. CHK1 and NUAK1 were purchased from Signal-Chem (Vancouver, BC). The NUAK2, CHK, and SAMS peptides were purchased from BioSyn (Lewisville, Tex.). The sequence of CHK and NUAK2 peptides are described elsewhere (Sanchez Y, et al. Science (New York, N.Y.). 1997; 277(5331):1497-1501; Scott J W, et al. Sci Rep. 2015; 5:14436). ERK2, AMPK, CAMKK2, and Ets1 were produced in house as previously described (Waas W F, Dalby K N. *The Journal of biological chemistry.* 2002; 277(15): 12532-12540; Neumann D, et al. *Protein Expr Purif.* 2003; 30(2):230-237; Waas W F, Dalby K N. Protein Expr Purif. 2001; 23(1):191-197). Apparent K$_M$ values for ATP under specific assay conditions were determined using respective experimental conditions in Table 8 with varied ATP (0-1.28 mM). All selectivity dose-response assays were performed in kinase assay buffer (see Inhibitor Library Screen) with 2 mM DTT and 100 μM γ-$^{32}$P-ATP with additional conditions listed in Table 8. IC$_{50}$ and K$_M^{ATP}$ values were subsequently used to calculate K$_i$ (Equation 4). Relative selectivity was determined by comparing K$_i^{Enzyme}$/K$_i^{MELK}$ (termed φ in Table 7). All IC$_{50}$ and/or K$_i$ data were fit using Prism® (GraphPad) using equations 2, 3, and 4, as appropriate. Standard error from linear regression data was propagated internally in Prism and taken into account in nonlinear regression to determine IC$_{50}$ or K$_i$.

Cell Culture and Reagents

HCC70, BT-549, and SUM159 human TNBC cell lines and MCF10A human breast epithelial cell line were purchased from American Type Culture Collection. The murine 4T1-Luc TNBC cells were purchased from PerkinElmer. HCC70, BT-549, and 4T1-Luc cells were maintained in RPMI 1640 medium (Life Technologies Inc., Grand Island, N.Y., USA) and MDA-MB-231-LM2 cells in Dulbecco's modified Eagle's medium/F12 medium (Life Technologies Inc., Grand Island, N.Y., USA), both types of medium supplemented with FBS (10%) and antibiotic/antimycotic (1%). SUM159 cells were maintained in Ham's F-12 medium (Life Technologies Inc., Grand Island, N.Y., USA) supplemented with FBS (5%), antibiotic/antimycotic (1%), insulin (5 μg/mL), and hydrocortisone (1 μg/mL). MCF10A cells were maintained in Dulbecco's modified Eagle's medium/F12 medium supplemented with horse serum (10%), antibiotic/antimycotic (1%), insulin (10 μg/mL), EGF (20 ng/mL), cholera toxin (100 ng/mL), and hydrocortisone (500 μg/mL). All cell lines used in this study were validated by the Characterized Cell Line Core Facility at MD Anderson Cancer Center by using a short tandem repeat method based on primer extension to detect single base deviations.

Western Blotting

Western blotting was done as described previously (Bartholomeusz C, et al. Clinical cancer research: an official journal of the American Association for Cancer Research. 2010; 16(6):1802-1811). Proteins of interest were probed using the following primary antibodies (1:1000 dilution) purchased from Cell Signaling Technology (Danvers, Mass., USA) or other suppliers as indicated: anti-fibronectin (1:500 dilution; BD Transduction), anti-vimentin, anti-E-cadherin (1:1000 dilution; BD Transduction), anti-β-catenin, anti-snail (1:1000 dilution; Santa Cruz), and anti-α-tubulin (clone DM1A, T9026, Sigma-Aldrich, St. Louis, Mo., USA). Secondary antibodies were horseradish peroxidase-conjugated IgG (1:10,000 dilution; Invitrogen) for chemiluminescent signal detection and the corresponding Alexa Fluor-conjugated IgG (1:5000 dilution; Invitrogen) for fluorescence signal detection.

Cell Proliferation Assay

Cell proliferation was determined using the CellTiter-Blue viability assay as described previously (Gloeckner H, et al. Journal of immunological methods. 2001; 252(1-2): 131-138). Cells were seeded in 96-well plates and treated the next day with MELK inhibitors (0-20 μM). At 72 h after MELK inhibitor treatment, optical density at 595 nm was determined.

Cloning and Recombinant Expression of MELK and Bcl-G

The plasmid containing full length MELK (GenBank Accession number NM_014791) was a generous gift of Dr. Garth Powis (Sanford Burnham Prebys). The catalytic domain of MELK (amino acids 1-340) was subcloned into pET28a using the NdeI/XhoI restriction sites. Insertion and sequence were verified by DNA sequencing. Plasmids were transformed into BL21(DE3) *E. coli*, grown in TB media to an $OD_{595}$ of 0.6, and induced with 0.5 mM IPTG. Cultures were grown for 5 hours at 25° C., harvested by centrifugation at 15,000 rpm at 4° C. for 30 minutes, and flash frozen for storage at −80° C. Pellets were resuspended in Ni-NTA lysis buffer (20 mM Tris pH 8, 0.5 M NaCl, 0.03% Brij-35, 1% Triton X-100, 5 mM imidazole, 1 mM benzamidine, 0.1 mM TPCK, 0.1 mM PMSF, and 0.1% ß-mercaptoethanol) and sonicated. Lysates were cleared by centrifugation and supernatants incubated with nickel beads (Qiagen) at 4° C. for 1 hour. Beads were washed (20 mM Tris pH 8, 0.03% Brij-35, 10 mM imidazole, 1 mM benzamidine, 0.1 mM TPCK, 0.1 mM PMSF, and 0.1% ß-mercaptoethanol) and hexahistadine-tagged MELK was subsequently eluted (20 mM Tris pH 8, 0.03% Brij-35, 250 mM imidazole, 1 mM benzamidine, 0.1 mM TPCK, 0.1 mM PMSF, and 0.1% ß-mercaptoethanol). Nickel eluates were subsequently dialyzed into equilibration buffer (20 mM Tris pH 8, 0.1 mM EDTA, 0.1 mM EGTA, 0.1% ß-mercaptoethanol), loaded onto an anion exchange column (MonoQ 10/100, GE Healthcare), and eluted over a 17 column volume linear gradient of 0-0.5 M NaCl. Fractions were analyzed by SDS-PAGE. Protein was dialyzed into storage buffer (25 mM HEPES pH 7.5, 50 mM KCl, 0.1 mM EDTA, 0.1 mM EGTA, 2 mM DTT, 10% glycerol) and stored at −80° C.

Full-length cDNA for Bcl-$G_L$ (GenBank Accession number BC025778) was purchased from Open Biosystems and subcloned into pET28a using LIC. After insertion and sequence verification, plasmids were transformed into BL21 (DE3) *E. coli*, cultured in TB media to an $OD_{595}$ of 0.6, and induced with 50 μM IPTG. Flasks were incubated overnight (18 hours) at 18° C. and harvested and purified using nickel affinity and anion exchange columns as described for MELK.

TABLE 8

Conditions used in selectivity screening.

| Enzyme | Conditions | Time Course | Apparent $K_M^{ATP}$ ± SE (μM) |
|---|---|---|---|
| AMPK | 10 nM AMPK, 100 μM SAMS, 50 μM AMP | 0.25-2 min | 98 ± 8.4 |
| CAMKK2 | 50 nM CAMKK2, 200 μM NUAK2 peptide, 150 μM total Ca2+, 1 μM calmodulin | 0.5-6 min | 265 ± 25 |
| CHK1 | 5 nM CHK1, 100 μM CHK peptide | 0.25-4 min | 125 ± 2.5 |
| ERK2 | 1 nM ERK2, 20 μM Ets-1 | 0.25-4 min | 98 ± 14 |
| NUAK1 | 10 nM NUAK1, 100 μM CHK peptide | 0.25-4 min | 60 ± 3.6 |

REFERENCES CITED IN THIS EXAMPLE

The disclosures of all articles and references, including patent applications and publications, are incorporated by reference for all purposes.
1. Gil M, et al. *Gene.* 1997; 195(2):295-301.
2. Beullens M, et al. *The Journal of biological chemistry.* 2005; 280(48):40003-40011.
3. Blot J, et al. *Dev Biol.* 2002; 241(2):327-338.
4. Davezac N, et al. *Oncogene.* 2002; 21(50):7630-7641.
5. Joshi K, et al. *Stem cells (Dayton, Ohio).* 2013.
6. Saito R, et al. *Cancer science.* 2012; 103(1):42-49.
7. Lin M L, et al. *Breast cancer research: BCR.* 2007; 9(1):R17.
8. Pickard M R, et al. *Biochimica et biophysica acta.* 2011; 1812(9):1146-1153.
9. Vulsteke V, et al. *The Journal of biological chemistry.* 2004; 279(10):8642-8647.
10. Heyer B S, et al. *Molecular reproduction and development.* 1997; 47(2):148-156.
11. Wang Y, et al. *eLife.* 2014: e01763.
12. Nakano I, et al. *The Journal of cell biology.* 2005; 170(3):413-427.
13. Niesler C U, et al. *Experimental physiology.* 2007; 92(1):207-217.
14. Hebbard L W, et al. *Cancer research.* 2010; 70(21): 8863-8873.
15. Nakano I, et al. *Neuro-oncology.* 2011; 13(6):622-634.
16. Nakano I, et al. *Journal of neuroscience research.* 2008; 86(1):48-60.
17. Gray D, et al. *Cancer research.* 2005; 65(21):9751-9761.
18. Ryu B, et al. *PloS one.* 2007; 2(7):e594.
19. Marie S K, et al. *International journal of cancer. Journal international du cancer.* 2008; 122(4):807-815.
20. Li Y, et al. *Lung cancer (Amsterdam, Netherlands).* 2013.
21. Rajkumar T, et al. *BMC cancer.* 2011; 11:80.
22. Risinger J I, et al. *Frontiers in oncology.* 2013; 3:139.
23. Kappadakunnel M, et al. *Journal of neuro-oncology.* 2010; 96(3):359-367.
24. Komatsu M, et al. *International journal of oncology.* 2013; 42(2):478-506.
25. Al-Ejeh F, et al. *Oncogenesis.* 2014; 3:e100.
26. Marie S K, et al. *Proteome Sci.* 2016; 14:6.
27. Seong H A, et al. *The Journal of biological chemistry.* 2010; 285(40):30959-30970.
28. Miduturu C V, et al. *Chemistry & biology.* 2011; 18(7): 868-879.
29. Uitdehaag J C, et al. *Br J Pharmacol.* 2012; 166(3):858-876.
30. Mathea S, et al. *ACS Chem Biol.* 2016; 11(6):1595-1602.
31. Elkins J M, et al. *Nat Biotechnol.* 2016; 34(1):95-103.
32. Prakash C R, et al. *Mini reviews in medicinal chemistry.* 2012; 12(2):98-119.
33. Aronov A M, et al. *Journal of medicinal chemistry.* 2008; 51(5):1214-1222.
34. Canevari G, et al. *Biochemistry.* 2013; 52(37):6380-6387.
35. Toure B B, et al. *J Med Chem.* 2016; 59(10):4711-4723.
36. Furtmann N, et al. *J Med Chem.* 2015; 58(1):252-264.
37. Roth G J, et al. *J Med Chem.* 2009; 52(14):4466-4480.
38. Zhao B, et al. *The Journal of biological chemistry.* 2002; 277(48):46609-46615.
39. Beke L, et al. *Biosci Rep.* 2015.
40. Lehmann B D, et al. *The Journal of clinical investigation.* 2011; 121(7):2750-2767.
41. Kao J, et al. *PloS one.* 2009; 4(7):e6146.
42. Heckel A B, et al. Inventor; Boehringer Ingelheim International GmbH (Ingelheim, DE), assignee. Cycloalkyl-containing 5-acylindolinones, the preparation thereof and their use as medicaments. 2007.
43. Sanchez Y, et al. *Science (New York, N.Y.).* 1997; 277(5331):1497-1501.
44. Scott J W, et al. *Sci Rep.* 2015; 5:14436.
45. Waas W F, Dalby K N. *The Journal of biological chemistry.* 2002; 277(15):12532-12540.
46. Neumann D, et al. *Protein Expr Purif.* 2003; 30(2):230-237.
47. Waas W F, Dalby K N. *Protein Expr Purif.* 2001; 23(1):191-197.
48. Bartholomeusz C, et al. *Clinical cancer research: an official journal of the American Association for Cancer Research.* 2010; 16(6):1802-1811.

Example 2. Synthesis of Indolinone Derivatives 91-108

A number of indolinone derivatives were synthesized in order to improve potency and selectivity. (See Compounds 91-108). The general synthetic routes are outlined in Schemes 3 and 4. The key intermediates 79-90 were prepared via modified Bischler-napieralski reactions of 2-alkynylaryl isocyanates 67-78 with iron trichloride (Cantagrel, G., et al. J. Org. Lett., 2009, 11, 4262-4265).

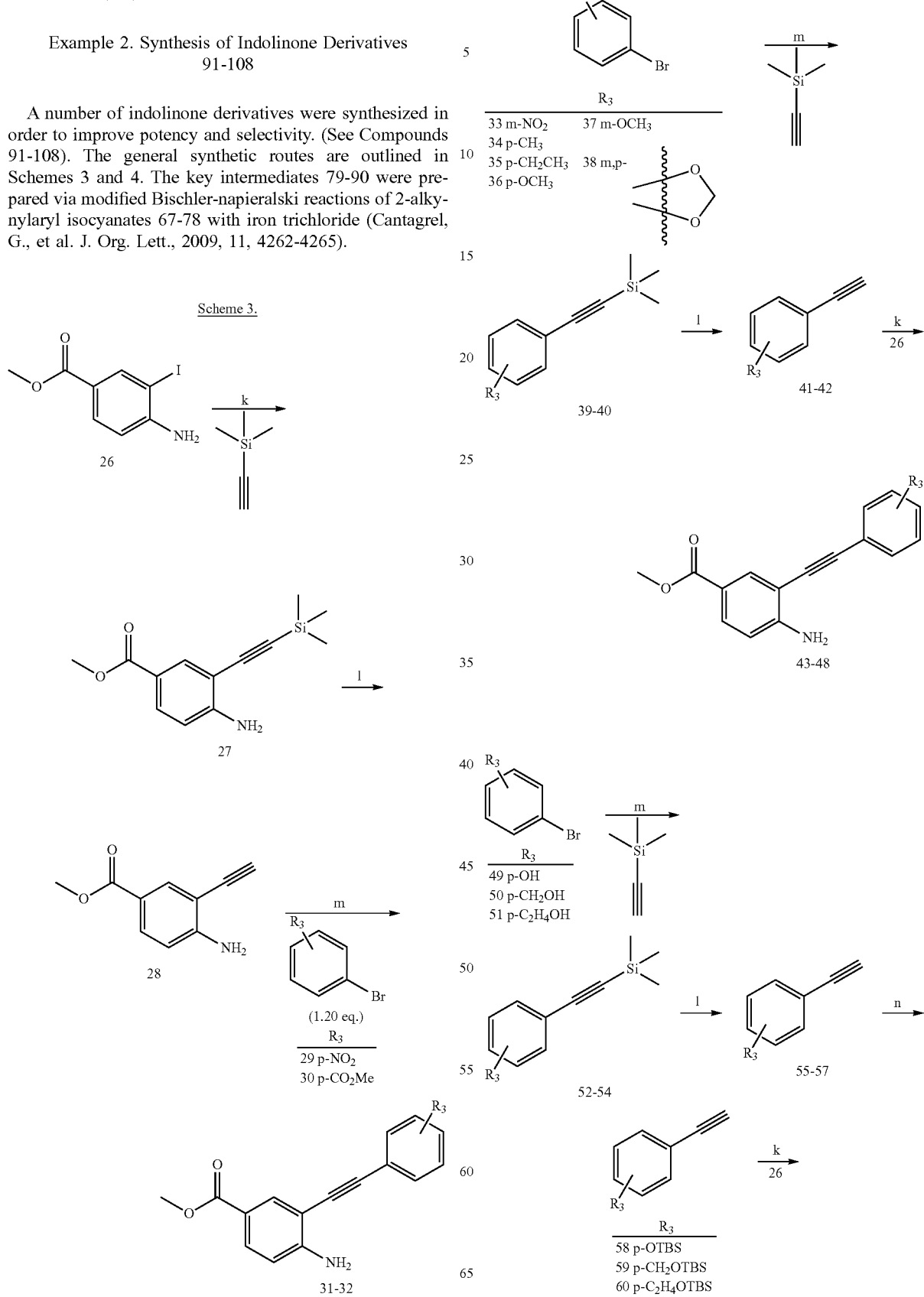

Scheme 3.

69
-continued

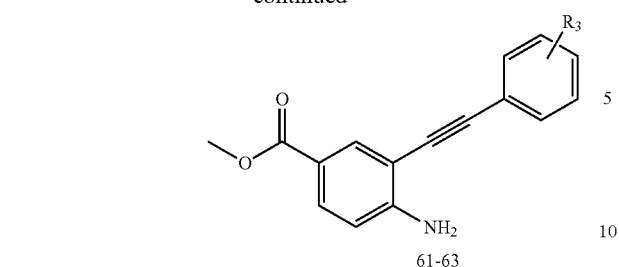
61-63

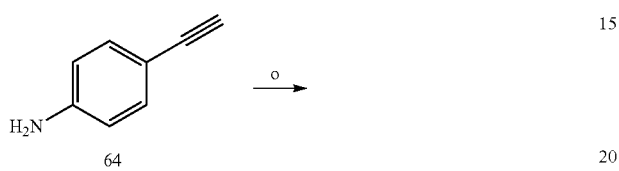
64

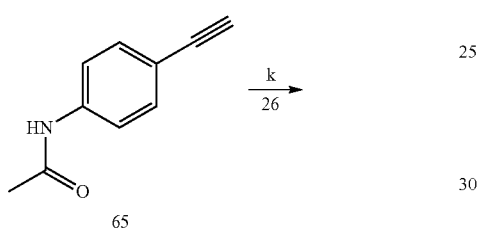
65

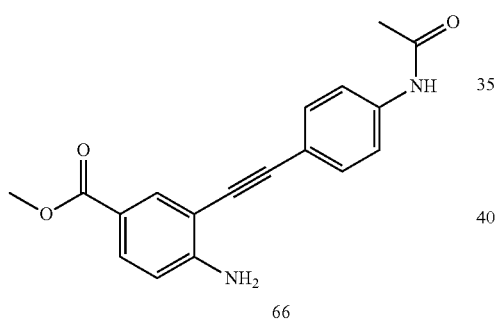
66

Synthesis of intermediate. Reagents and conditions: (k) PdCl$_2$(PPh$_3$)$_2$, CuI, TEA, toluene, rt, overnight, 65%—quant.; (l) TBAF, THF, rt, 2 h, 98%—quant.; (m) PdCl$_2$(PPh$_3$)$_2$, CuI, TEA, THF, rt, overnight, 85%—quant.; (n) imidazole, DMF, rt, overnight, (o) acetic anhydride, DCM, rt, 6 h, 84%.

Scheme 4.

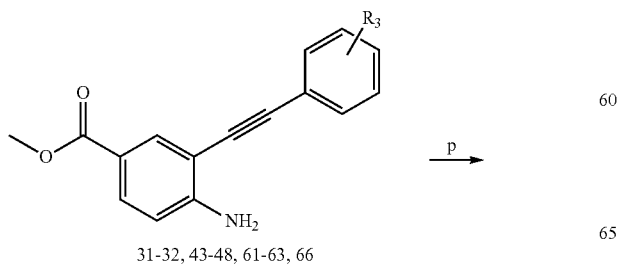
31-32, 43-48, 61-63, 66

70
-continued

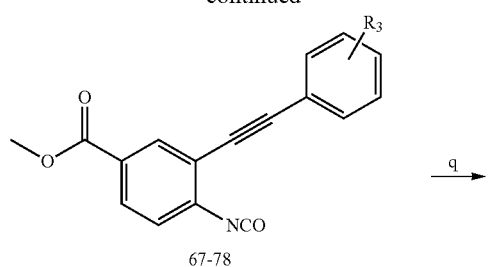
67-78

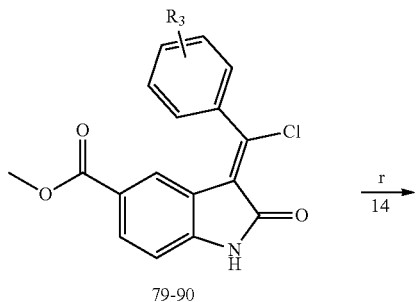
79-90

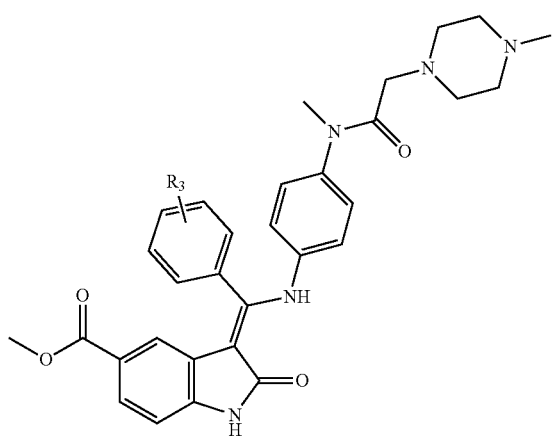

| | R$_3$ | | R$_3$ |
|---|---|---|---|
| 91 | p-NO$_2$ | 99 | p-OTBS |
| 92 | p-CO$_2$Me | 100 | p-CH$_2$OH |
| 93 | m-NO$_2$ | 101 | p-C$_2$H$_4$OTBS |
| 94 | p-CH$_2$CH$_3$ | 102 | p-NHCOCH$_3$ |
| 96 | p-OCH$_3$ | 103 | p-NH$_2$ |
| 97 | m-OCH$_3$ | 104 | m-NH$_2$ |
| 98 | m,p- | 105 | p-OH |
| | | 106 | p-C$_2$H$_4$OH |

71
-continued

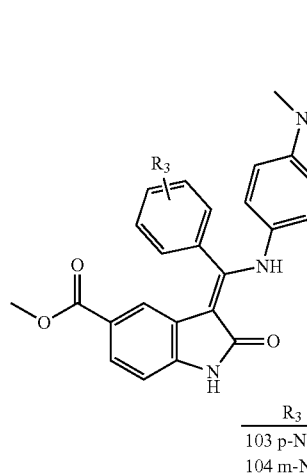

| R₃ | |
|---|---|
| 103 | p-NH₂ |
| 104 | m-NH₂ |

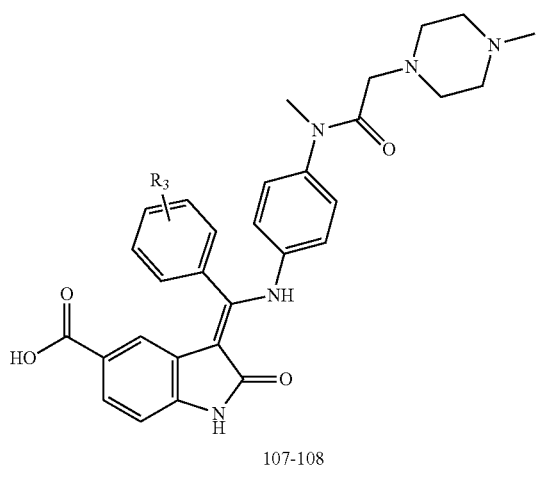

107-108

Synthesis of intermediate. Reagents and conditions: (p) triphosgene, TEA, toluene, rt, 3 h; (q) FeCl₃, DCM, rt, overnight, 19%—quant. (two steps from p and q); (r) ethanol, reflux, overnight, 34%—quant.; (s) SnCl₂, ethanol, 70° C., overnight, 76%—quant.; (i) 1N aq. NaOH, methanl/1,4-dioxane, 80° C., 6 h, 80-96%.

Stereoselectively converted final indolinone (Z)-3-(aminoarylmethylene)oxindoles analogs were synthesized by addition of compound 14 to 3-(arylchloromethylene)oxindoles 79-90. which can be subsequently stereoselectively converted to (Z)-3-(aminoarylmethylene)oxindoles (scheme 4). Additional amino analogs 111 and 112 were prepared from the corresponding nitro derivatives 99 and 101 through reduction by tin (II) chloride. Alcohol analogs 113 and 114 were also obtained via TBS-deprotection using TBAF. 5-acid derivatives 107-108 were synthesized through hydrolysis using aqueous 1N NaOH (Scheme 4).

72
Methyl 4-amino-3-((trimethylsilyl)ethynyl)benzoate (27)

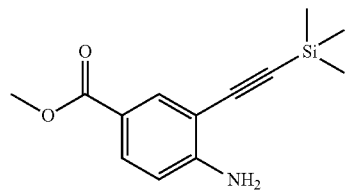

A combined suspension of methyl 4-amino-3-((trimethylsilyl)ethynyl)benzoate (1.50 g, 5.41 mmol), copper (I) iodide (21 mg, 0.11 mmol), bis(triphenylphosphine)palladium(II) dichloride (76 mg, 0.11 mmol), and ethynyltrimethylsilane (0.90 mL, 6.50 mmol) were stirred in toluene and TEA (1/1, 46 mL) at ambient temperature for overnight. The reaction solvent was evaporated under reduced pressure, and the residue was purified by column chromatography with hexane/ethyl acetate (5/1, v/v) to obtain the compound 27 as a white solid (1.33 g, 99% yield):

$^1$H NMR (400 MHz, CDCl₃) δ 8.00 (d, J=2.0 Hz, 1H), 7.77 (dd, J=8.6, 2.0 Hz, 1H), 6.65 (d, J=8.5 Hz, 1H), 4.69 (bs, 2H), 3.83 (s, 3H), 0.26 (s, 9H);

$^{13}$C NMR (100 MHz, CDCl₃) δ 166.6, 152.0, 134.7, 131.7, 119.2, 113.2, 107.0, 100.6, 100.6, 51.8, 0.2.

Methyl 4-amino-3-ethynylbenzoate (28)

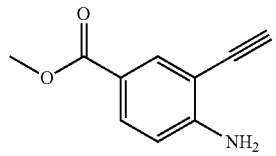

To a solution of methyl 4-amino-3-((trimethylsilyl)ethynyl)benzoate (1.34 g, 5.42 mmol) in THF (11 mL) was added tetrabutylammonium fluoride solution (5.96 ml, 1M in THF). After addition, the reaction was stirred at ambient temperature for 2 h. All the volatile solvent was removed under reduced pressure, and the residue was dissolved in DCM (20 ml). Water (15 mL) was added, and the aqueous layer was extracted with DCM (15 mL×2). The combined organic layer was washed with brine (30 mL), dried over Na₂SO₄, and filtered. The organic layer was concentrated under reduced pressure and the residue was purified by silica gel chromatography, by column chromatography with hexane/ethyl acetate (2/1, v/v) to obtain the compound 28 as a white solid (949 mg, quant. yield):

$^1$H NMR (400 MHz, CDCl₃) δ 8.01 (d, J=2.0 Hz, 1H), 7.79 (dd, J=8.6, 2.0 Hz, 1H), 6.65 (d, J=8.6 Hz, 1H), 4.74 (bs, 2H), 3.83 (s, 3H), 3.39 (s, 1H);

$^{13}$C NMR (100 MHz, CDCl₃) δ 166.6, 152.3, 134.9, 131.9, 119.1, 113.3, 105.8, 83.1, 76.8, 51.8, 29.8.

Methyl 4-amino-3-((4-nitrophenyl)ethynyl)benzoate (31)

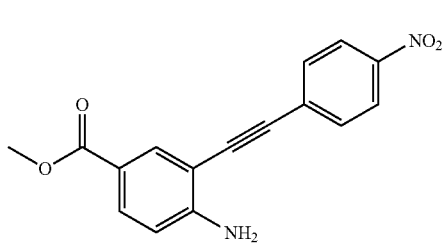 [SMILES: COC(=O)c1ccc(N)c(C#Cc2ccc([N+](=O)[O-])cc2)c1]

A suspension of methyl 4-amino-3-ethynylbenzoate (1.01 g, 5.78 mmol), 1-bromo-4-nitrobenzene (1.40 g, 6.93 mmol), copper (I) iodide (55 mg, 0.29 mmol), bis(triphenylphosphine)palladium(II) dichloride (203 mg, 0.29 mmol), TEA (2.42 ml, 1.73 mmol) were stirred in THF (10 mL) at ambient temperature for overnight. The reaction solvent was evaporated under reduced pressure, and the residue was purified by column chromatography with hexane/ethyl acetate (1/1, v/v) to obtain the compound 31 as a yellow solid (1.71 g, quant. yield):

$^1$H NMR (400 MHz, DMSO-d$_6$) δ 8.27 (d, J=8.3 Hz, 2H), 7.95 (d, J=8.3 Hz, 2H), 7.89 (d, J=2.1 Hz, 1H), 7.70 (dd, J=8.7, 2.1 Hz, 1H), 6.78 (d, J=8.3 Hz, 1H), 6.60 (bs, 2H), 3.77 (s, 3H).

Methyl 4-amino-3-((4-(methoxycarbonyl)phenyl)ethynyl)benzoate (32)

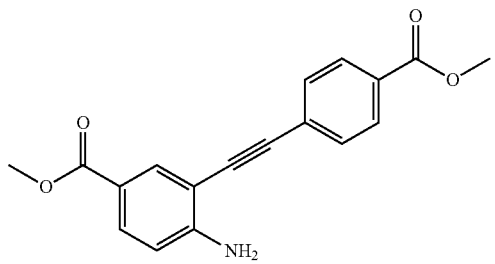

A suspension of methyl 4-amino-3-ethynylbenzoate (2.04 g, 11.65 mmol), methyl 4-bromobenzoate (3.01 g, 13.97 mmol), copper (I) iodide (111 mg, 0.58 mmol), bis(triphenylphosphine)palladium(II) dichloride (409 mg, 0.58 mmol), TEA (4.87 ml, 34.93 mmol) were stirred in THF (19 mL) at ambient temperature for overnight. The reaction solvent was evaporated under reduced pressure, and the residue was purified by column chromatography with hexane/ethyl acetate (1/1, v/v) to obtain the compound 32 as a brown solid (3.05 g, 85% yield):

$^1$H NMR (400 MHz, DMSO-d$_6$) δ 87.98 (d, J=8.1 Hz, 2H), 7.86 (d, J=2.1 Hz, 1H), 7.81 (d, J=8.7 Hz, 2H), 7.68 (dd, J=8.7, 2.1 Hz, 1H), 6.77 (d, J=8.7 Hz, 1H), 6.50 (s, 2H), 3.87 (s, 3H), 3.77 (s, 3H);

$^{13}$C NMR (100 MHz, DMSO-d$_6$) δ 165.7, 165.6, 153.8, 134.3, 131.6, 131.5, 129.2, 128.8, 127.6, 116.3, 113.4, 104.1, 93.4, 88.9, 52.3, 51.5.

Trimethyl((3-nitrophenyl)ethynyl)silane (39)

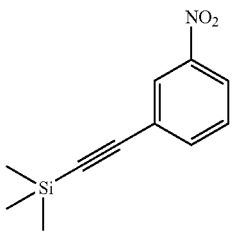

A suspension of 1-iodo-3-nitrobenzene (3.00 g, 12.05 mmol), ethynyltrimethylsilane (2.00 mL, 14.46 mmol), copper (I) iodide (115 mg, 0.60 mmol), bis(triphenylphosphine)palladium(II) dichloride (423 mg, 0.60 mmol), TEA (5.04 ml, 36.14 mmol) were stirred in THF (20 mL) at ambient temperature for overnight. The reaction solvent was evaporated under reduced pressure, and the residue was purified by column chromatography with hexane/ethyl acetate (10/1, v/v) to obtain the compound 39 (2.64 g, quant. yield):

$^1$H NMR (400 MHz, CDCl$_3$) δ 8.31 (t, J=2.0 Hz, 1H), 8.16 (dd, J=8.3, 1.1 Hz, 1H), 7.75 (dt, J=7.7, 1.3 Hz, 1H), 7.49 (t, J=8.0 Hz, 1H), 0.27 (s, 9H);

$^{13}$C NMR (100 MHz, CDCl$_3$) δ 137.7, 129.4, 126.9, 125.1, 123.3, 102.3, 97.8, −0.1.

(Benzo[d][1,3]dioxol-5-ylethynyl)trimethylsilane (40)

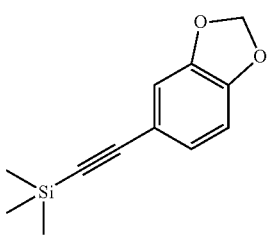

A suspension of 5-iodobenzo[d][1,3]dioxole (3.00 g, 12.10 mmol), ethynyltrimethylsilane (2.01 mL, 14.52 mmol), copper (I) iodide (115 mg, 0.61 mmol), bis(triphenylphosphine)palladium(II) dichloride (424 mg, 0.61 mmol), TEA (5.06 ml, 36.29 mmol) were stirred in THF (20 mL) at ambient temperature for overnight. The reaction solvent was evaporated under reduced pressure, and the residue was purified by column chromatography with hexane/ethyl acetate (10/1, v/v) to obtain the compound 40 (2.64 g, quant. yield):

$^1$H NMR (400 MHz, CDCl$_3$) δ 6.98 (dd, J=8.1, 1.6 Hz, 1H), 6.89 (d, J=1.6 Hz, 1H), 6.70 (d, J=8.0 Hz, 1H), 5.92 (s, 2H), 0.23 (s, 9H);

$^{13}$C NMR (100 MHz, CDCl$_3$) δ 148.1, 147.4, 126.8, 116.5, 111.9, 108.4, 105.1, 101.4, 92.3, 0.1.

1-Ethynyl-3-nitrobenzene (41)

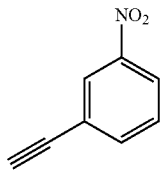

To a solution of trimethyl((3-nitrophenyl)ethynyl)silane (4.24 g, 19.34 mmol) in THF (39 mL) was added tetrabutylammonium fluoride solution (21.27 ml, 1M in THF). After addition, the reaction was stirred at ambient temperature for 2 h. All the volatile solvent was removed under reduced pressure, and the residue was dissolved in DCM (20 ml). Water (15 mL) was added, and the aqueous layer was extracted with DCM (15 mL×2). The combined organic layer was washed with brine (30 mL), dried over $Na_2SO_4$, and filtered. The organic layer was concentrated under reduced pressure and the residue was purified by silica gel chromatography, by column chromatography with hexane/ethyl acetate (20/1, v/v) to obtain the compound 41 as a yellow solid (1.77 mg, quant. yield):

$^1$H NMR (400 MHz, $CDCl_3$) δ 8.31 (t, J=1.9 Hz, 1H), 8.20 (dd, J=8.3, 1.1 Hz, 1H), 7.79 (dt, J=7.7, 1.3 Hz, 1H), 7.53 (t, J=8.0 Hz, 1H), 3.24 (s, 1H);

$^{13}$C NMR (100 MHz, $CDCl_3$) δ 137.9, 129.5, 127.0, 124.0, 123.6, 81.2, 80.0.

5-Ethynylbenzo[d][1,3]dioxole (42)

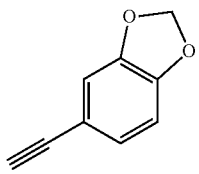

To a solution of (benzo[d][1,3]dioxol-5-ylethynyl)trimethylsilane (3.77 g, 17.27 mmol) in THF (35 mL) was added tetrabutylammonium fluoride solution (19.00 ml, 1M in THF). After addition, the reaction was stirred at ambient temperature for 2 h. All the volatile solvent was removed under reduced pressure, and the residue was dissolved in DCM (20 ml). Water (15 mL) was added, and the aqueous layer was extracted with DCM (15 mL×2). The combined organic layer was washed with brine (30 mL), dried over $Na_2SO_4$, and filtered. The organic layer was concentrated under reduced pressure and the residue was purified by silica gel chromatography, by column chromatography with hexane/ethyl acetate (20/1, v/v) to obtain the compound 42 as a brown solid (1.74 mg, 98% yield):

$^1$H NMR (400 MHz, $CDCl_3$) δ 7.00 (dd, J=8.0, 1.6 Hz, 1H), 6.91 (d, J=1.6 Hz, 1H), 6.71 (d, J=8.0 Hz, 1H), 5.92 (s, 2H), 2.98 (s, 1H);

$^{13}$C NMR (100 MHz, $CDCl_3$) δ 148.3, 147.4, 126.8, 115.2, 112.0, 108.4, 101.4, 83.6, 75.7.

Methyl 4-amino-3-((3-nitrophenyl)ethynyl)benzoate (43)

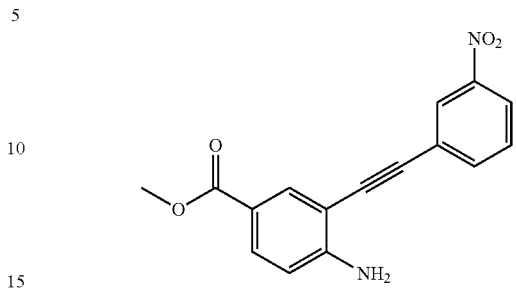

A combined suspension of methyl 4-amino-3-iodobenzoate (2.78 g, 10.04 mmol), copper (I) iodide (38 mg, 0.20 mmol), bis(triphenylphosphine)palladium(II) dichloride (141 mg, 0.20 mmol), and 1-ethynyl-3-nitrobenzene (1.77 g, 12.05 mmol) were stirred in toluene and TEA (1/1, 54 mL) at ambient temperature for overnight. The reaction solvent was evaporated under reduced pressure, and the residue was purified by column chromatography with hexane/ethyl acetate (3/1, v/v) to obtain the compound 43 as a yellow solid (2.33 g, 78% yield):

$^1$H NMR (400 MHz, DMSO-$d_6$) δ 8.62 (t, J=1.9 Hz, 1H), 8.22 (dd, J=8.3, 1.1 Hz, 1H), 8.08 (dt, J=7.7, 1.3 Hz, 1H), 7.90 (d, J=2.3 Hz, 1H), 7.70 (q, J=8.0 Hz, 1H), 7.69 (d, J=8.7 Hz, 1H), 6.77 (d, J=8.7 Hz, 1H), 6.60 (s, 2H), 3.77 (s, 3H);

$^{13}$C NMR (125 MHz, DMSO-$d_6$) δ 165.6, 153.7, 147.9, 137.5, 134.4, 131.6, 130.1, 125.9, 124.4, 123.0, 116.2, 113.4, 103.8, 91.9, 88.1, 51.5.

Methyl 4-amino-3-(p-tolylethynyl)benzoate (44)

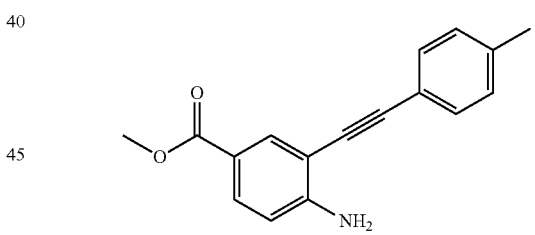

A combined suspension of methyl 4-amino-3-iodobenzoate (2.50 g, 9.02 mmol), copper (I) iodide (35 mg, 0.18 mmol), bis(triphenylphosphine)palladium(II) dichloride (127 mg, 0.18 mmol), and 1-ethynyl-4-methylbenzene (1.37 mL, 10.83 mmol) were stirred in toluene and TEA (1/1, 76 mL) at ambient temperature for overnight. The reaction solvent was evaporated under reduced pressure, and the residue was purified by column chromatography with hexane/ethyl acetate (5/1, v/v) to obtain the compound 44 as a white solid (2.39 g, quant. yield):

$^1$H NMR (400 MHz, DMSO-$d_6$) δ 7.81 (d, J=2.0 Hz, 1H), 7.65 (dd, J=8.7, 2.1 Hz, 1H), 7.56-53 (m, 2H), 7.24-7.21 (m, 2H), 6.76 (d, J=8.7 Hz, 1H), 6.36 (s, 2H), 3.75 (s, 3H), 2.33 (s, 3H);

$^{13}$C NMR (100 MHz, DMSO-$d_6$) δ 165.7, 153.4, 138.2, 133.8, 131.4, 131.0, 129.2, 119.6, 116.2, 113.2, 105.1, 94.4, 84.9, 51.5, 21.1.

Methyl 4-amino-3-((4-ethylphenyl)ethynyl)benzoate (45)

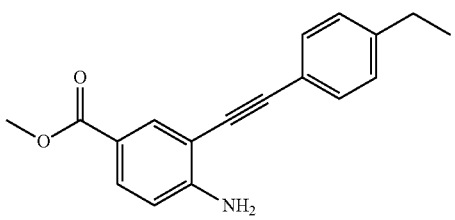 [SMILES: CCc1ccc(C#Cc2cc(C(=O)OC)ccc2N)cc1]

A combined suspension of methyl 4-amino-3-iodobenzoate (2.0 g, 7.22 mmol), copper (I) iodide (28 mg, 0.14 mmol), bis(triphenylphosphine)palladium(II) dichloride (101 mg, 0.14 mmol), and 1-ethyl-4-ethynylbenzene (1.22 mL, 8.66 mmol) were stirred in toluene and TEA (1/1, 60 mL) at ambient temperature for overnight. The reaction solvent was evaporated under reduced pressure, and the residue was purified by column chromatography with hexane/ethyl acetate (5/1, v/v) to obtain the compound 45 as a white solid (2.02 g, quant. yield):

$^1$H NMR (400 MHz, CDCl$_3$) δ 8.07 (d, J=2.0 Hz, 1H), 7.78 (dd, J=8.6, 2.1 Hz, 1H), 7.41 (d, J=8.2 Hz, 2H), 7.12 (d, J=8.2 Hz, 2H), 6.64 (d, J=8.6 Hz, 1H), 4.86 (s, 2H), 3.81 (s, 3H), 2.6 (q, J=7.6 Hz, 2H), 1.19 (t, J=7.6 Hz, 3H);

$^{13}$C NMR (100 MHz, CDCl$_3$) δ 166.6, 151.7, 144.8, 134.1, 131.3, 131.1, 127.9, 119.8, 118.8, 113.1, 107.1, 95.2, 84.1, 51.6, 28.7, 15.2.

Methyl 4-amino-3-((4-methoxyphenyl)ethynyl)benzoate (46)

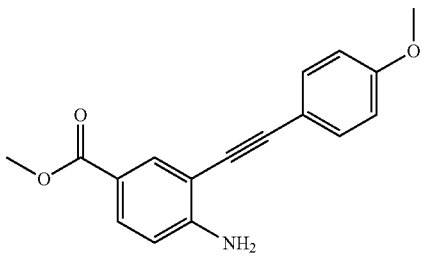

A combined suspension of methyl 4-amino-3-iodobenzoate (3.0 g, 10.83 mmol), copper (I) iodide (41 mg, 0.22 mmol), bis(triphenylphosphine)palladium(II) dichloride (152 mg, 0.22 mmol), and 1-ethynyl-4-methoxybenzene (1.69 mL, 12.99 mmol) were stirred in toluene and TEA (1/1, 90 mL) at ambient temperature for overnight. The reaction solvent was evaporated under reduced pressure, and the residue was purified by column chromatography with hexane/ethyl acetate (3/1, v/v) to obtain the compound 46 as a white solid (2.96 g, 97% yield):

$^1$H NMR (400 MHz, CDCl$_3$) δ 8.06 (d, J=2.1 Hz, 1H), 7.77 (dd, J=8.6, 2.1 Hz, 1H), 7.41 (d, J=8.4 Hz, 2H), 6.82 (d, J=8.4 Hz, 2H), 6.65 (d, J=8.6 Hz, 1H), 4.88 (s, 2H), 3.82 (s, 3H), 3.73 (s, 3H);

$^{13}$C NMR (101 MHz, CDCl$_3$) δ 166.6, 159.6, 151.6, 134.0, 132.8, 131.0, 118.8, 114.7, 113.9, 113.1, 107.2, 95.0, 83.4, 55.1, 51.6.

Methyl 4-amino-3-((3-methoxyphenyl)ethynyl)benzoate (47)

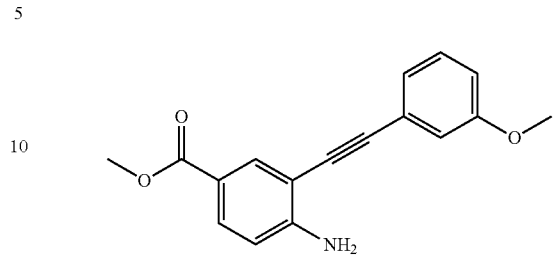

A combined suspension of methyl 4-amino-3-iodobenzoate (3.0 g, 10.83 mmol), copper (I) iodide (41 mg, 0.22 mmol), bis(triphenylphosphine)palladium(II) dichloride (152 mg, 0.22 mmol), and 1-ethynyl-3-methoxybenzene (1.69 mL, 12.99 mmol) were stirred in toluene and TEA (1/1, 90 mL) at ambient temperature for overnight. The reaction solvent was evaporated under reduced pressure, and the residue was purified by column chromatography with hexane/ethyl acetate (3/1, v/v) to obtain the compound 47 as a white solid (3.00 g, 98% yield):

$^1$H NMR (400 MHz, CDCl$_3$) δ 8.07 (d, J=2.1 Hz, 1H), 7.78 (dd, J=8.2, 2.0 Hz, 1H), 7.21 (t, J=7.9 Hz, 1H), 7.08 (dt, J=7.7, 1.2 Hz, 2H), 7.03-7.02 (m, 2H), 6.87-6.86 (m, 1H), 6.66 (d, J=8.6 Hz, 1H), 4.90 (s, 2H), 3.82 (s, 3H), 3.74 (s, 3H);

$^{13}$C NMR (100 MHz, CDCl$_3$) δ 166.5, 159.2, 151.7, 134.3, 131.3, 129.4, 123.8, 123.7, 118.8, 116.2, 114.8, 113.2, 106.7, 94.9, 84.6, 55.1, 51.6.

Methyl 4-amino-3-(benzo[d][1,3]dioxol-5-ylethynyl)benzoate (48)

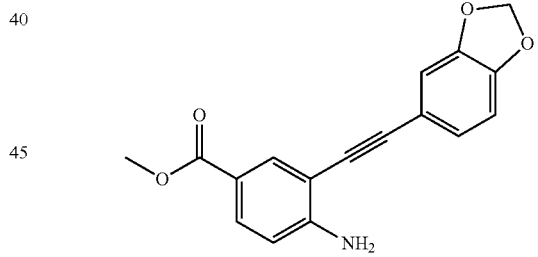

A combined suspension of methyl 4-amino-3-iodobenzoate (2.74 g, 9.90 mmol), copper (I) iodide (38 mg, 1.98 mmol), bis(triphenylphosphine)palladium(II) dichloride (139 mg, 1.98 mmol), and 5-ethynylbenzo[d][1,3]dioxole (1.74 g, 11.89 mmol) were stirred in toluene and TEA (1/1, 82 mL) at ambient temperature for overnight. The reaction solvent was evaporated under reduced pressure, and the residue was purified by column chromatography with hexane/ethyl acetate (3/1, v/v) to obtain the compound 48 as a white solid (2.92 g, quant. yield):

$^1$H NMR (400 MHz, CDCl$_3$) δ 8.04 (d, J=2.0 Hz, 1H), 7.78 (dd, J=8.6, 2.0 Hz, 1H), 7.03 (dd, J=8.0, 1.6 Hz, 1H), 6.94 (d, J=1.6 Hz, 1H), 6.77 (d, J=8.0 Hz, 1H), 6.67 (d, J=8.6 Hz, 1H), 5.97 (s, 2H), 4.74 (bs, 2H), 3.85 (s, 3H);

$^{13}$C NMR (100 MHz, CDCl$_3$) δ 166.7, 151.5, 148.1, 147.5, 134.3, 131.3, 126.2, 119.3, 116.1, 113.3, 111.4, 108.6, 107.2, 101.5, 95.1, 83.2, 51.8.

4-((Trimethylsilyl)ethynyl)phenol (52)

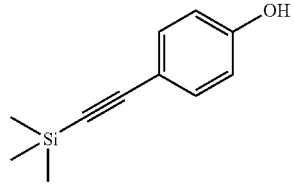

A suspension of 4-iodophenol (3.00 g, 13.64 mmol), ethynyltrimethylsilane (2.27 mL, 16.36 mmol), copper (I) iodide (130 mg, 0.68 mmol), bis(triphenylphosphine)palladium(II) dichloride (479 mg, 0.68 mmol), TEA (5.70 ml, 40.91 mmol) were stirred in THF (23 mL) at ambient temperature for overnight. The reaction solvent was evaporated under reduced pressure, and the residue was purified by column chromatography with hexane/ethyl acetate (2/1, v/v) to obtain the compound 52 (1.76 g, 68% yield):

$^1$H NMR (400 MHz, CDCl$_3$) δ 7.33 (d, J=8.7 Hz, 2H), 6.72 (d, J=8.7 Hz, 2H), 5.82 (bs, 1H), 0.23 (s, 9H);

$^{13}$C NMR (100 MHz, CDCl$_3$) δ 155.8, 133.8, 115.6, 115.4, 105.6, 92.9, 0.1.

(4-((Trimethylsilyl)ethynyl)phenyl)methanol (53)

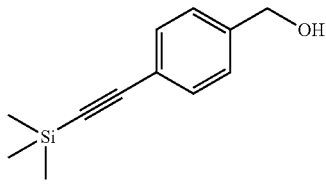

A suspension of (4-iodophenyl)methanol (3.00 g, 13.64 mmol), ethynyltrimethylsilane (2.13 mL, 15.38 mmol), copper (I) iodide (122 mg, 0.64 mmol), bis(triphenylphosphine) palladium(II) dichloride (450 mg, 0.64 mmol), TEA (5.36 ml, 38.46 mmol) were stirred in THF (22 mL) at ambient temperature for overnight. The reaction solvent was evaporated under reduced pressure, and the residue was purified by column chromatography with hexane/ethyl acetate (20/1, v/v) to obtain the compound 53 (2.66 g, quant. yield):

$^1$H NMR (400 MHz, CDCl$_3$) δ 7.44 (d, J=8.4 Hz, 2H), 7.26 (d, J=8.5 Hz, 2H), 4.63 (s, 2H), 2.17 (bs, 1H), 0.25 (s, 9H);

$^{13}$C NMR (100 MHz, CDCl$_3$) δ 141.3, 132.2, 126.7, 122.4, 105.0, 94.3, 64.9, 0.1.

2-(4-((Trimethylsilyl)ethynyl)phenyl)ethan-1-ol (54)

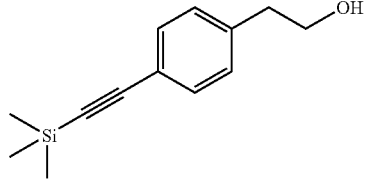

A suspension of (4-iodophenyl)ethanol (3.00 g, 12.09 mmol), ethynyltrimethylsilane (2.01 mL, 14.51 mmol), copper (I) iodide (115 mg, 0.60 mmol), bis(triphenylphosphine) palladium(II) dichloride (424 mg, 0.60 mmol), TEA (5.06 ml, 36.28 mmol) were stirred in THF (20 mL) at ambient temperature for overnight. The reaction solvent was evaporated under reduced pressure, and the residue was purified by column chromatography with hexane/ethyl acetate (5/1, v/v) to obtain the compound 54 (2.64 g, quant. yield):

$^1$H NMR (400 MHz, CDCl$_3$) δ 7.38 (d, J=8.3 Hz, 2H), 7.08 (d, J=8.2 Hz, 2H), 3.66 (td, J=7.0, 3.9 Hz, 2H), 2.72 (t, J=6.8 Hz, 2H), 0.25 (s, 9H);

$^{13}$C NMR (100 MHz, CDCl$_3$) δ 139.4, 132.0, 128.9, 121.0, 105.1, 93.7, 63.0, 38.9, 0.01.

4-Ethynylphenol (55)

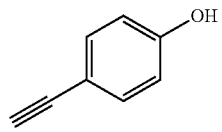

To a solution of 4-((trimethylsilyl)ethynyl)phenol (1.76 g, 9.25 mmol) in THF (19 mL) was added tetrabutylammonium fluoride solution (10.17 ml, 1M in THF). After addition, the reaction was stirred at ambient temperature for 2 h. All the volatile solvent was removed under reduced pressure, and the residue was dissolved in DCM (20 ml). Water (15 mL) was added, and the aqueous layer was extracted with DCM (15 mL×2). The combined organic layer was washed with brine (30 mL), dried over Na$_2$SO$_4$, and filtered. The organic layer was concentrated under reduced pressure and the residue was purified by silica gel chromatography, by column chromatography with hexane/ethyl acetate (5/1, v/v) to obtain the compound 55 as a white solid (511 mg, 47% yield):

$^1$H NMR (400 MHz, CDCl$_3$) δ 7.39 (d, J=8.7 Hz, 2H), 6.78 (d, J=8.7 Hz, 2H), 5.21 (bs, 1H), 3.00 (s, 1H);

$^{13}$C NMR (100 MHz, CDCl$_3$) δ 156.1, 134.0, 115.6, 114.5, 83.7, 76.0.

(4-Ethynylphenyl)methanol (56)

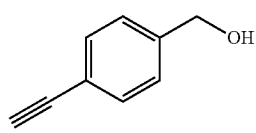

To a solution of (4-((trimethylsilyl)ethynyl)phenyl) methanol (2.96 g, 14.47 mmol) in THF (29 mL) was added tetrabutylammonium fluoride solution (15.92 ml, 1M in THF). After addition, the reaction was stirred at ambient temperature for 2 h. All the volatile solvent was removed under reduced pressure, and the residue was dissolved in DCM (20 ml). Water (15 mL) was added, and the aqueous layer was extracted with DCM (15 mL×2). The combined organic layer was washed with brine (30 mL), dried over Na$_2$SO$_4$, and filtered. The organic layer was concentrated under reduced pressure and the residue was purified by silica gel chromatography, by column chromatography with hexane/ethyl acetate (3/1, v/v) to obtain the compound 56 as a white solid (1.66 mg, 87% yield):

¹H NMR (400 MHz, CDCl₃) δ 7.41 (d, J=8.3 Hz, 2H), 7.17 (d, J=8.6 Hz, 2H), 4.48 (s, 2H), 3.59 (s, 1H), 3.09 (s, 1H);

¹³C NMR (100 MHz, CDCl₃) δ 141.5, 132.2, 126.7, 121.0, 83.5, 77.4, 64.3.

2-(4-Ethynylphenyl)ethan-1-ol (57)

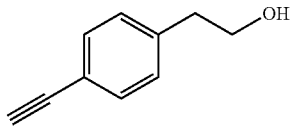

To a solution of 2-(4-((trimethylsilyl)ethynyl)phenyl) ethan-1-ol (2.85 g, 13.07 mmol) in THF (26 mL) was added tetrabutylammonium fluoride solution (14.37 ml, 1M in THF). After addition, the reaction was stirred at ambient temperature for 2 h. All the volatile solvent was removed under reduced pressure, and the residue was dissolved in DCM (10 ml). Water (10 mL) was added, and the aqueous layer was extracted with DCM (15 mL×2). The combined organic layer was washed with brine (30 mL), dried over Na₂SO₄, and filtered. The organic layer was concentrated under reduced pressure and the residue was purified by silica gel chromatography, by column chromatography with hexane/ethyl acetate (1/1, v/v) to obtain the compound 57 as a white solid (1.67 mg, 94% yield):

¹H NMR (400 MHz, CDCl₃) δ 7.39 (d, J=8.3 Hz, 2H), 7.10 (d, J=8.3 Hz, 2H), 3.66 (td, J=6.9, 2.7 Hz, 2H), 3.28 (bs, 1H), 3.09 (s, 1H), 2.72 (t, J=6.8 Hz, 2H);

¹³C NMR (100 MHz, CDCl₃) δ 139.6, 132.0, 128.9, 119.8, 83.6, 7.2, 62.8, 38.7.

tert-Butyl(4-ethynylphenoxy)dimethylsilane (58)

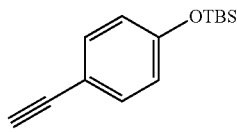 [SMILES: C#Cc1ccc(O[Si](C)(C)C(C)(C)C)cc1]

To a solution of 4-ethynylphenol (511 mg, 4.33 mmol) and imidazole (295 mg, 4.33 mmol) in DMF (13 mL) was added TBDMSCl (652 mg, 4.33 mmol). This reaction mixture was stirred at ambient temperature for overnight. All the volatile solvent was removed under reduced pressure, and the residue was dissolved in DCM (10 ml). Water (10 mL) was added, and the aqueous layer was extracted with DCM (10 mL×2). The combined organic layer was washed with brine (20 mL), dried over Na₂SO₄, and filtered. The organic layer was concentrated under reduced pressure and the residue was purified by silica gel chromatography, by column chromatography with hexane/ethyl acetate (10/1, v/v) to obtain the compound 58 as a brown solid (675 mg, 67% yield):

¹H NMR (400 MHz, CDCl₃) δ 7.41 (d, J=8.6 Hz, 2H), 6.81 (d, J=8.6 Hz, 2H), 3.02 (s, 1H), 1.01 (s, 9H), 0.23 (s, 6H);

¹³C NMR (100 MHz, CDCl₃) δ 156.4, 133.7, 120.3, 115.0, 83.8, 76.1, 25.8, 18.3, −4.3.

tert-Butyl((4-ethynylbenzyl)oxy)dimethylsilane (59)

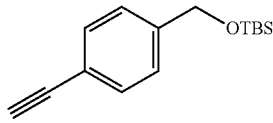

To a solution of (4-ethynylphenyl)methanol (1.66 g, 12.54 mmol) and imidazole (1.71 g, 25.08 mmol) in DMF (37 mL) was added TBDMSCl (2.84 g, 18.81 mmol). This reaction mixture was stirred at ambient temperature for overnight. All the volatile solvent was removed under reduced pressure, and the residue was dissolved in DCM (10 ml). Water (10 mL) was added, and the aqueous layer was extracted with DCM (10 mL×2). The combined organic layer was washed with brine (20 mL), dried over Na₂SO₄, and filtered. The organic layer was concentrated under reduced pressure and the residue was purified by silica gel chromatography, by column chromatography with hexane/ethyl acetate (10/1, v/v) to obtain the compound 59 as a brown solid (2.91 mg, 94% yield):

¹H NMR (400 MHz, CDCl₃) δ 7.46 (d, J=8.2 Hz, 2H), 7.28 (d, J=8.8 Hz, 2H), 4.73 (s, 2H), 3.04 (s, 1H), 0.94 (s, 9H), 0.10 (s, 6H);

¹³C NMR (100 MHz, CDCl₃) δ 142.5, 132.2, 126.0, 120.6, 83.9, 64.7, 26.1, 18.5, −5.1.

tert-Butyl(4-ethynylphenethoxy)dimethylsilane (60)

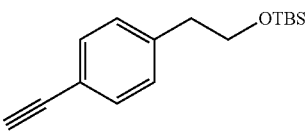 [SMILES: C#Cc1ccc(CCO[Si](C)(C)C(C)(C)C)cc1]

To a solution of 2-(4-ethynylphenyl)ethan-1-ol (1.67 g, 11.40 mmol) and imidazole (1.55 g, 22.79 mmol) in DMF (34 mL) was added TBDMSCl (2.58 g, 17.09 mmol). This reaction mixture was stirred at ambient temperature for overnight. All the volatile solvent was removed under reduced pressure, and the residue was dissolved in DMF (34 ml). Water (10 mL) was added, and the aqueous layer was extracted with DCM (10 mL×2). The combined organic layer was washed with brine (20 mL), dried over Na₂SO₄, and filtered. The organic layer was concentrated under reduced pressure and the residue was purified by silica gel chromatography, by column chromatography with hexane/ ethyl acetate (1/1, v/v) to obtain the compound 60 as a brown solid (2.67 g, 90% yield):

¹H NMR (400 MHz, CDCl₃) δ 7.45 (d, J=8.2 Hz, 2H), 7.20 (d, J=8.2 Hz, 2H), 3.84 (t, J=6.8 Hz, 2H), 3.08 (s, 1H), 2.84 (t, J=6.8 Hz, 2H), 0.93 (s, 9H), 0.03 (s, 6H);

¹³C NMR (100 MHz, CDCl₃) δ 140.3, 132.0, 129.2, 120.0, 83.9, 76.9, 64.1, 39.5, 26.0, 18.3, −5.4.

Methyl 4-amino-3-((4-((tert-butyldimethylsilyl)oxy)phenyl)ethynyl)benzoate (61)

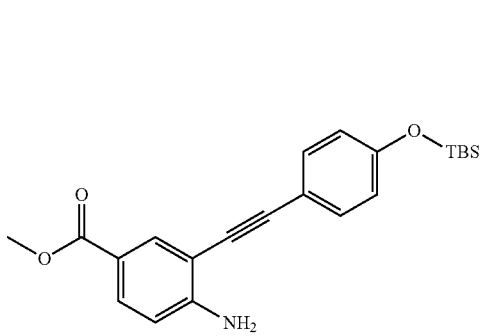

A combined suspension of methyl 4-amino-3-iodobenzoate (1.21 g, 4.36 mmol), copper (I) iodide (17 mg, 0.87 mmol), bis(triphenylphosphine)palladium(II) dichloride (61 mg, 0.87 mmol), and tert-butyl(4-ethynylphenoxy)dimethylsilane (1.22 g, 5.23 mmol) were stirred in toluene and TEA (1/1, 36 mL) at ambient temperature for overnight. The reaction solvent was evaporated under reduced pressure, and the residue was purified by column chromatography with hexane/ethyl acetate (5/1, v/v) to obtain the compound 61 as a brown solid (1.66 g, quant. yield):

$^1$H NMR (400 MHz, CDCl$_3$) δ 8.06 (d, J=2.1 Hz, 1H), 7.80 (dd, J=8.6, 2.0 Hz, 1H), 7.41 (d, J=8.6 Hz, 2H), 6.82 (d, J=8.6 Hz, 2H), 6.68 (d, J=8.5 Hz, 1H), 4.73 (s, 2H), 3.86 (s, 3H), 0.99 (s, 9H), 0.22 (s, 6H);

$^{13}$C NMR (100 MHz, CDCl$_3$) δ 166.8, 156.3, 151.5, 134.3, 133.1, 131.2, 120.4, 119.4, 115.7, 113.3, 107.6, 95.2, 83.6, 51.8, 25.7, 18.3, −4.3.

Methyl 4-amino-3-((4-(hydroxymethyl)phenyl)ethynyl)benzoate (62)

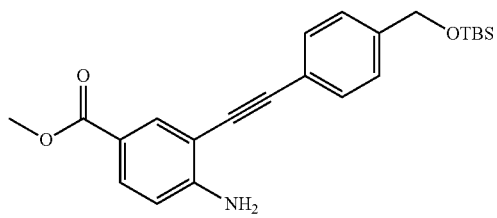 [SMILES: COC(=O)c1ccc(N)c(C#Cc2ccc(CO[Si](C)(C)C(C)(C)C)cc2)c1]

A combined suspension of methyl 4-amino-3-iodobenzoate (2.72 g, 9.83 mmol), copper (I) iodide (37 mg, 0.20 mmol), bis(triphenylphosphine)palladium(II) dichloride (138 mg, 0.20 mmol), and tert-butyl((4-ethynylbenzyl)oxy)dimethylsilane (2.91 g, 11.79 mmol) were stirred in toluene and TEA (1/1, 82 mL) at ambient temperature for overnight. The reaction solvent was evaporated under reduced pressure, and the residue was purified by column chromatography with hexane/ethyl acetate (7/1, v/v) to obtain the compound 62 as a brown solid (3.89 g, quant. yield):

Methyl 4-amino-3-((4-(2-((tert-butyldimethylsilyl)oxy)ethyl)phenyl)ethynyl)benzoate (63)

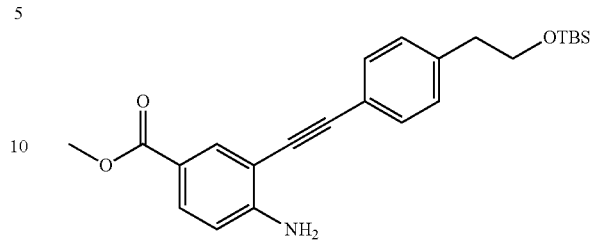

A combined suspension of methyl 4-amino-3-iodobenzoate (2.36 g, 8.53 mmol), copper (I) iodide (33 mg, 0.17 mmol), bis(triphenylphosphine)palladium(II) dichloride (120 mg, 0.17 mmol), and tert-butyl(4-ethynylphenethoxy)dimethylsilane (2.67 g, 10.23 mmol) were stirred in toluene and TEA (1/1, 72 mL) at ambient temperature for overnight. The reaction solvent was evaporated under reduced pressure, and the residue was purified by column chromatography with hexane/ethyl acetate (3/1, v/v) to obtain the compound 63 as a brown solid (3.66 g, quant. yield):

$^1$H NMR (400 MHz, CDCl$_3$) δ 8.04 (d, J=2.1 Hz, 1H), 7.75 (dd, J=8.6, 2.0 Hz, 1H), 7.39 (d, J=8.2 Hz, 2H), 7.12 (d, J=8.3 Hz, 2H), 6.62 (d, J=8.6 Hz, 1H), 4.94 (s, 2H), 3.78 (s, 3H), 3.75 (t, J=6.7 Hz, 2H), 2.75 (t, J=6.7 Hz, 2H), 0.85 (s, 9H), −0.05 (s, 6H);

$^{13}$C NMR (100 MHz, CDCl$_3$) δ 166.4, 151.7, 139.9, 134.1, 131.1, 129.1, 120.3, 118.6, 113.0, 106.8, 95.0, 84.3, 63.8, 51.4, 39.2, 25.7, 18.0, −5.7.

N-(4-Ethynylphenyl)acetamide (65)

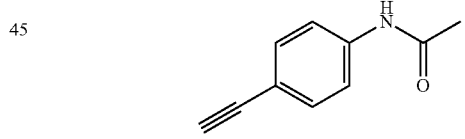

To a solution of 4-ethynylaniline (3.00 g, 25.61 mmol) in DCM (75 mL) was added acetic anhydride (2.71 ml, 28.68 mmol). After addition, the reaction was stirred at ambient temperature for 6 h. And the, water (75 mL) was added, and the aqueous layer was extracted with DCM (15 mL×2). The combined organic layer was washed with brine (30 mL), dried over Na$_2$SO$_4$, and filtered. The organic layer was concentrated under reduced pressure and the residue was purified by silica gel chromatography, by column chromatography with hexane/ethyl acetate (2/1, v/v) to obtain the compound 65 as a white solid (3.41 g, 84% yield):

$^1$H NMR (400 MHz, DMSO-d$_6$) δ 10.10 (s, 1H), 7.59 (d, J=8.7 Hz, 2H), 7.39 (d, J=8.7 Hz, 2H), 4.06 (s, 1H), 2.05 (s, 3H);

$^{13}$C NMR (100 MHz, DMSO-d$_6$) δ 168.5, 139.8, 132.3, 118.7, 115.8, 83.6, 79.7, 24.1.

Methyl 3-((4-acetamidophenyl)ethynyl)-4-aminobenzoate (66)

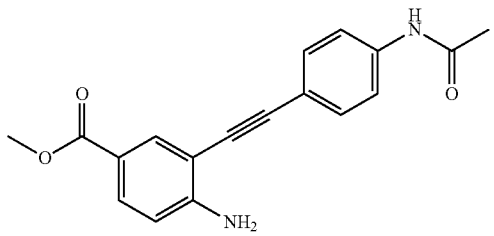 [SMILES: COC(=O)c1ccc(N)c(C#Cc2ccc(NC(C)=O)cc2)c1]

A combined suspension of methyl 4-amino-3-iodobenzoate (3.00 g, 10.83 mmol), copper (I) iodide (41 mg, 0.22 mmol), bis(triphenylphosphine)palladium(II) dichloride (152 mg, 0.22 mmol), and N-(4-ethynylphenyl)acetamide (2.07 g, 12.99 mmol) were stirred in toluene and TEA (1/1, 90 mL) at ambient temperature for overnight. The reaction solvent was evaporated under reduced pressure, and the residue was purified by column chromatography with hexane/ethyl acetate (1/1, v/v) to obtain the compound 66 as a white solid (2.18 g, 65% yield):

$^1$H NMR (400 MHz, DMSO-$d_6$) δ 710.11 (s, 1H), 7.80 (d, J=2.0 Hz, 1H), 7.65-7.56 (m, 5H), 6.75 (d, J=8.7 Hz, 1H), 6.33 (s, 2H), 3.76 (s, 3H), 2.06 (s, 3H);

$^{13}$C NMR (100 MHz, DMSO-$d_6$) δ 168.5, 165.7, 153.4, 139.5, 133.6, 132.1, 130.8, 118.6, 116.8, 116.2, 113.2, 105.2, 94.4, 84.6, 51.5, 24.1.

Methyl (Z)-3-(chloro(4-nitrophenyl)methylene)-2-oxoindoline-5-carboxylate (79)

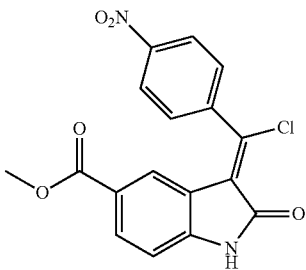 [SMILES: COC(=O)c1ccc2c(c1)/C(=C(/Cl)c1ccc([N+](=O)[O-])cc1)C(=O)N2]

To a solution of triphosgene (371 mg, 1.25 mmol) in toluene (169 mL) were added methyl 4-amino-3-((4-nitrophenyl)ethynyl)benzoate (1.00 g, 3.38 mmol) and TEA (1.04 mL, 7.43 mmol). After addition, the reaction was stirred at ambient temperature for 3 h. All the volatile solvent was removed under reduced pressure, the crude methyl 4-isocyanato-3-((4-nitrophenyl)ethynyl)benzoate was obtained as a solid (2.14 g), and then directly was used to next step. This solid compound (2.14 g, 6.85 mmol) was dissolved in DCM (69 mL). FeCl$_3$ (1.67 g, 10.27 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 79 as a yellow solid (624 mg, 52% yield):

$^1$H NMR (400 MHz, DMSO-$d_6$) δ 11.15 (s, 1H), 8.69 (d, J=1.6 Hz, 1H), 8.30 (d, J=8.9 Hz, 2H), 8.01 (dd, J=8.2, 1.7 Hz, 1H), 7.86 (d, J=8.9 Hz, 2H), 7.00 (d, J=8.2 Hz, 1H), 3.86 (s, 3H).

Methyl (Z)-3-(chloro(4-(methoxycarbonyl)phenyl)methylene)-2-oxoindoline-5-carboxylate (80)

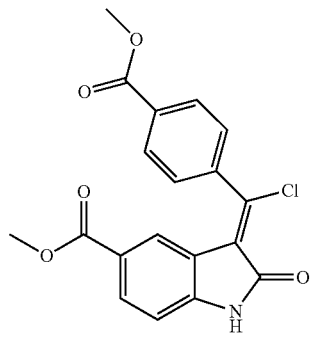 [SMILES: COC(=O)c1ccc(/C(Cl)=C2/C(=O)Nc3ccc(C(=O)OC)cc32)cc1]

To a solution of triphosgene (355 mg, 1.20 mmol) in toluene (162 mL) were added methyl 4-amino-3-((4-(methoxycarbonyl)phenyl)ethynyl)benzoate (1.00 g, 3.23 mmol) and TEA (0.99 mL, 7.11 mmol). After addition, the reaction was stirred at ambient temperature for 3 h. All the volatile solvent was removed under reduced pressure, the crude methyl 4-isocyanato-3-((4-(methoxycarbonyl)phenyl)ethynyl)benzoate was obtained as a solid (2.08 g), and then directly was used to next step. This solid compound (2.08 g, 6.19 mmol) was dissolved in DCM (62 mL). FeCl$_3$ (1.51 g, 9.29 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 80 as a yellow solid (304 mg, 25% yield):

$^1$H NMR (400 MHz, CDCl$_3$) δ 8.88 (s, 1H), 8.11 (d, J=8.7 Hz, 2H), 8.05 (dd, J=8.2, 1.6 Hz, 2H), 7.61 (d, J=8.8 Hz, 2H), 6.85 (d, J=8.2 Hz, 1H), 3.94 (s, 6H).

Methyl (Z)-3-(chloro(3-nitrophenyl)methylene)-2-oxoindoline-5-carboxylate (81)

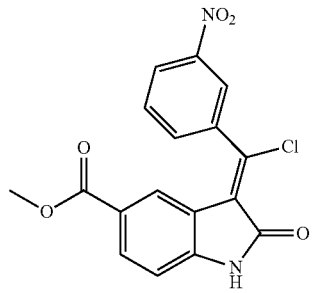 [SMILES: COC(=O)c1ccc2c(c1)/C(=C(/Cl)c1cccc([N+](=O)[O-])c1)C(=O)N2]

To a solution of triphosgene (371 mg, 1.25 mmol) in toluene (169 mL) were added methyl 4-amino-3-((3-nitrophenyl)ethynyl)benzoate (1.00 g, 3.36 mmol) and TEA (1.04 mL, 7.43 mmol). After addition, the reaction was stirred at ambient temperature for 3 h. All the volatile solvent was removed under reduced pressure, the crude methyl 4-isocyanato-3-((3-nitrophenyl)ethynyl)benzoate was obtained as a solid (4.45 g), and then directly was used to next step. This solid compound (4.45 g, 13.81 mmol) was dissolved in DCM (138 mL). FeCl₃ (3.36 g, 20.72 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 81 as a yellow solid (820 mg, 68% yield):

$^1$H NMR (400 MHz, DMSO-$d_6$) δ 11.27 (s, 1H), 8.50 (d, J=1.5 Hz, 2H), 8.11 (d, J=8.0 Hz, 1H), 7.94 (t, J=8.3 Hz, 1H), 7.81 (dd, J=8.3, 1.7 Hz, 1H), 6.73 (d, J=1.6 Hz, 1H), 3.63 (s, 3H).

Methyl (Z)-3-(chloro(p-tolyl)methylene)-2-oxoindoline-5-carboxylate (82)

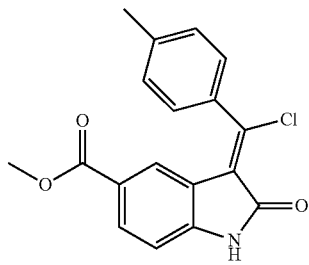 [SMILES: COC(=O)c1ccc2c(c1)/C(=C(/Cl)c1ccc(C)cc1)C(=O)N2]

To a solution of triphosgene (414 mg, 1.40 mmol) in toluene (189 mL) were added methyl 4-amino-3-(p-tolylethynyl)benzoate (1.00 g, 3.77 mmol) and TEA (1.16 mL, 8.29 mmol). After addition, the reaction was stirred at ambient temperature for 3 h. All the volatile solvent was removed under reduced pressure, the crude methyl 4-isocyanato-3-(p-tolylethynyl)benzoate was obtained as a solid (2.70 g), and then directly was used to next step. This solid compound (2.70 g, 9.27 mmol) was dissolved in DCM (93 mL). FeCl₃ (2.26 g, 13.91 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 82 as a yellow solid (1.24 g, quant. yield):

Methyl (Z)-3-(chloro(4-ethylphenyl)methylene)-2-oxoindoline-5-carboxylate (83)

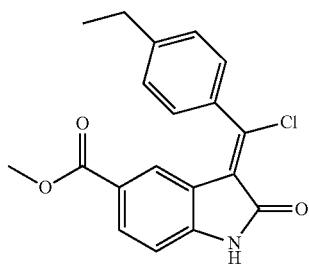 [SMILES: CCc1ccc(/C(Cl)=C2/C(=O)Nc3ccc(C(=O)OC)cc32)cc1]

To a solution of triphosgene (393 mg, 1.32 mmol) in toluene (180 mL) were added methyl 4-amino-3-((4-ethylphenyl)ethynyl)benzoate (1.00 g, 3.58 mmol) and TEA (1.10 mL, 7.88 mmol). After addition, the reaction was stirred at ambient temperature for 3 h. All the volatile solvent was removed under reduced pressure, the crude methyl 3-((4-ethylphenyl)ethynyl)-4-isocyanatobenzoate was obtained as a solid (2.60 g), and then directly was used to next step. This solid compound (2.60 g, 8.51 mmol) was dissolved in DCM (85 mL). FeCl₃ (2.07 g, 12.76 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 83 as a yellow solid (1.22 g, quant. yield):

$^1$H NMR (500 MHz, DMSO-$d_6$) δ 11.05 (s, 1H), 8.68 (d, J=1.6 Hz, 1H), 7.95 (dd, J=8.2, 1.7 Hz, 1H), 7.50 (d, J=8.2 Hz, 2H), 7.28 (d, J=8.3 Hz, 2H), 6.95 (d, J=8.2 Hz, 1H), 3.84 (s, 3H), 2.67 (q, J=7.6 Hz, 2H), 1.22 (t, J=7.6 Hz, 3H);

$^{13}$C NMR (125 MHz, DMSO-$d_6$) δ 166.0, 165.3, 146.5, 146.2, 146.1, 134.3, 132.1, 129.5, 127.3, 125.5, 123.7, 122.5, 122.4, 109.6, 52.1, 28.1, 15.3.

Methyl (Z)-3-(chloro(4-methoxyphenyl)methylene)-2-oxoindoline-5-carboxylate (84)

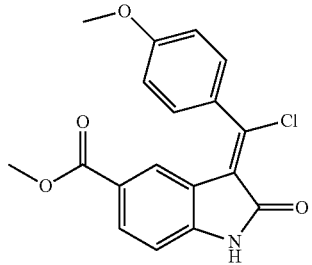 [SMILES: COC(=O)c1ccc2c(c1)/C(=C(/Cl)c1ccc(OC)cc1)C(=O)N2]

To a solution of triphosgene (390 mg, 1.32 mmol) in toluene (178 mL) were added methyl 4-amino-3-((4-methoxyphenyl)ethynyl)benzoate (1.00 g, 3.56 mmol) and TEA (1.09 mL, 7.82 mmol). After addition, the reaction was stirred at ambient temperature for 3 h. All the volatile solvent was removed under reduced pressure, the crude methyl 4-isocyanato-3-((4-methoxyphenyl)ethynyl)benzoate was obtained as a solid (2.30 g), and then directly was used to next step. This solid compound (2.30 g, 7.48 mmol) was dissolved in DCM (75 mL). FeCl₃ (1.82 g, 11.23 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 84 as a yellow solid (932 mg, 76% yield):

$^1$H NMR (400 MHz, DMSO-$d_6$) δ 11.01 (s, 1H), 8.68 (d, J=1.7 Hz, 1H), 7.93 (dd, J=8.2, 1.7 Hz, 1H), 7.56 (d, J=8.9 Hz, 2H), 6.97 (d, J=8.9 Hz, 2H), 6.94 (dd, J=8.2, 0.6 Hz, 1H), 3.83 (s, 3H), 3.82 (s, 3H).

Methyl (Z)-3-(chloro(3-methoxyphenyl)methylene)-2-oxoindoline-5-carboxylate (85)

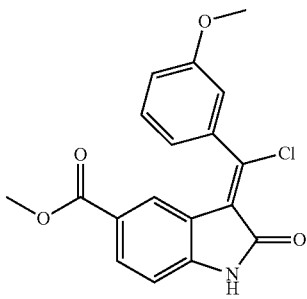 [SMILES: COC(=O)c1ccc2c(c1)/C(=C(/Cl)c1cccc(OC)c1)C(=O)N2]

To a solution of triphosgene (390 mg, 1.32 mmol) in toluene (178 mL) were added methyl 4-amino-3-((4-methoxyphenyl)ethynyl)benzoate (1.00 g, 3.56 mmol) and TEA (1.09 mL, 7.82 mmol). After addition, the reaction was stirred at ambient temperature for 3 h. All the volatile solvent was removed under reduced pressure, the crude methyl 4-isocyanato-3-((4-methoxyphenyl)ethynyl)benzoate was obtained as a solid (2.27 g), and then directly was used to next step. This solid compound (2.27 g, 7.38 mmol) was dissolved in DCM (74 mL). FeCl$_3$ (1.80 g, 11.08 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 85 as a yellow solid (887 mg, 73% yield):

Methyl (Z)-3-(benzo[d][1,3]dioxol-5-ylchloromethylene)-2-oxoindoline-5-carboxylate (86)

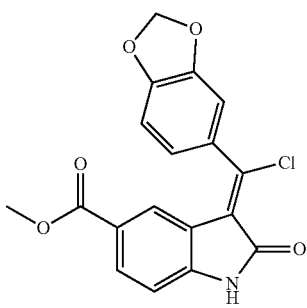 [SMILES: COC(=O)c1ccc2c(c1)/C(=C(/Cl)c1ccc3c(c1)OCO3)C(=O)N2]

To a solution of triphosgene (372 mg, 1.25 mmol) in toluene (169 mL) were added methyl 4-amino-3-(benzo[d][1,3]dioxol-5-ylethynye)benzoate (1.00 g, 3.39 mmol) and TEA (1.04 mL, 7.45 mmol). After addition, the reaction was stirred at ambient temperature for 3 h. All the volatile solvent was removed under reduced pressure, the crude methyl 3-(benzo[d][1,3]dioxol-5-ylethynyl)-4-isocyanatobenzoate was obtained as a solid (2.18 g), and then directly was used to next step. This solid compound (2.18 g, 6.77 mmol) was dissolved in DCM (68 mL). FeCl$_3$ (1.65 g, 10.15 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 86 as a yellow solid (1.21 g, quant. yield):

$^1$H NMR (500 MHz, DMSO-d$_6$) δ 11.02 (s, 1H), 8.67 (s, 1H), 7.95 (d, J=8.1 Hz, 1H), 7.18 (s, 1H), 7.13 (d, J=8.2 Hz, 1H), 7.00-6.95 (m, 2H), 6.12 (s, 2H), 3.85 (s, 3H);

$^{13}$C NMR (125 MHz, DMSO-d$_6$) δ 166.0, 165.3, 149.1, 146.7, 146.0, 145.3, 132.0, 130.4, 125.4, 124.5, 123.7, 122.5, 122.4, 109.9, 109.5, 107.9, 101.7, 52.1.

Methyl (Z)-3-((4-((tert-butyldimethylsilyl)oxy)phenyl)chloromethylene)-2-oxoindoline-5-carboxylate (87)

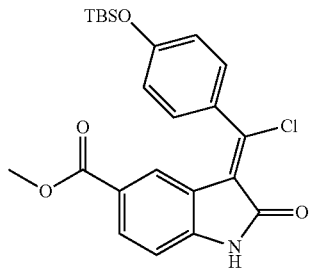 [SMILES: COC(=O)c1ccc2c(c1)/C(=C(/Cl)c1ccc(O[Si](C)(C)C(C)(C)C)cc1)C(=O)N2]

To a solution of triphosgene (288 mg, 0.97 mmol) in toluene (131 mL) were added methyl 4-amino-3-((3-nitrophenyl)ethynyl)benzoate (1.00 g, 2.62 mmol) and TEA (0.80 mL, 5.77 mmol). After addition, the reaction was stirred at ambient temperature for 3 h. All the volatile solvent was removed under reduced pressure, the crude methyl 3-((4-((tert-butyldimethylsilyl)oxy)phenyl)ethynyl)-4-isocyanatobenzoate was obtained as a solid (2.12 g), and then directly was used to next step. This solid compound (2.12 g, 5.19 mmol) was dissolved in DCM (52 mL). FeCl$_3$ (1.26 g, 7.79 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 87 as a yellow solid (218 mg, 19% yield):

$^1$H NMR (400 MHz, CDCl$_3$) δ 10.08 (s, 1H), 7.86 (d, J=8.2 Hz, 1H), 7.44 (d, J=8.7 Hz, 2H), 7.33 (s, 1H), 6.96 (dd, J=8.5, 2.1 Hz, 3H), 3.74 (s, 3H), 1.03 (s, 9H), 0.29 (s, 6H);

$^{13}$C NMR (100 MHz, CDCl$_3$) δ 168.2, 166.7, 158.4, 145.4, 143.2, 131.5, 130.7, 130.5, 124.1, 123.5, 123.2, 122.3, 120.7, 109.9, 52.0, 25.7, 25.7, 18.3, −4.28, −4.30.

Methyl (Z)-3-(chloro(4-(hydroxymethyl)phenyl)methylene)-2-oxoindoline-5-carboxylate (88)

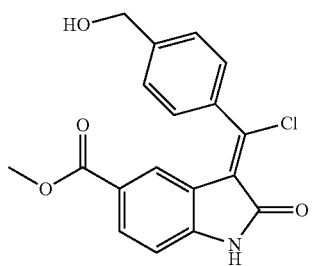 [SMILES: COC(=O)c1ccc2c(c1)/C(=C(/Cl)c1ccc(CO)cc1)C(=O)N2]

To a solution of triphosgene (278 mg, 0.94 mmol) in toluene (126 mL) were added methyl 4-amino-3-((4-(((tert-butyldimethylsilyl)oxy)methyl)phenyl)ethynyl)benzoate (1.00 g, 2.53 mmol) and TEA (0.78 mL, 5.56 mmol). After addition, the reaction was stirred at ambient temperature for 3 h. All the volatile solvent was removed under reduced pressure, the crude methyl 3-((4-(((tert-butyldimethylsilyl)oxy)methyl)phenyl)ethynyl)-4-isocyanatobenzoate was obtained as a solid (2.04 g), and then directly was used to next step. This solid compound (2.04 g, 4.85 mmol) was dissolved in DCM (49 mL). FeCl$_3$ (1.18 g, 7.27 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 88 as a yellow solid (869 mg, 34% yield):

Methyl (Z)-3-((4-(2-((tert-butyldimethylsilyl)oxy)ethyl)phenyl)chloromethylene)-2-oxoindoline-5-carboxylate (89)

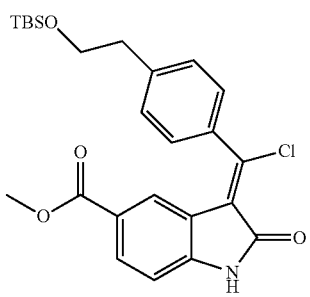 [SMILES: COC(=O)c1ccc2c(c1)/C(=C(/Cl)c1ccc(CCO[Si](C)(C)C(C)(C)C)cc1)C(=O)N2]

To a solution of triphosgene (268 mg, 0.90 mmol) in toluene (122 mL) were added methyl 4-amino-3-((4-(2-((tert-butyldimethylsilyl)oxy)ethyl)phenyl)ethynyl)benzoate (1.00 g, 2.44 mmol) and TEA (0.75 mL, 5.37 mmol). After addition, the reaction was stirred at ambient temperature for 3 h. All the volatile solvent was removed under reduced pressure, the crude methyl 3-((4-(2-((tert-butyldimethylsilyl)oxy)ethyl)phenyl)ethynyl)-4-isocyanatobenzoate was obtained as a solid (2.00 g), and then directly was used to next step. This solid compound (2.00 g, 4.60 mmol) was dissolved in DCM (46 mL). FeCl$_3$ (1.12 g, 6.90 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 89 as a yellow solid (247 mg, 21% yield):

$^1$H NMR (500 MHz, CDCl$_3$) δ 9.10 (s, 1H), 8.28 (s, 1H), 8.22 (dd, J=8.2, 1.7 Hz, 1H), 7.72 (d, J=8.2 Hz, 2H), 7.50 (d, J=8.2 Hz, 2H), 7.47 (s, 1H). 7.02 (d, J=8.2 Hz, 1H), 4.15 (s, 3H), 4.06 (t, J=7.1 Hz, 2H), 3.10 (t, J=7.1 Hz, 2H), 1.10 (s, 9H), 0.23 (s, 6H);

$^{13}$C NMR (125 MHz, CDCl$_3$) δ 167.0, 166.2, 149.0, 144.2, 142.4, 135.0, 132.2, 129.4, 129.0, 126.9, 124.3, 123.4, 123.2, 109.2, 64.3, 52.3, 39.7, 26.1, 18.5, 0.2, −5.2.

Methyl (Z)-3-((4-acetamidophenyl)chloromethylene)-2-oxoindoline-5-carboxylate (90)

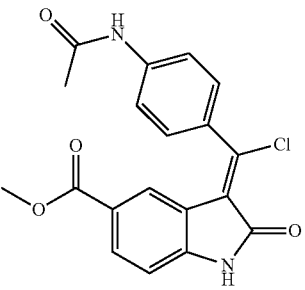 [SMILES: COC(=O)c1ccc2c(c1)/C(=C(/Cl)c1ccc(NC(C)=O)cc1)C(=O)N2]

To a solution of triphosgene (107 mg, 0.36 mmol) in toluene (49 mL) were added methyl 3-((4-acetamidophenyl)ethynyl)-4-aminobenzoate (300 mg, 0.97 mmol) and TEA (0.30 mL, 2.14 mmol). After addition, the reaction was stirred at ambient temperature for 3 h. All the volatile solvent was removed under reduced pressure, the crude methyl 3-((4-acetamidophenyl)ethynyl)-4-isocyanatobenzoate was obtained as a solid (628 mg), and then directly was used to next step. This solid compound (628 mg, 1.88 mmol) was dissolved in DCM (19 mL). FeCl$_3$ (455 mg, 2.82 mmol) was added to the solution. The reaction mixture was stirred at ambient temperature for overnight. The reaction solvent was evaporated under reduced pressure, and the residue was purified by column chromatography with ethyl acetate/ethanol (50/1, v/v) to obtain the major compound 90 as a yellow solid (186 mg, 52% yield):

$^1$H NMR (400 MHz, CDCl$_3$) δ 12.24 (s, 1H), 8.03 (d, J=2.0 Hz, 1H), 8.00 (s, 1H), 7.78 (dd, J=8.5, 2.1 Hz, 2H), 7.52, (d, J=8.7 Hz, 2H), 7.42 (d, J=8.6 Hz, 2H), 6.67 (d, J=8.6 Hz, 1H), 3.85 (s, 3H), 2.15 (s, 3H), 2.05 (s, 3H).

Methyl (Z)-3-(((4-(N-methyl-2-(4-methylpiperazin-1-yl)acetamido)phenyl)amino)(4-nitrophenyl)methylene)-2-oxoindoline-5-carboxylate (91)

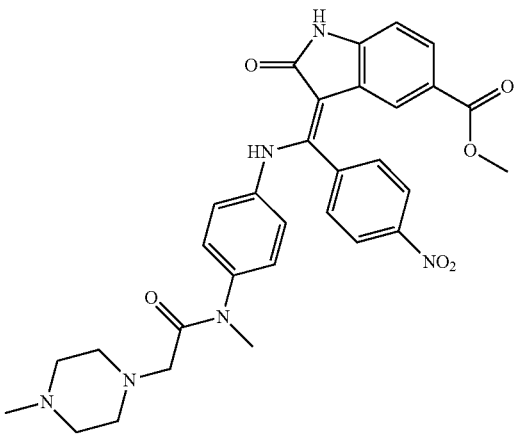

A solution of methyl (Z)-3-(chloro(4-nitrophenyl)methylene)-2-oxoindoline-5-carboxylate (188 mg, 0.52 mmol), N-(4-aminophenyl)-N-methyl-2-(4-methylpiperazin-1-yl)acetamide (158 mg, 0.60 mmol) and TEA (0.15 mL, 1.05 mmol) in EtOH (1.5 mL) was stirred under refluxed for overnight. The reaction solvent was evaporated under reduced pressure, and the residue was purified by column chromatography with dichloromethane/ethanol (50/1, v/v) to obtain the final compound 91 as a yellow solid (267 mg, 87% yield):

$^{1}$H NMR (500 MHz, DMSO-d$_{6}$) δ 11.85 (s, 1H), 11.20 (s, 1H), 8.44 (d, J=8.4 Hz, 2H), 7.88 (d, J=8.4 Hz, 2H), 7.59 (dd, J=8.2, 1.7 Hz, 1H), 7.16 (d, J=8.1 Hz, 2H), 6.99 (d, J=8.2 Hz, 2H), 6.96 (d, J=8.2 Hz, 1H), 6.27 (s, 1H), 3.59 (s, 3H), 3.06 (bs, 2H), 2.66 (bs, 2H), 2.14 (bs, 6H), 2.08 (s, 3H);

$^{13}$C NMR (125 MHz, DMSO-d$_{6}$) δ 170.2, 168.6, 166.2, 154.7, 148.2, 140.7, 140.5, 138.9, 136.9, 130.8, 127.9, 125.8, 124.5, 123.4, 121.3, 119.1, 109.1, 97.6, 59.2, 54.5, 52.4, 51.6, 45.7, 36.7; HRMS (ESI-TOF) m/z calcd for C$_{31}$H$_{32}$N$_{6}$O$_{6}$ [M+Na$^{+}$] 607.2276 found 607.2278.

Methyl (Z)-3-((4-(methoxycarbonyl)phenyl)((4-(N-methyl-2-(4-methylpiperazin-1-yl)acetamido)phenyl)amino)methylene)-2-oxoindoline-5-carboxylate (92)

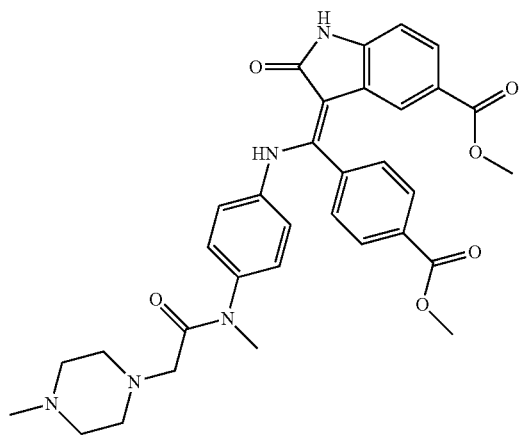

A solution of methyl (Z)-3-(chloro(4-(methoxycarbonyl)phenyl)methylene)-2-oxoindoline-5-carboxylate (10 mg, 0.03 mmol), N-(4-aminophenyl)-N-methyl-2-(4-methylpiperazin-1-yl)acetamide (81 mg, 0.04 mmol) and TEA (0.5 μL, 0.04 mmol) in EtOH (0.3 mL) was stirred under refluxed for overnight. The reaction solvent was evaporated under reduced pressure, and the residue was purified by column chromatography with dichloromethane/ethanol (50/1, v/v) to obtain the final compound 92 as a yellow solid (9.4 mg, 59% yield):

$^{1}$H NMR (400 MHz, CDCl$_{3}$) δ 11.95 (s, 1H), 8.24 (d, J=8.5 Hz, 2H), 7.93 (s, 1H), 7.74 (dd, J=8.2, 1.7 Hz, 1H), 7.57 (d, J=8.5 Hz, 2H), 6.99 (d, J=8.4 Hz, 2H), 6.94 (dd, J=8.2, 0.6 Hz, 1H), 6.79 (d, J=8.6 Hz, 2H), 6.67 (s, 1H), 3.99 (s, 3H), 3.71 (s, 3H), 3.17 (bs, 2H), 2.78 (bs, 2H), 2.38 (bs, 4H), 2.25 (s, 3H), 1.25 (s, 6H).

Methyl (Z)-3-(((4-(N-methyl-2-(4-methylpiperazin-1-yl)acetamido)phenyl)amino)(3-nitrophenyl)methylene)-2-oxoindoline-5-carboxylate (93)

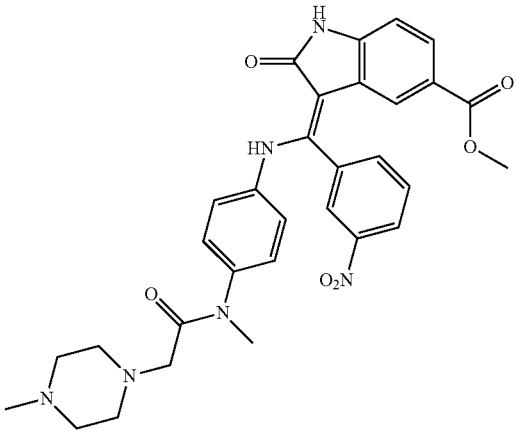

A solution of methyl (Z)-3-(chloro(3-nitrophenyl)methylene)-2-oxoindoline-5-carboxylate (58 mg, 0.16 mmol), N-(4-aminophenyl)-N-methyl-2-(4-methylpiperazin-1-yl)acetamide (48 mg, 0.18 mmol) and TEA (0.05 mL, 0.32 mmol) in EtOH (0.5 mL) was stirred under refluxed for overnight. The reaction solvent was evaporated under reduced pressure, and the residue was purified by column chromatography with dichloromethane/ethanol (50/1, v/v) to obtain the final compound 93 as a yellow solid (84 mg, 90% yield):

$^{1}$H NMR (500 MHz, DMSO-d$_{6}$) δ 11.86 (s, 1H), 11.21 (s, 1H), 8.48 (dd, J=7.6, 1.4 Hz, 2H), 8.00 (d, J=7.8 Hz, 1H), 7.87 (t, J=8.1 Hz, 1H), 7.60 (dd, J=8.2, 1.7 Hz, 1H), 7.16 (d, J=8.2 Hz, 2H), 7.00 (d, J=8.2 Hz, 2H), 6.96 (d, J=8.2 Hz, 1H), 6.42 (s, 1H), 3.62 (s, 3H), 3.05 (bs, 2H), 2.14 (bs, 5H), 2.09 (s, 3H);

HRMS (ESI-TOF) m/z calcd for C$_{31}$H$_{32}$N$_{6}$O$_{6}$ [M+H$^{+}$] 584.2383 found 585.2459.

Methyl (Z)-3-(((4-(N-methyl-2-(4-methylpiperazin-1-yl)acetamido)phenyl)amino)(p-tolyl)methylene)-2-oxoindoline-5-carboxylate (94)

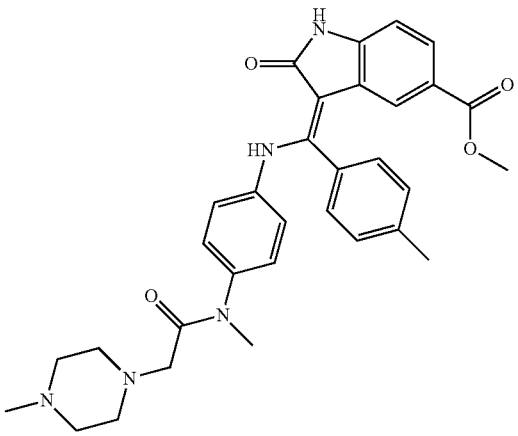

A solution of methyl (Z)-3-(chloro(p-tolyl)methylene)-2-oxoindoline-5-carboxylate (100 mg, 0.31 mmol), N-(4-aminophenyl)-N-methyl-2-(4-methylpiperazin-1-yl)acetamide (92 mg, 0.35 mmol) and TEA (0.09 mL, 0.61 mmol) in EtOH (1.0 mL) was stirred under refluxed for overnight. The reaction solvent was evaporated under reduced pressure, and the residue was purified by column chromatography with dichloromethane/ethanol (50/1, v/v) to obtain the final compound 94 as a yellow solid (169 mg, quant. yield):

$^1$H NMR (500 MHz, DMSO-$d_6$) δ 11.94 (s, 1H), 11.12 (s, 1H), 7.57 (dd, J=8.2, 1.7 Hz, 1H), 7.40-7.36 (m, 4H), 7.14 (d, J=8.1 Hz, 2H), 6.93 (d, J=8.2 Hz, 1H), 6.90 (d, J=8.3 Hz, 2H), 6.50 (s, 1H), 3.64 (s, 3H), 3.05 (bs, 2H), 2.69 (bs, 1H), 2.43 (s, 3H), 2.19 (bs, 6H), 2.10 (s, 3H);

$^{13}$C NMR (125 MHz, DMSO-$d_6$) δ 170.4, 168.6, 166.4, 157.3, 140.4, 140.0, 139.8, 137.5, 130.0, 129.3, 128.4, 127.8, 125.4, 124.1, 123.6, 121.3, 120.0, 108.8, 97.5, 59.2, 54.6, 52.4, 51.6, 45.8, 36.7, 21.1;

HRMS (ESI-TOF) m/z calcd for $C_{31}H_{32}N_6O_6$ [M+H$^+$] 553.2689 found 554.2772.

Methyl (Z)-3-((4-ethylphenyl)((4-(N-methyl-2-(4-methylpiperazin-1-yl)acetamido)phenyl)amino)methylene)-2-oxoindoline-5-carboxylate (95)

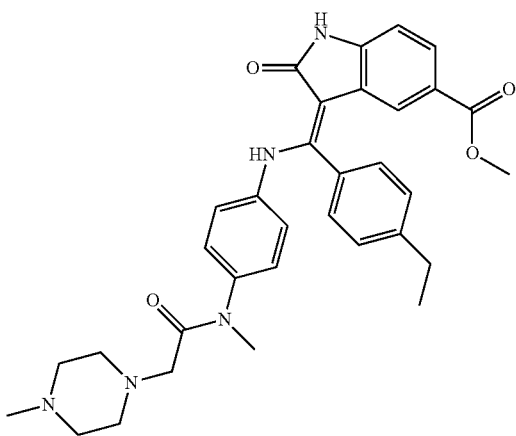

A solution of methyl (Z)-3-(chloro(4-ethylphenyl)methylene)-2-oxoindoline-5-carboxylate (100 mg, 0.29 mmol), N-(4-aminophenyl)-N-methyl-2-(4-methylpiperazin-1-yl)acetamide (88 mg, 0.34 mmol) and TEA (0.08 mL, 0.59 mmol) in EtOH (1.0 mL) was stirred under refluxed for overnight. The reaction solvent was evaporated under reduced pressure, and the residue was purified by column chromatography with dichloromethane/ethanol (50/1, v/v) to obtain the final compound 95 as a yellow solid (166 mg, quant. yield):

$^1$H NMR (500 MHz, DMSO-$d_6$) δ 11.95 (s, 1H), 11.13 (s, 1H), 7.58 (dd, J=8.2, 1.7 Hz, 1H), 7.42-7.38 (m, 5H), 7.13 (d, J=8.2 Hz, 2H), 6.93 (d, J=8.2 Hz, 1H), 6.89 (d, J=8.2 Hz, 2H), 6.51 (s, 1H), 3.62 (s, 3H), 3.05 (bs, 2H), 2.72 (q, J=7.6 Hz, 2H), 2.68 (bs, 2H), 2.18 (bs, 2H), 2.10 (s, 3H), 1.27 (t, J=7.6 Hz, 3H);

$^{13}$C NMR (125 MHz, DMSO-$d_6$) δ 170.4, 168.6, 166.4, 157.3, 146.4, 140.4, 139.8, 137.5, 129.5, 128.9, 128.5, 127.7, 125.6, 124.0, 123.6, 121.3, 119.5, 108.9, 97.5, 59.2, 54.6, 52.4, 51.5, 45.8, 36.7, 28.3, 15.8;

HRMS (ESI-TOF) m/z calcd for $C_{31}H_{32}N_6O_6$ [M+H$^+$] 567.2846 found 568.2941.

Methyl (Z)-3-((4-methoxyphenyl)((4-(N-methyl-2-(4-methylpiperazin-1-yl)acetamido)phenyl)amino)methylene)-2-oxoindoline-5-carboxylate (96)

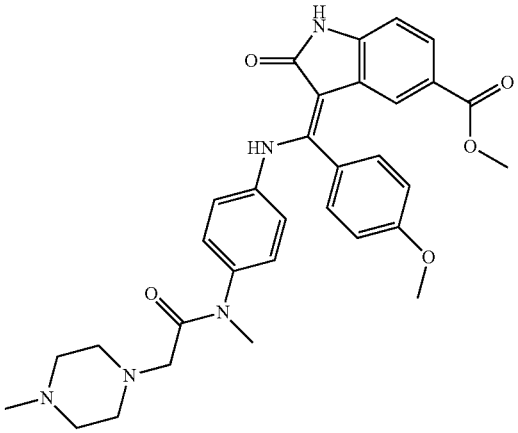

A solution of methyl (Z)-3-(chloro(4-methoxyphenyl)methylene)-2-oxoindoline-5-carboxylate (100 mg, 0.29 mmol), N-(4-aminophenyl)-N-methyl-2-(4-methylpiperazin-1-yl)acetamide (88 mg, 0.34 mmol) and TEA (0.08 mL, 0.59 mmol) in EtOH (1.0 mL) was stirred under refluxed for overnight. The reaction solvent was evaporated under reduced pressure, and the residue was purified by column chromatography with dichloromethane/ethanol (50/1, v/v) to obtain the final compound 96 as a yellow solid (164 mg, 99% yield):

$^1$H NMR (500 MHz, DMSO-$d_6$) δ 11.91 (s, 1H), 11.12 (s, 1H), 7.59 (dd, J=8.2, 1.7 Hz, 1H), 7.43 (d, J=8.6 Hz, 2H), 7.15 (d, J=8.8 Hz, 3H), 6.94 (d, J=8.2 Hz, 1H), 6.90 (d, J=8.4 Hz, 2H), 6.65 (d, J=1.5 Hz, 1H), 3.87 (s, 3H), 3.65 (s, 3H), 3.07 (bs, 3H), 2.87 (bs, 2H), 2.65 (bs. 4H);

$^{13}$C NMR (125 MHz, DMSO-$d_6$) δ 170.4, 166.4, 160.7, 156.8, 140.4, 139.1, 130.2, 127.8, 125.4, 124.15, 124.09, 123.4, 121.2, 119.6, 115.0, 108.8, 97.8, 57.7, 55.5, 52.6, 51.5, 49.1;

HRMS (ESI-TOF) m/z calcd for $C_{32}H_{35}N_5O_5$ [M+Na$^+$] 592.2530, found 592.2531.

Methyl (Z)-3-((3-methoxyphenyl)((4-(N-methyl-2-(4-methylpiperazin-1-yl)acetamido)phenyl)amino)methylene)-2-oxoindoline-5-carboxylate (97)

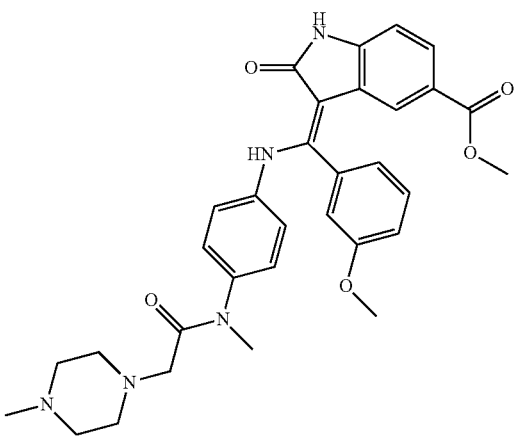

A solution of methyl (Z)-3-(chloro(3-methoxyphenyl)methylene)-2-oxoindoline-5-carboxylate (150 mg, 0.44 mmol), N-(4-aminophenyl)-N-methyl-2-(4-methylpiperazin-1-yl)acetamide (132 mg, 0.50 mmol) and TEA (0.12 mL, 0.87 mmol) in EtOH (1.2 mL) was stirred under refluxed for overnight. The reaction solvent was evaporated under reduced pressure, and the residue was purified by column chromatography with dichloromethane/ethanol (50/1, v/v) to obtain the final compound 97 as a yellow solid (172 mg, 69% yield):

$^1$H NMR (500 MHz, DMSO-$d_6$) δ 11.98 (s, 1H), 11.12 (s, 1H), 7.59 (d, J=8.3 Hz, 1H), 7.49 (t, J=8.0 Hz, 1H), 7.19-7.14 (m, 3H), 7.10 (s, 1H), 7.05 (d, J=7.6 Hz, 1H), 6.93 (t, J=8.4 Hz, 3H), 6.65 (s, 1H), 3.74 (s, 3H), 3.66 (s, 3H), 3.06 (bs, 2H), 2.70 (bs, 2H), 2.19 (bs, 2H), 2.10 (s, 3H);

$^{13}$C NMR (125 MHz, DMSO-$d_6$) δ 170.4, 168.6, 166.4, 160.0, 156.7, 140.4, 139.9, 133.3, 130.8, 127.7, 125.5, 123.8, 123.5, 121.3, 120.5, 119.7, 115.9, 114.0, 108.8, 97.3, 59.1, 55.5, 54.6, 52.4, 51.5, 45.8;

HRMS (ESI-TOF) m/z calcd for $C_{32}H_{35}N_5O_5$ [M+H$^+$] 570.2711, found 570.2714.

Methyl (Z)-3-(benzo[d][1,3]dioxol-5-yl((4-(N-methyl-2-(4-methylpiperazin-1-yl)acetamido)phenyl)amino)methylene)-2-oxoindoline-5-carboxylate (98)

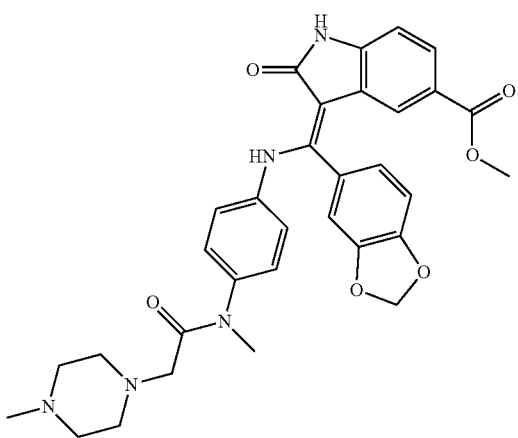

A solution of methyl (Z)-3-(benzo[d][1,3]dioxol-5-yl-chloromethylene)-2-oxoindoline-5-carboxylate (150 mg, 0.42 mmol), N-(4-aminophenyl)-N-methyl-2-(4-methylpiperazin-1-yl)acetamide (127 mg, 0.48 mmol) and TEA (0.12 mL, 0.84 mmol) in EtOH (1.2 mL) was stirred under refluxed for overnight. The reaction solvent was evaporated under reduced pressure, and the residue was purified by column chromatography with dichloromethane/ethanol (50/1, v/v) to obtain the final compound 98 as a yellow solid (179 mg, 73% yield):

$^1$H NMR (500 MHz, DMSO-$d_6$) δ 11.85 (s, 1H), 11.10 (s, 1H), 7.60 (dd, J=8.2, 1.7 Hz, 1H), 7.18 (d, J=8.3 Hz, 2H), 7.11 (d, J=8.1 Hz, 1H), 7.10 (s, 1H), 6.98 (dd, J=8.0, 1.7 Hz, 1H), 6.95-6.93 (m, 3H), 6.72 (s, 1H), 6.16 (s, 1H), 6.12 (s, 1H), 3.69 (s, 3H), 3.08 (bs, 2H), 2.73 (bs, 2H), 2.21 (bs, 3H), 2.11 (s, 3H);

$^{13}$C NMR (125 MHz, DMSO-$d_6$) δ 170.4, 168.6, 166.4, 156.6, 148.7, 148.1, 140.4, 139.9, 127.8, 125.6, 125.4, 124.0, 123.5, 122.8, 121.3, 119.6, 109.4, 109.0, 108.8, 101.7, 97.6, 59.2, 54.6, 52.3, 51.6, 45.7, 36.7;

HRMS (ESI-TOF) m/z calcd for $C_{32}H_{33}N_5O_6$ [M+H$^+$] 584.2504, found 584.2509.

Methyl (Z)-3-((4-((tert-butyldimethylsilyl)oxy)phenyl)((4-(N-methyl-2-(4-methylpiperazin-1-yl)acetamido)phenyl)amino)methylene)-2-oxoindoline-5-carboxylate (99)

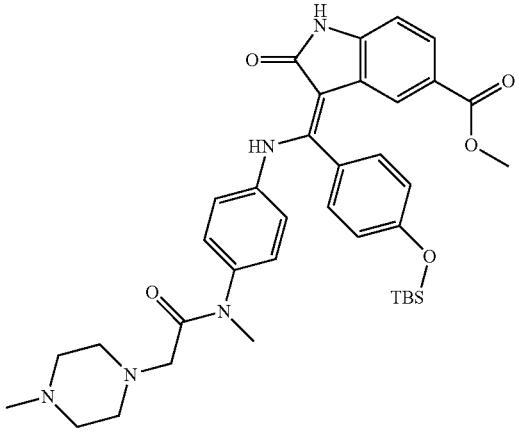

A solution of methyl (Z)-3-((4-((tert-butyldimethylsilyl)oxy)phenyl)chloromethylene)-2-oxoindoline-5-carboxylate (200 mg, 0.45 mmol), N-(4-aminophenyl)-N-methyl-2-(4-methylpiperazin-1-yl)acetamide (136 mg, 0.52 mmol) and TEA (0.13 mL, 0.90 mmol) in EtOH (1.3 mL) was stirred under reflux for overnight. The reaction solvent was evaporated under reduced pressure, and the residue was purified by column chromatography with dichloromethane/ethanol (50/1, v/v) to obtain the final compound 99 (166 mg, 54% yield):

$^1$H NMR (500 MHz, CDCl$_3$) δ 11.93 (s, 1H), 10.08 (s, 1H), 7.74 (dd, J=8.2, 1.6 Hz, 1H), 7.31 (d, J=8.5 Hz, 2H), 7.05 (s, 1H), 7.00 (dd, J=8.3, 1.7 Hz, 3H), 6.97 (d, J=8.4 Hz, 2H), 6.75 (d, J=8.8 Hz, 2H), 3.75 (s, 3H), 3.19 (s, 3H), 2.84 (s, 2H), 2.44 (bs, 6H), 2.27 (s, 3H), 1.04 (s, 9H), 0.91 (s, 2H), 0.29 (s, 6H);

$^{13}$C NMR (125 MHz, CDCl$_3$) δ 171.5, 169.6, 167.5, 157.9, 157.4, 139.9, 139.4, 138.5, 130.4, 127.8, 126.2, 124.9, 124.4, 123.6, 122.7, 121.4, 120.5, 109.1, 98.3, 59.7, 54.9, 53.3, 51.8, 46.1, 37.5, 25.7, 18.4, −3.4, −4.3.

Methyl (Z)-3-((4-(hydroxymethyl)phenyl)((4-(N-methyl-2-(4-methylpiperazin-1-yl)acetamido)phenyl)amino)methylene)-2-oxoindoline-5-carboxylate (100)

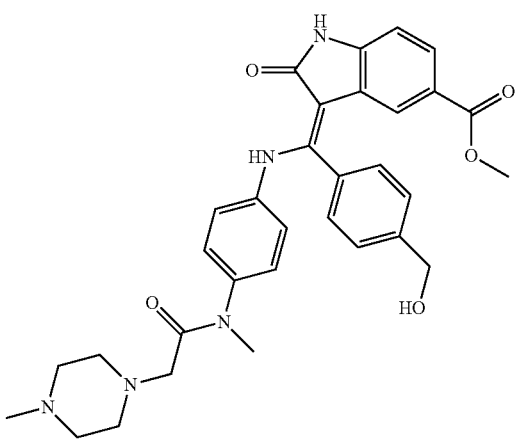

A solution of methyl (Z)-3-(chloro(4-(hydroxymethyl) phenyl)methylene)-2-oxoindoline-5-carboxylate (17 mg, 0.05 mmol), N-(4-aminophenyl)-N-methyl-2-(4-methylpiperazin-1-yl)acetamide (15 mg, 0.06 mmol) and TEA (0.1 µL, 0.10 mmol) in EtOH (0.1 µL) was stirred under refluxed for overnight. The reaction solvent was evaporated under reduced pressure, and the residue was purified by column chromatography with dichloromethane/ethanol (50/1, v/v) to obtain the final compound 100 (15 mg, 52% yield):

$^1$H NMR (500 MHz, DMSO-$d_6$) δ 11.97 (s, 1H), 11.13 (s, 1H), 7.57 (d, J=8.2 Hz, 1H), 7.51 (d, J=7.8 Hz, 2H), 7.44 (d, J=7.8 Hz, 2H), 7.13 (d, J=8.2 Hz, 2H), 6.93 (d, J=8.3 Hz, 1H), 6.90 (d, J=8.2 Hz, 2H), 6.51 (s, 1H), 5.49 (bs, 1H), 4.64 (s, 2H), 3.63 (s, 3H), 3.05 (bs, 2H), 2.69 (bs, 2H), 2.18 (bs, 6H), 2.10 (s, 3H);

$^{13}$C NMR (125 MHz, DMSO-$d_6$) δ 170.4, 168.6, 166.4, 157.2, 145.0, 140.4, 139.8, 130.3, 128.3, 127.8, 127.7, 127.0, 125.5, 124.0, 123.6, 121.3, 119.6, 108.8, 97.6, 62.4, 59.2, 54.6, 52.5, 52.4, 51.6, 51.5, 45.8, 36.7;

HRMS (ESI-TOF) m/z calcd for $C_{31}H_{32}N_6O_6$ [M+H$^+$] 569.2638 found 570.2713.

Methyl (Z)-3-((4-(2-((tert-butyldimethylsilyl)oxy) ethyl)phenyl)((4-(N-methyl-2-(4-methylpiperazin-1-yl)acetamido)phenyl)amino)methylene)-2-oxoindoline-5-carboxylate (101)

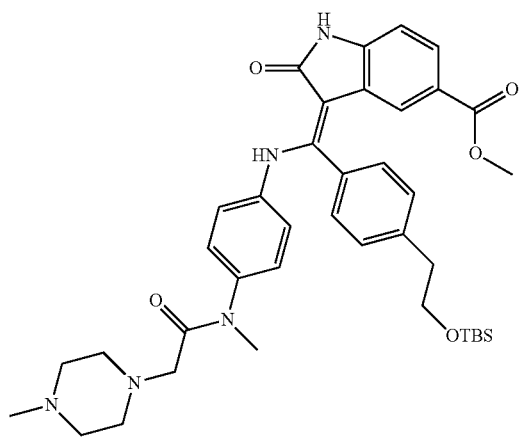

A solution of methyl (Z)-3-((4-(2-((tert-butyldimethylsilyl)oxy)ethyl)phenyl)chloromethylene)-2-oxoindoline-5-carboxylate (138 mg, 0.29 mmol), N-(4-aminophenyl)-N-methyl-2-(4-methylpiperazin-1-yl)acetamide (88 mg, 0.34 mmol) and TEA (0.8 µL, 0.10 mmol) in EtOH (0.8 mL) was stirred under refluxed for overnight. The reaction solvent was evaporated under reduced pressure, and the residue was purified by column chromatography with dichloromethane/ ethanol (50/1, v/v) to obtain the final compound 101 (154 mg, 76% yield):

$^1$H NMR (500 MHz, CDCl$_3$) δ 12.03 (s, 1H), 10.04 (s, 1H), 7.73 (dd, J=8.2, 1.6 Hz, 1H), 7.45 (d, J=7.9 Hz, 2H), 7.39 (d, J=8.2 Hz, 2H), 6.99 (d, J=8.2 Hz, 3H), 6.84 (d, J=8.7 Hz, 2H), 6.69 (d, J=1.7 Hz, 1H), 3.95 (t, J=7.0 Hz, 2H), 3.75 (s, 3H), 3.20 (s, 2H), 3.00 (t, J=7.0 Hz, 2H), 2.45 (bs, 6H), 2.28 (s, 3H), 0.92 (s, 9H), 0.07 (s, 6H);

$^{13}$C NMR (125 MHz, CDCl$_3$) δ 171.4, 169.5, 167.4, 157.3, 142.3, 139.9, 139.3, 138.5, 130.5, 130.1, 128.4, 128.3, 127.9, 126.2, 124.3, 123.2, 122.6, 120.7, 115.7, 109.0, 98.6, 64.3, 59.6, 54.9, 53.3, 51.7.

Methyl (Z)-3-((4-acetamidophenyl)((4-(N-methyl-2-(4-methylpiperazin-1-yl)acetamido)phenyl)amino) methylene)-2-oxoindoline-5-carboxylate (102)

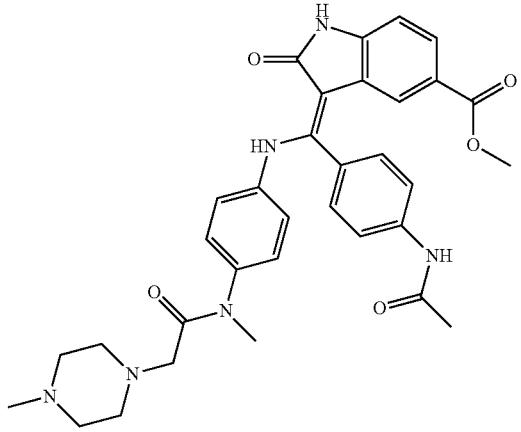

A solution of methyl (Z)-3-((4-acetamidophenyl)chloromethylene)-2-oxoindoline-5-carboxylate (10 mg, 0.03 mmol), N-(4-aminophenyl)-N-methyl-2-(4-methylpiperazin-1-yl)acetamide (8.1 mg, 0.03 mmol) and TEA (0.01 mL, 0.06 mmol) in EtOH (0.1 mL) was stirred under refluxed for overnight. The reaction solvent was evaporated under reduced pressure, and the residue was purified by column chromatography with dichloromethane/ethanol (50/ 1, v/v) to obtain the final compound 102 as a yellow solid (14 mg, 88% yield):

$^1$H NMR (400 MHz, DMSO-$d_6$) δ 11.89 (s, 1H), 11.12 (s, 1H), 10.26 (s, 1H), 7.77 (d, J=8.6 Hz, 2H), 7.58 (dd, J=8.2, 1.7 Hz, 1H), 7.41 (d, J=8.6 Hz, 2H), 7.15 (d, J=8.2 Hz, 2H), 6.93 (d, J=8.2 Hz, 1H), 6.90 (d, J=5.0 Hz, 2H), 6.69 (s, 1H), 3.64 (s, 3H), 3.06 (bs, 2H), 2.67 (bs, 2H), 2.18 (bs, 4H), 2.11 (s, 3H), 2.10 (bs, 2H);

HRMS (ESI-TOF) m/z calcd for $C_{33}H_{36}N_6O_5$ [M+H+] 596.2747 found 597.2818.

Methyl (Z)-3-((4-aminophenyl)((4-(N-methyl-2-(4-methylpiperazin-1-yl)acetamido)phenyl)amino) methylene)-2-oxoindoline-5-carboxylate (103)

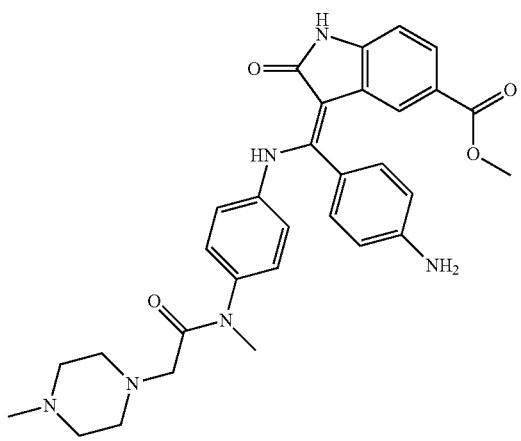

To a solution of methyl (Z)-3-((4-aminophenyl)((4-(N-methyl-2-(4-methylpiperazin-1-yl)acetamido)phenyl)amino)methylene)-2-oxoindoline-5-carboxylate (70 mg, 0.12 mmol) in EtOH (12 mL) was added SnCl$_2$ (91 mg, 0.48 mmol). This reaction mixture was stirred at 70° C. for overnight. The reaction solvent was evaporated under reduced pressure, and the residue was purified by column chromatography with dichloromethane/ethanol (50/1, v/v) to obtain the final compound 103 as a yellow solid (66 mg, quant. % yield):

$^1$H NMR (500 MHz, DMSO-d$_6$) δ 11.79 (s, 1H), 11.03 (s, 1H), 7.58 (dd, J=8.2, 1.8 Hz, 1H), 7.18 (d, J=8.3 Hz, 2H), 7.10 (d, J=8.3 Hz, 3H), 6.92 (d, J=8.2 Hz, 1H), 6.88 (d, J=8.3 Hz, 2H), 6.68 (d, J=8.3 Hz, 2H), 5.76 (bs, 2H), 3.69 (s, 3H), 3.08 (bs, 2H), 2.89 (bs, 2H), 2.71 (bs, 4H), 2.50 (s, 3H);

$^{13}$C NMR (125 MHz, DMSO-d$_6$) δ 170.5, 168.2, 166.6, 158.1, 151.0, 140.2, 138.7, 129.9, 127.8, 125.1, 124.5, 123.1, 121.2, 119.9, 117.9, 113.9, 108.6, 97.3, 57.7, 56.0, 52.6, 51.6, 48.9, 48.6, 36.7;

HRMS (ESI-TOF) m/z calcd for C$_{31}$H$_{34}$N$_6$O$_4$ [M+Na$^+$] 577.2534, found 577.2537.

Methyl (Z)-3-((3-aminophenyl)((4-(N-methyl-2-(4-methylpiperazin-1-yl)acetamido)phenyl)amino)methylene)-2-oxoindoline-5-carboxylate (104)

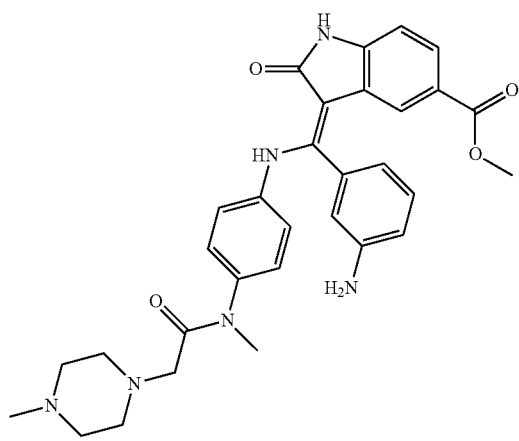

To a solution of methyl (Z)-3-(((4-(N-methyl-2-(4-methylpiperazin-1-yl)acetamido)phenyl)amino)(3-nitrophenyl)methylene)-2-oxoindoline-5-carboxylate (13 mg, 0.12 mmol) in EtOH (2.1 mL) was added SnCl$_2$ (17 mg, 0.09 mmol). This reaction mixture was stirred at 70° C. for overnight. The reaction solvent was evaporated under reduced pressure, and the residue was purified by column chromatography with dichloromethane/ethanol (50/1, v/v) to obtain the final compound 104 as a yellow solid (9.2 mg, 76% yield):

$^1$H NMR (400 MHz, DMSO-d$_6$) δ 12.03 (s, 1H), 11.10 (s, 1H), 7.59 (dd, J=8.2, 1.7 Hz, 2H), 7.26 (t, J=7.8 Hz, 2H), 7.18 (d, J=8.2 Hz, 2H), 6.93 (d, J=8.2 Hz, 1H), 6.82-6.78 (m, 2H), 6.63 (d, J=7.5 Hz, 1H), 6.59 (s, 1H), 5.44 (bs, 2H), 3.67 (s, 3H), 3.08 (bs, 2H), 2.91 (bs, 2H), 2.67 (bs, 2H), 2.50 (s, 3H);

HRMS (ESI-TOF) m/z calcd for C$_{31}$H$_{32}$N$_6$O$_6$ [M+H$^+$] 554.2642 found 555.2706.

Methyl (Z)-3-((4-hydroxyphenyl)((4-(N-methyl-2-(4-methylpiperazin-1-yl)acetamido)phenyl)amino)methylene)-2-oxoindoline-5-carboxylate (105)

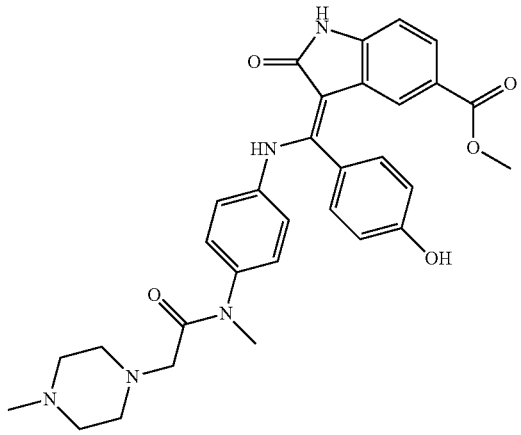

To a solution of methyl (Z)-3-((4-((tert-butyldimethylsilyl)oxy)phenyl)((4-(N-methyl-2-(4-methylpiperazin-1-yl)acetamido)phenyl)amino)methylene)-2-oxoindoline-5-carboxylate (132 mg, 0.20 mmol) in THF (1.0 mL) was added tetrabutylammonium fluoride solution (0.22 ml, 1M in THF). After addition, the reaction was stirred at ambient temperature for 2 h. All the volatile solvent was removed under reduced pressure, and the residue was purified by silica gel chromatography, by column chromatography with dichloromethane/ethanol (50/1, v/v) to obtain the final compound 105 (95 mg, 87% yield):

$^1$H NMR (400 MHz, DMSO-d$_6$) δ 11.87 (s, 1H), 11.07 (s, 1H), 10.07 (bs, 1H), 7.58 (dd, J=8.2, 1.7 Hz, 1H), 7.27 (d, J=8.6 Hz, 2H), 7.15 (d, J=8.2 Hz, 2H), 6.94-6.90 (m, 3H), 6.86 (d, J=8.4 Hz, 2H), 6.81 (d, J=1.6 Hz, 1H), 3.67 (s, 3H), 3.07 (bs, 2H), 2.72 (bs, 2H), 2.21 (bs, 6H), 2.10 (s, 3H);

HRMS (ESI-TOF) m/z calcd for C$_{31}$H$_{32}$N$_6$O$_6$ [M+H$^+$] 555.2482 found 556.2560.

Methyl (Z)-3-((4-(2-hydroxyethyl)phenyl)((4-(N-methyl-2-(4-methylpiperazin-1-yl)acetamido)phenyl)amino)methylene)-2-oxoindoline-5-carboxylate (106)

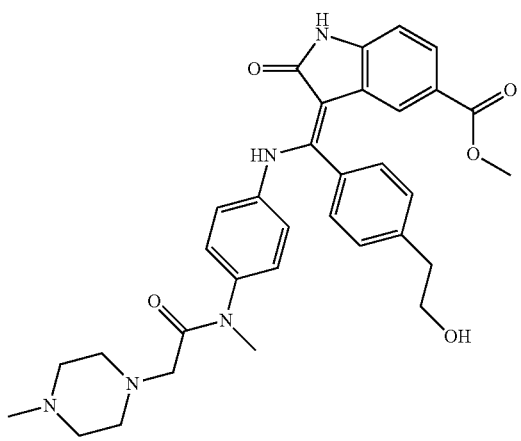

To a solution of methyl (Z)-3-((4-(2-((tert-butyldimethylsilyl)oxy)ethyl)phenyl)((4-(N-methyl-2-(4-methylpiperazin-1-yl)acetamido)phenyl)amino)methylene)-2-oxoindoline-5-carboxylate (154 mg, 0.22 mmol) in THF (1.0 mL) was added tetrabutylammonium fluoride solution (0.24 ml, 1M in THF). After addition, the reaction was stirred at ambient temperature for 2 h. All the volatile solvent was removed under reduced pressure, and the residue was purified by silica gel chromatography, by column chromatography with dichloromethane/ethanol (50/1, v/v) to obtain the final compound 106 (89 mg, 69% yield):

$^1$H NMR (500 MHz, DMSO-$d_6$) δ 11.95 (s, 1H), 11.13 (s, 1H), 7.58 (dd, J=8.1, 1.7 Hz, 1H), 7.45-7.36 (m, 5H), 7.13 (d, J=8.2 Hz, 2H), 6.93 (d, J=8.2 Hz, 1H), 6.88 (d, J=8.2 Hz, 2H), 6.51 (s, 1H), 4.79 (t, J=5.2 Hz, 1H), 3.70-3.67 (m, 2H), 3.35 (s, 3H), 3.05 (bs, 2H), 2.85 (t, J=7.3 Hz, 2H), 2.69 (bs, 1H), 2.53-2.47 (m, 5H), 2.19 (bs, 2H), 2.10 (s, 3H);

$^{13}$C NMR (125 MHz, DMSO-$d_6$) δ 170.4, 168.6, 166.4, 157.3, 141.9, 140.4, 139.8, 137.5, 129.9, 129.8, 128.3, 127.7, 125.6, 124.0, 123.6, 121.3, 119.5, 108.9, 97.5, 62.4, 59.2, 54.6, 52.4, 51.6, 45.8, 36.7;

HRMS (ESI-TOF) m/z calcd for $C_{33}H_{37}N_5O_5$ [M+H+] 583.2795 found 584.2872.

(Z)-3-((4-Aminophenyl)((4-(N-methyl-2-(4-methylpiperazin-1-yl)acetamido)phenyl)amino)methylene)-2-oxoindoline-5-carboxylic acid (107)

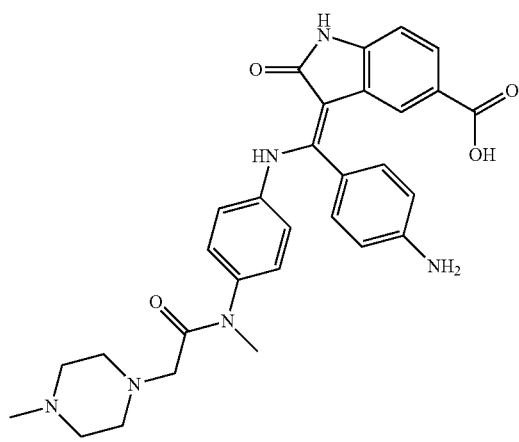 [SMILES: CN1CCN(CC(=O)N(C)c2ccc(N/C(=C3\C(=O)Nc4ccc(C(=O)O)cc43)c3ccc(N)cc3)cc2)CC1]

To a solution of methyl (Z)-3-((4-aminophenyl)((4-(N-methyl-2-(4-methylpiperazin-1-yl)acetamido)phenyl)amino)methylene)-2-oxoindoline-5-carboxylate (300 mg, 0.54 mmol) in MeOH/1,4-dioxane (1/1, 9 mL) was added aqueous 1N NaOH (3.0 mL) at 50° C. This reaction mixture was stirred at 80° C. for 6 h. The reaction solvent was evaporated under reduced pressure, and the residue was filtered by acetonitrile (5.0 mL) and diethyl ether (5.0 mL) to obtain the final compound 107 as a yellow solid (280 mg, 96% yield):

$^1$H NMR (500 MHz, DMSO-$d_6$) δ 11.84 (s, 1H), 10.65 (s, 1H), 7.57 (dd, J=7.9, 1.5 Hz, 1H), 7.35 (s, 1H), 7.10 (bs, 1H), 7.08 (d, J=8.4 Hz, 3H), 6.73 (d, J=8.1 Hz, 3H), 6.60 (d, J=8.2 Hz, 2H), 5.66 (s, 2H), 3.06 (bs, 2H), 2.73 (bs, 2H), 2.24 (bs, 6H), 2.10 (s, 3H);

$^{13}$C NMR (125 MHz, DMSO-$d_6$) δ 171.3, 170.9, 168.7, 156.3, 150.6, 137.1, 132.5, 130.1, 127.5, 125.4, 123.0, 122.4, 120.5, 118.3, 113.7, 107.3, 101.3, 58.9, 54.6, 52.4, 45.8, 36.8;

HRMS (ESI-TOF) m/z calcd for $C_{30}H_{32}N_6O_4$ [M+H+] 541.2558, found 541.2571.

(Z)-3-((3-Aminophenyl)((4-(N-methyl-2-(4-methylpiperazin-1-yl)acetamido)phenyl)amino)methylene)-2-oxoindoline-5-carboxylic acid (108)

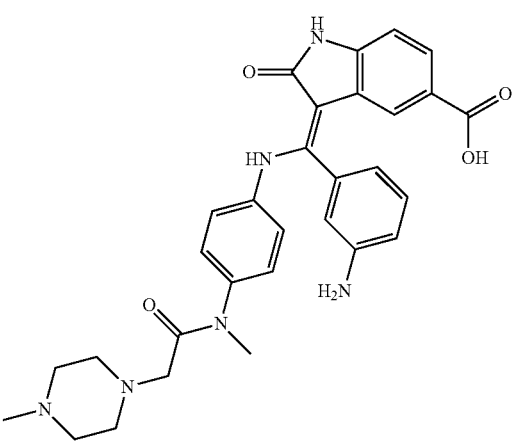 [SMILES: CN1CCN(CC(=O)N(C)c2ccc(N/C(=C3\C(=O)Nc4ccc(C(=O)O)cc43)c3cccc(N)c3)cc2)CC1]

To a solution of methyl (Z)-3-((3-aminophenyl)((4-(N-methyl-2-(4-methylpiperazin-1-yl)acetamido)phenyl) amino)methylene)-2-oxoindoline-5-carboxylate (23.8 mg, 0.14 mmol) in MeOH/1,4-dioxane (1/1, 3 mL) was added aqueous 1N NaOH (0.8 mL) at 50° C. This reaction mixture was stirred at 80° C. for 6 h. The reaction solvent was evaporated under reduced pressure, and the residue was filtered by acetonitrile (5 mL) and diethyl ether (5 mL) to obtain the final compound 108 as a yellow solid (18.6 mg, 80% yield):

HRMS (ESI-TOF) m/z calcd for $C_{31}H_{32}N_6O_6$ [M+H+] 540.2485 found 541.2549.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:
1. A compound according to the following formula:
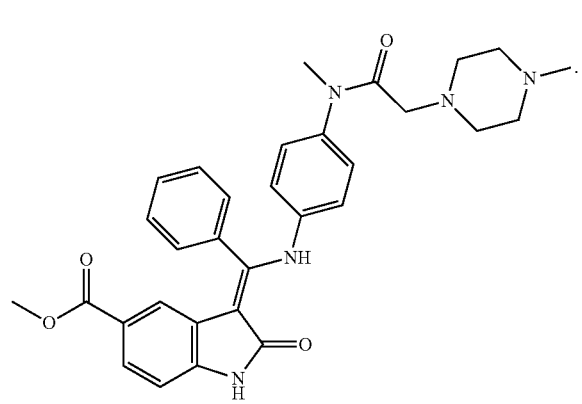
2. A compound according to the following formula:
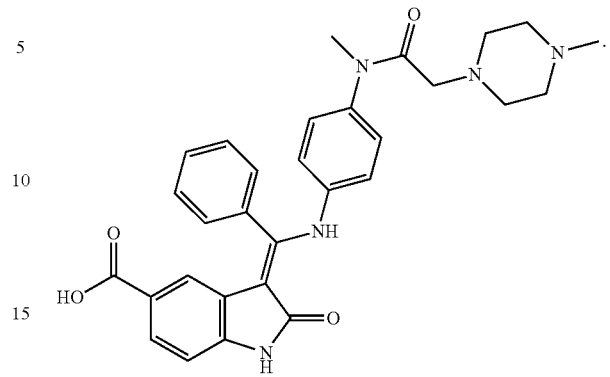
* * * * *